(12) United States Patent
Fahmy et al.

(10) Patent No.: US 10,449,269 B2
(45) Date of Patent: Oct. 22, 2019

(54) PARTICLE CONJUGATED PROSTHETIC PATCHES AND METHODS OF MAKING AND USING THEREOF

(71) Applicant: Yale University, New Haven, CT (US)

(72) Inventors: Tarek M. Fahmy, New Haven, CT (US); Alan Dardik, Bethany, CT (US)

(73) Assignee: YALE UNIVERSITY, New Haven, CT (US)

(*) Notice: Subject to any disclaimer, the term of this patent is extended or adjusted under 35 U.S.C. 154(b) by 128 days.

(21) Appl. No.: 15/687,738

(22) Filed: Aug. 28, 2017

(65) Prior Publication Data

US 2018/0055972 A1    Mar. 1, 2018

Related U.S. Application Data

(60) Provisional application No. 62/380,685, filed on Aug. 29, 2016.

(51) Int. Cl.
*A61L 27/28* (2006.01)
*A61L 27/00* (2006.01)
(Continued)

(52) U.S. Cl.
CPC ........ *A61L 27/3641* (2013.01); *A61K 31/436* (2013.01); *A61K 31/4439* (2013.01); *A61L 27/24* (2013.01); *A61L 27/26* (2013.01); *A61L 27/306* (2013.01); *A61L 27/34* (2013.01); *A61L 27/3604* (2013.01); *A61L 27/3633* (2013.01); *A61L 27/3687* (2013.01); *A61L 27/54* (2013.01); *A61L 2300/62* (2013.01); *A61L 2400/12* (2013.01); *A61L 2400/18* (2013.01); *A61L 2420/06* (2013.01)

(58) Field of Classification Search
USPC ................................................ 623/1.15–1.48
See application file for complete search history.

(56) References Cited

U.S. PATENT DOCUMENTS

| | | |
|---|---|---|
| 4,757,128 A | 7/1988 | Domb |
| 4,789,724 A | 12/1988 | Domb |

(Continued)

OTHER PUBLICATIONS

Abruzzo, et al., "Using Polymeric Scaffolds for Vascular Tissue Engineering", Int. J. Polymer Sci., 9 pages, vol. 2014 Article ID 689390 (2014).

(Continued)

*Primary Examiner* — Suzette J Gherbi
(74) *Attorney, Agent, or Firm* — Pabst Patent Group LLP

(57) ABSTRACT

Composite prosthetic patches with covalently bound particles for controlled drug release, and methods of making and using thereof, have been developed. The particles may encapsulate one or more therapeutic, prophylactic or diagnostic agent(s). Generally, the prosthetic patches are decellularized extracellular matrix such as bovine or porcine pericardium or synthetic polymeric materials. The size of the particles ranges from between 1 nm and 1000 µm, preferably from between 10 nm and 500 nm. In some embodiments, the agent is a therapeutic agent for treatment of neointimal hyperplasia. In other embodiments, the agent is a therapeutic agent for suppressing or resolving inflammation. In yet other embodiments, the agent is a therapeutic for mitigating scarring.

24 Claims, 25 Drawing Sheets

(51) Int. Cl.

| | | |
|---|---|---|
| A61L 27/36 | (2006.01) | |
| A61L 27/24 | (2006.01) | |
| A61L 27/26 | (2006.01) | |
| A61L 27/30 | (2006.01) | |
| A61L 27/34 | (2006.01) | |
| A61L 27/54 | (2006.01) | |
| A61K 31/436 | (2006.01) | |
| A61K 31/4439 | (2006.01) | |

(56) References Cited

U.S. PATENT DOCUMENTS

| | | |
|---|---|---|
| 4,857,311 A | 8/1989 | Domb |
| 4,888,176 A | 12/1989 | Langer |
| 2002/0168320 A1 | 11/2002 | Lanza |
| 2003/0086867 A1 | 5/2003 | Lanza |
| 2003/0129136 A1 | 7/2003 | Lanza |
| 2004/0058951 A1 | 3/2004 | Lanza |
| 2004/0115192 A1 | 6/2004 | Lanza |
| 2006/0147380 A1 | 7/2006 | Lanza |
| 2006/0239919 A1 | 10/2006 | Wickline |
| 2007/0140965 A1 | 6/2007 | Lanza |
| 2007/0202040 A1 | 8/2007 | Lanza |
| 2007/0258908 A1 | 11/2007 | Lanza |
| 2008/0175792 A1 | 7/2008 | Lanza |
| 2008/0247943 A1 | 10/2008 | Lanza |
| 2013/0064765 A1 | 3/2013 | Myerson |
| 2015/0141350 A1* | 5/2015 | Kannan ............... C08G 83/004 514/21.4 |
| 2016/0045502 A1* | 2/2016 | Brown ............... A61K 31/565 514/274 |
| 2019/0046479 A1* | 2/2019 | Pathak ............ A61M 37/0015 |
| 2019/0060517 A1* | 2/2019 | Saint-Pierre .......... A61L 27/227 |

OTHER PUBLICATIONS

Araki, et al., "mTOR regulates memory CD8 T-cell differentiation", Nature, 460:108-12 (2009).
Bai, et al., "Pretreatment of pericardial patches with antibiotics does not alter patch healing in vivo", J Vasc Surg., 63:1063-73 (2016).
Bai, et al., "Covalent modification of pericardial patches for sustained rapamycin delivery inhibits venous neointimal hyperplasia", Sci Rep., 7:40142 (2017).
Bertoli-Avella, et al., "Mutations in a TGF-β ligand, TGFB3, cause syndromic aortic aneurysms and dissections", J Am Coll Cardiol, 65:1324-36 (2015).
Biasi, et al., "Nine-year experience of bovine pericardium patch angioplasty during carotid endarterectomy", J Vasc Surg, 36(2):271-7 (2002).
Bond, et al., "Systematic review of randomized controlled trials of patch angioplasty versus primary closure and different types of patch materials during carotid endarterectomy", J Vasc Surg, 40:1126-35 (2004).
Chen, et al., "TGF-β Neutralization Enhances AngII-Induced Aortic Rupture and Aneurysm in Both Thoracic and Abdominal Regions", PLoS One, 11(4):e0153811 (2016).
Chiu and Chien,, "Effects of disturbed flow on vascular endothelium: pathophysiological basis and clinical perspectives", Physiol Rev., 91:327-87 (2011).
Cyrus, et al,, "Intramural delivery of rapamycin with alphavbeta3-targeted paramagnetic nanoparticles inhibits stenosis after balloon injury", Arterioscler Thromb Vasc Biol, 28:820-6 (2008).
Dai, et al., "Overexpression of transforming growth factor-beta1 stabilizes already-formed aortic aneurysms: a first approach to induction of functional healing by endovascular gene therapy", Circulation, 112:1008-15 (2005).
Dale, et al., "Elastin-Derived Peptides Promote Abdominal Aortic Aneurysm Formation by Modulating M1/M2 Macrophage Polarization", J Immunol, 196:4536-43 (2016).
Dardik, et al., "Differential effects of orbital and laminar shear stress on endothelial cells", J Vasc Surg, 41:869-80 (2005).

Dijke and Arthur, "Extracellular control of TGFbeta signaling in vascular development and disease", Nat Rev Mol Cell Biol, 8(11):857-69 (2007).
Frutkin, et al., "TGF-[beta]1 limits plaque growth, stabilizes plaque structure, and prevents aortic dilation in apolipoprotein E-null mice", Arterioscler Thromb Vasc Biol. 29:1251-7 (2009).
Gillis, et al., "Genetics of thoracic aortic aneurysm: at the crossroad of transforming growth factor-β signaling and vascular smooth muscle cell contractility", Circ Res, 113:327-40 (2013).
Gomez, et al., "Modifications of chromatin dynamics control Smad2 pathway activation in aneurysmal smooth muscle cells", Circ Res, 113:881-90 (2013).
Gomez, et al., "Smad2-dependent protease nexin-1 overexpression differentiates chronic aneurysms from acute dissections of human ascending aorta", Arterioscler Thromb Vasc Biol, 33:2222-32 (2013b).
Gomez, et al., "Syndromic and non-syndromic aneurysms of the human ascending aorta share activation of the Smad2 pathway", J Pathol 218:131-42 (2009).
Gong, et al., "TGFβ signaling plays a critical role in promoting alternative macrophage activation", BMC Immunol 13:31 (2012).
Gordon, et al., "Polytetrafluoroethylene-covered stents in the venous and arterial system: angiographic and pathologic findings in a swine model", Cardiovascular, 17:206-11 (2008).
Goumans, et al., "TGF-beta signaling in vascular biology and dysfunction", Cell Res, 19:116-27 (2009).
Hasan, et al., "Macrophage imbalance (M1 vs. M2) and upregulation of mast cells in wall of ruptured human cerebral aneurysms: preliminary results", J Neuroinflammation, 9:222 (2012).
Ho, et al., "Intermediate-term outcome of carotid endarterectomy with bovine pericardial patch closure compared with Dacron patch and primary closure", J Vasc Surg., 55:708-14 (2012).
Inman, et al., "SB-431542 is a potent and specific inhibitor of transforming growth factor-beta superfamily type I activin receptor-like kinase (ALK) receptors ALK4, ALK5, and ALK7", Mol Pharmacol., 62(1):65-74 (2002).
Jia, et al., "Effects of wall shear stress in venous neointimal hyperplasia of arteriovenous fistulae", Nephrology, 20:335-42 (2015).
Jiang, et al., "Interplay of CCR2 signaling and local shear force determines vein graft neointimal hyperplasia in vivo", FEBS Lett., 583:3536-40 (2009).
Kaplan, et al, "Systemic toxicity following administration of sirolimus (formerly rapamycin) for psoriasis: association of capillary leak syndrome with apoptosis of lesional lymphocytes", Arch Dermatol, 135(5):553-7 (1999).
Kohler and Clowes, "Increased blood flow inhibits neointimal hyperplasia in endothelialized vascular grafts", Circ Res, 69:1557-65 (1991).
Korenblit, et al., "Idiopathic myointimal hyperplasia of the mesenteric veins", Am Surg., 80:E152-4 (2014).
Labowsky and Fahmy, "An in silico analysis of nanoparticle/cell diffusive transfer: application to nano-artificial antigen-presenting cell:T-cell interaction", Nanomedicine, 11:1019-28 (2015).
Li, et al., "Current usage and future directions for the bovine pericardial patch", Ann Vasc Surg., 25(4):561-8 (2011).
Li, et al., "Tgfbr2 disruption in postnatal smooth muscle impairs aortic wall homeostasis", J Clin Invest, 124:755-67 (2014).
Li, et al., "Pericardial patch angioplasty heals via an Ephrin-B2 and CD34 positive cell mediated mechanism", PLoS One, 7(6):e38844 (2012).
Lindsay, et al., "Loss-of-function mutations in TGFB2 cause a syndromic presentation of thoracic aortic aneurysm", Nat Genet. 44:922-7(2012).
Lindsay, et al., "Lessons on the pathogenesis of aneurysm from heritable conditions", Nature. 473:308-16 (2011).
Liu et al., "Pretreatment with intraluminal rapamycin nanoparticle perfusion inhibits neointimal hyperplasia in a rabbit vein graft model", Int J Nanomedicine, 5:853-60 (2010).
Loeys, et al., "Aneurysm syndromes caused by mutations in the TGF-beta receptor", N Engl J Med, 355:788-98 (2006).
Loinard, et al., "Deletion of chromosome 9p21 noncoding cardiovascular risk interval in mice alters Smad2 signaling and promotes vascular aneurysm", Circ Cardiovasc Genet. 7:799-805 (2014).

(56) References Cited

OTHER PUBLICATIONS

Losy, et al., "Paracrine secretion of transforming growth factor-beta1 in aneurysm healing and stabilization with endovascular smooth muscle cell therapy", J Vasc Surg. 37:1301-9 (2003).

Mannheim, et al., "Carotid endarterectomy with a polyurethane patch versus primary closure: a prospective randomized study", J Vasc Surg, 41:403-7 (2005).

Meng, et al., "TGF-β the master regulator of fibrosis", Nat Rev Nephrol., 12:325-38 (2016).

Micha, et al., "SMAD2 Mutations Are Associated with Arterial Aneurysms and Dissections", Hum Mutat, 36:1145-9 (2015).

Morioka, et al., "TAK1 kinase signaling regulates embryonic angiogenesis by modulating endothelial cell survival and migration", Blood.;120:3846-57 (2012).

Muto, et al., "Patches for carotid artery endarterectomy: current materials and prospects", J Vasc Surg 50:206-13 (2009).

Nakao, et al, "TGF-beta receptor-mediated signaling through Smad2, Smad3 and Smad4", EMBO J. 16:5353-62 (1997).

Ohwada, et al., "Glutaraldehyde-fixed heterologous pericardium for vena cava grafting following hepatectomy", Hepatogastroenterology, 46:855-8 (1999).

Papakostas, et al., "Use of the vascu-guard bovine pericardium patch for arteriotomy closure in carotid endarterectomy. Early and long-term results", Ann Vasc Surg, 28(5):1213-8 (2014).

Ravi, et al., "Polymeric materials for tissue engineering of arterial substitutes", Vascular, 17(suppl 1):S45-S54 (2009).

Reddy, et al., "Inhibition of apoptosis through localized delivery of rapamycin-loaded nanoparticles prevented neointimal hyperplasia and reendothelialized injured artery", Circ Cardiovasc Intery, 1(3):209-16 (2008).

Schoenhoff, "Increased TGF-β Signaling Precedes Aneurysm Formation in SMAD3 Deficient Mice", EBioMedicine. 12:26-27(2016).

Shi, et al., "The effect of flow shear stress on endothelialization of impervious Dacron grafts from circulating cells in the arterial and venous systems of the same dog", Ann Vasc Surg., 12:341-8, (1998).

Stheneur, et al., "Identification of 23 TGFBR2 and 6 TGFBR1 gene mutations and genotype-phenotype investigations in 457 patients with Marfan syndrome type I and II, Loeys-Dietz syndrome and related disorders.", Hum Mutat. 29:284-95 (2008).

Suzuki, et al., "Stent-based delivery of sirolimus reduces neointimal formation in a porcine coronary model", Circulation 104:1188-93 (2001).

Wang, et al., "TGF-beta activity protects against inflammatory aortic aneurysm progression and complications in angiotensin II-infused mice", J Clin Invest, 120:422-32 (2010).

Wickline, et al., "Applications of nanotechnology to atherosclerosis, thrombosis, and vascular biology", Arterioscler Thromb Vasc Biol., 26:435-41 (2006).

Xu, et al., "Nanoparticle-delivered transforming growth factor-β siRNA enhances vaccination against advanced melanoma by modifying tumor microenvironment", ACS Nano, 8:3636-45 (2014).

Yang, et al., "Smooth muscle cell-specific Tgfbr1 deficiency promotes aortic aneurysm formation by stimulating multiple signaling events", Sci Rep. 6:35444 (2016).

Zhang, et al., "TGF-β induces M2-like macrophage polarization via SNAIL-mediated suppression of a pro-inflammatory phenotype", Oncotarget, 7:52294-306 (2016).

Zhou, et al., "Nanoparticle-mediated delivery of TGF-β1 miRNA plasmid for preventing flexor tendon adhesion formation", Biomaterials, 34:8269-78 (2013).

Zhou, et al., "Carotid artery aneurysm: evolution of management over two decades", J Vasc Surg. 43:493-6 (2006).

Zippel, et al., "Transforming growth factor-β-activated kinase 1 regulates angiogenesis via AMP-activated protein kinase-α1 and redox balance in endothelial cells", Arterioscler Thromb Vasc Biol, 33:2792-9 (2013).

Zou, et al., "Rapamycin-loaded nanoparticles for inhibition of neointimal hyperplasia in experimental vein grafts.", Ann Vasc Surg.,25:538-46 (2011).

\* cited by examiner

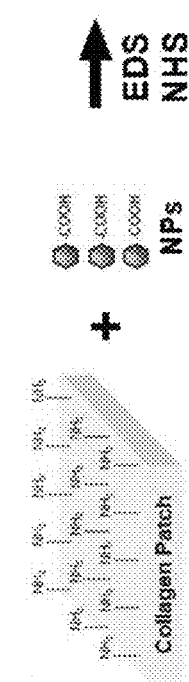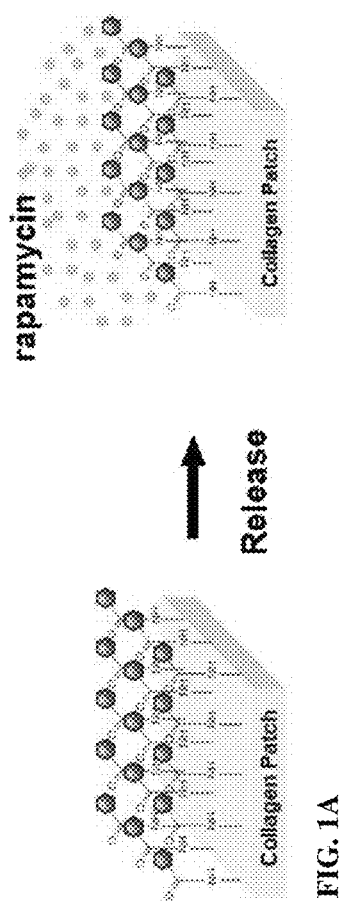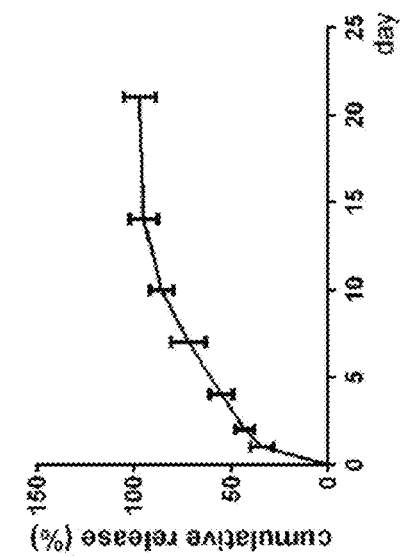
FIG. 1A
FIG. 1B

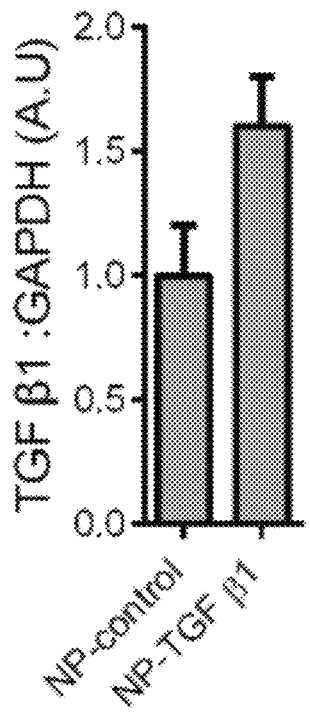 
FIG. 10A  FIG. 10B
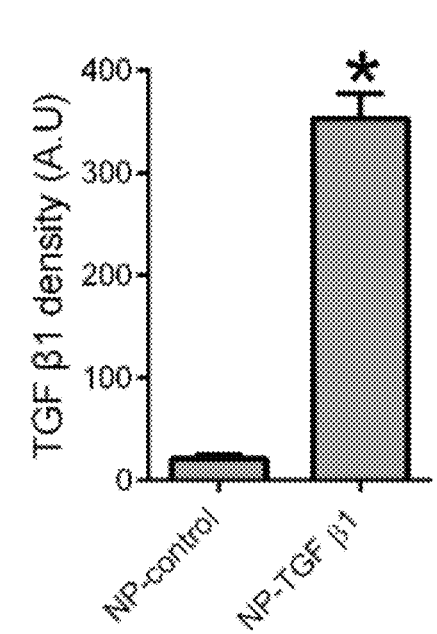 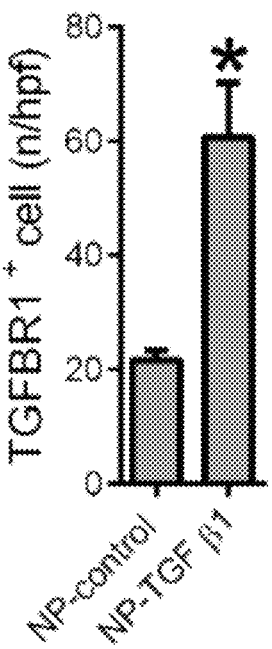
FIG. 10C  FIG. 10D

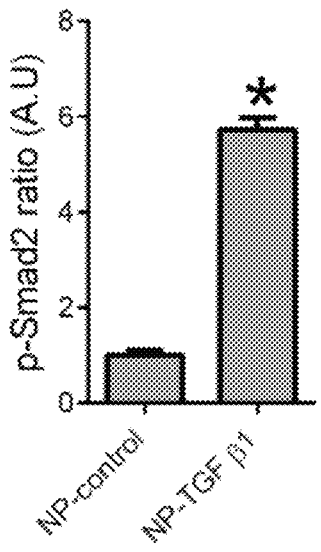
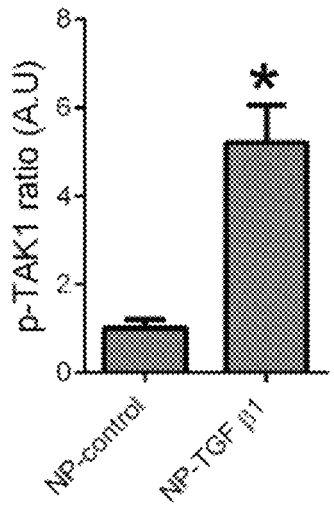
FIG. 10E  FIG. 10F
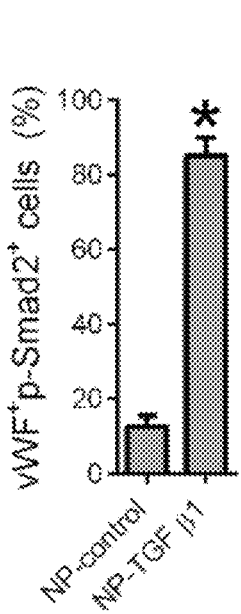
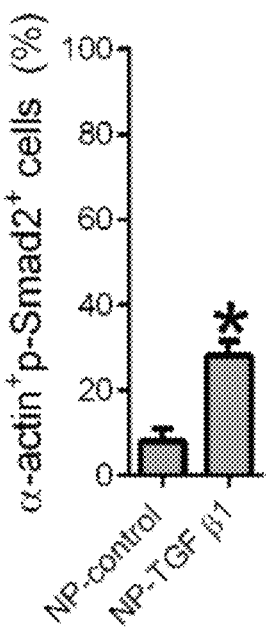
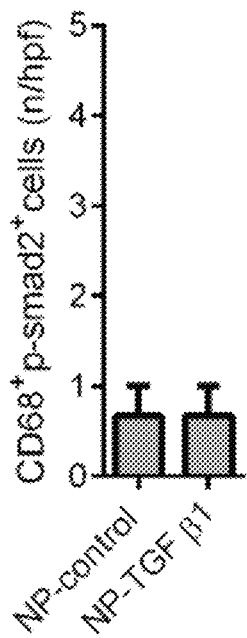
FIG. 10G  FIG. 10H  FIG. 10I

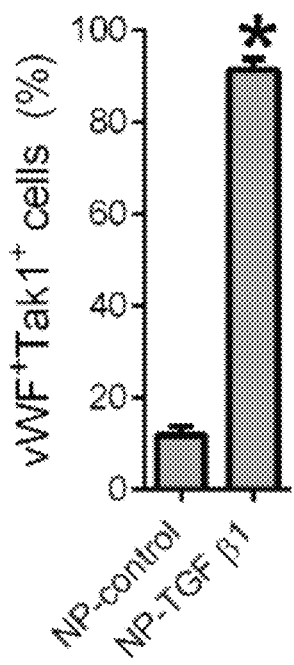
FIG. 10J
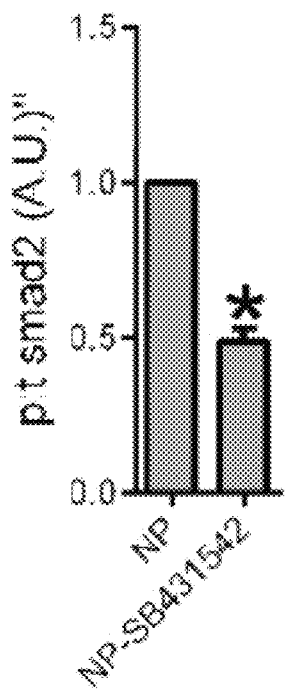 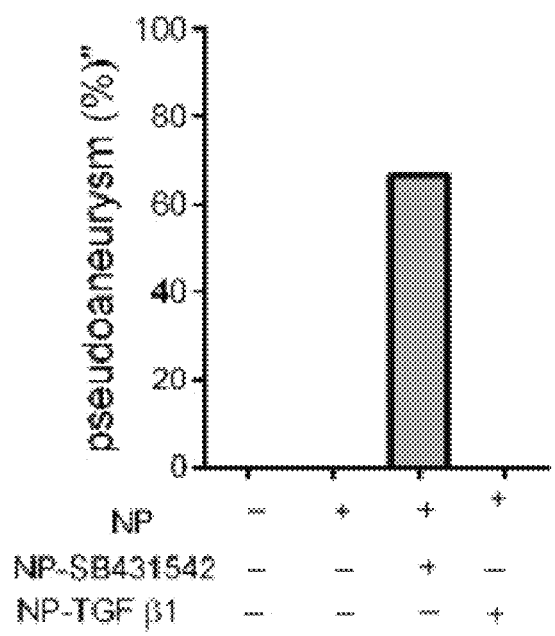
FIG. 11A          FIG. 11B

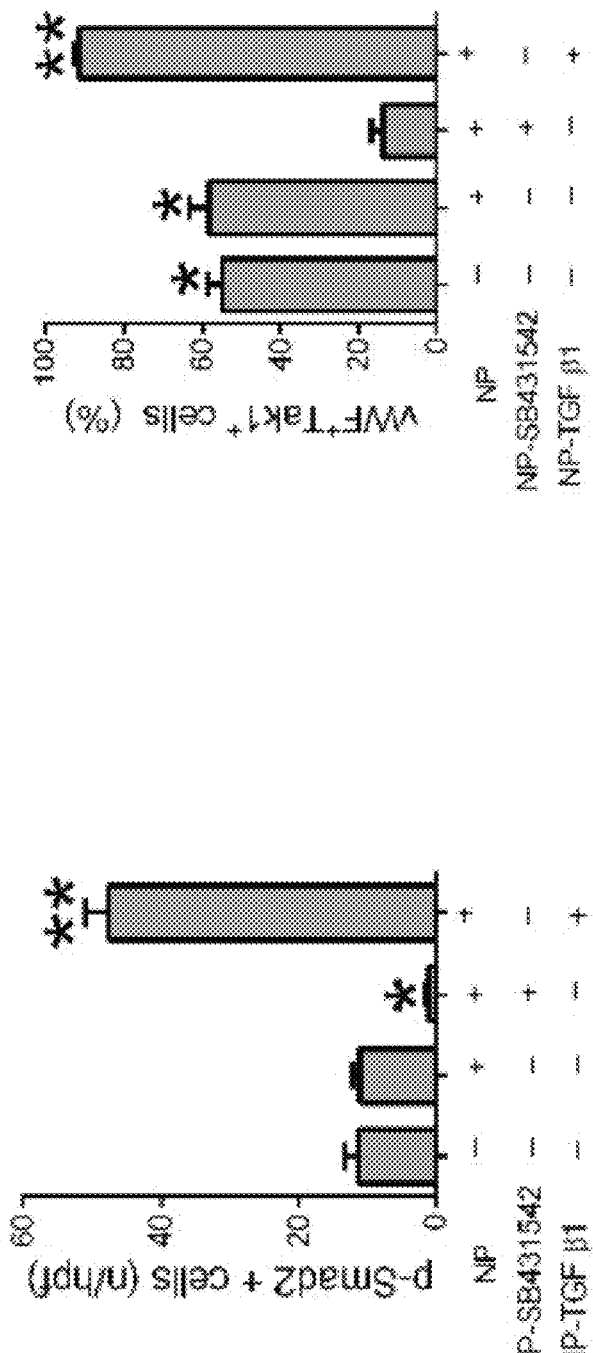
FIG. 11G
FIG. 11H
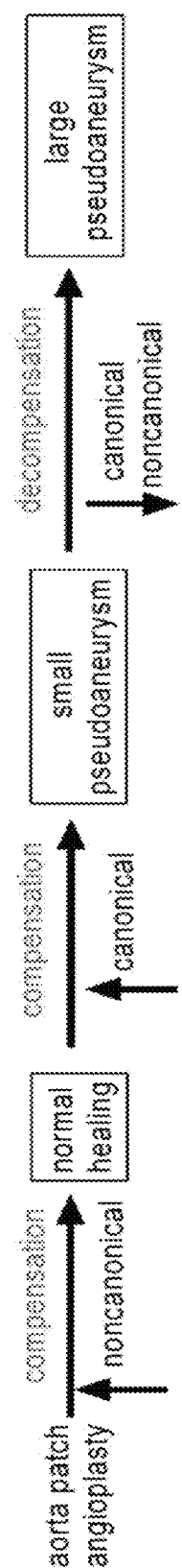
FIG. 12

PARTICLE CONJUGATED PROSTHETIC PATCHES AND METHODS OF MAKING AND USING THEREOF

CROSS-REFERENCE TO RELATED APPLICATIONS

This application claims the benefit of and priority to U.S. Ser. No. 62/380,685 filed Aug. 29, 2016 and which is incorporated by reference in its entirety.

STATEMENT REGARDING FEDERALLY SPONSORED RESEARCH

This invention was made with government support under HL095498 and HL128406 awarded by National Institutes of Health and under I01-BX002336 awarded by The United States of America as represented by the Department of Veterans Affairs. The government has certain rights in the invention.

FIELD OF THE INVENTION

The present invention relates to the field of prosthetic implants and drug delivery, and more particularly, to localized sustained delivery via particle-conjugated prosthetic implants and grafts.

BACKGROUND OF THE INVENTION

Prosthetic patches are widely used for repairs of vasculature, congenital diaphragmatic hernia, orthopedic and fascial defects, as well as in reconstructive surgery and other types of tissue repair. Historically, the first choice of patch material for blood vessels was autogenous saphenous veins, but a separate harvest procedure on patients, risk of infection, and early reports of vein patch blowout led to surgeons using "off-the-shelf" prosthetic materials. Currently, in addition to autogenous saphenous veins, bovine or porcine pericardiums, their decellularized derivatives, and synthetic polymeric materials are commonly used as prosthetic patch materials. However, long-term clinical results have identified several issues that may be related to these materials used as patches including restenosis, pseudoaneurysm formation, infection, fibrosis, calcification and thrombosis (Li, et al., *Ann Vasc Surg.*, 25(4): 561-568 (2011)).

Although open venous surgery is performed less frequently compared to open arterial surgery, patches are also used in venous surgery (Ohwada, et al., *Hepatogastroenterology*, 46, 855-858 (1999)), as venous procedures are frequently complicated by aggressive neointimal hyperplasia and restenosis, possibly due to the lower shear stress in the venous system. Gordon & Levi, *Cardiovascular pathology: the official journal of the Society for Cardiovascular Pathology*, 17, 206-211 (2008); Jia, et al., *Nephrology*, 20, 335-342, (2015); Chiu & Chien, *Physiol Rev.*, 91, 327-387 (2011); Jiang, et al., FEBS Lett., 583, 3536-3540 (2009); and Dardik, et al., *J Vasc Surg*, 41, 869-880 (2005)).

Restenosis remains a common complication after angioplasty, endovascular angioplasty, and open patch angioplasty. A main cause of restenosis is neointimal hyperplasia, i.e. over-proliferation and migration of vascular muscle cells in the tunica intima, in the area at or near the patch, resulting in the thickening of blood vessel walls and luminal narrowing in vessels. In addition, patients with severe vascular disease may develop spontaneous venous neointimal hyperplasia (Korenblit, J. et al. *Am Surg* 80, E152-154 (2014)), placing them at additional risk after conventional venous interventions. The high rates of neointimal hyperplasia and restenosis after venous interventions shows the persistent clinical need for improved techniques or devices to treat patients with venous stenosis. The migration of smooth muscle cells from one tissue compartment to another followed by proliferation in the intima is regulated by factors released from thrombus (e.g. thrombin, PDGF), inflammatory cells (e.g. TNF, IL1b), or the vascular wall cells (bFGF, TGFβ, etc.). These factors as well as related signaling pathways, represent targets for pharmacological blockade and the prevention of intimal hyperplasia. For example, rapamycin (e.g. SIROLIMUS®) and taxol (e.g. PACLITAXEL®) and related adjuvant therapy are popular candidates for suppressing neointimal hyperplasia. However, oral administration of rapamycin induces systemic toxicity, leading to severe adverse effects including fever, anemia, and capillary leak syndrome (Kaplan et al, *Arch Dermatol*, 135(5):553-557 (1999)). Slow-release formulations of rapamycin reduce systemic toxicity and inhibit restenosis to some extent. Rapamycin-loaded nanoparticles reduced neointimal hyperplasia in animal models for both artery and vein injuries compared to no-drug controls (Reddy, et al., *Circ Cardiovasc Interv*, 1(3):209-216 (2008); Liu et al., *Int J Nanomedicine*, 5:853-860 (2010); and Zou, et al., *Annals of vascular surgery* 25, 538-546 (2011)). However, rapamycin-loaded nanoparticles are inconsistent in inhibiting restenosis. For example, intramural administration of slow released rapamycin from non-targeted nanoparticles in a rabbit femoral artery injury model does not differ from administration of saline, neither improving either neointimal hyperplasia, nor vascular stenosis. Integrin αvβ3-targeted nanoparticles delivering rapamycin did induce some improvement (Cyrus et al, *Arterioscler Thromb Vasc Biol*, 28:820-826 (2008)).

Another complication of vascular anastomotic techniques is the potential for development of anastomotic aneurysm. Although the incidence of anastomotic aneurysms is generally low, the prevalence of these aneurysms has increased as a result of the increase of vascular surgeries. The incidence of anastomotic aneurysms after carotid endarterectomy is about 0.3%, and accounts for 13%-57% of extracranial carotid aneurysms, including both true and pseudoaneurysms (Zhou, et al., *J Vasc Surg.* 43:493-496 (2006)).

Current formulations to deliver pharmaceuticals from prosthetic patches for the inhibition of restenosis have several disadvantages. Although pericardial patch angioplasty reduced the rate of restenosis in treated carotid arteries compared to primary closure and remained free from infection (Biasi, et al., *J Vasc Surg*, 36(2):271-277 (2002); Papakostas, et al., *Ann Vasc Surg*, 28(5):1213-1218 (2014)), the inhibition of restenosis in the venous models of patch angioplasty and the prevention of other complications associated with prosthetic patches in general require a drug delivery platform based on the patches. Several factors in current formulations hinder the successful delivery of pharmaceuticals from prosthetic patches. First, patches are stored "wet" and applied in a wet environment, resulting in easy detachment of unbound pharmaceuticals prior to, during and post application. Second, the dosage, kinetics and distribution of released pharmaceuticals need to be precisely controlled. There remains a need for improved prosthetic patch compositions that support localized, sustained delivery of active agents, while avoiding systemic or toxic side effects and minimizing undesired leaching.

Therefore, it is an object of the present invention to provide a composite prosthetic device that delivers active agents locally with a sustained release profile.

It is a further object of the present invention to provide methods of making the composite prosthetic device delivery system.

It is a further object of the invention to provide compositions, methods, and devices to promote healing and inhibit or prevent proliferative diseases and disorders in a subject.

SUMMARY OF THE INVENTION

Composite prosthetic patches with covalently bound particles for controlled drug release, and methods of making and using thereof, have been developed. The prosthetic devices include covalently-bound particles encapsulating one or more therapeutic, prophylactic or diagnostic agents, covalently bound within and/or to the surface of the device. The particles release the one or more agents at a defined rate in vivo following implantation or administration of the device into a subject. Exemplary forms of the device include prosthetic patches, such as a vascular patch, a cutaneous patch, a cardiac patch, or a thoracic patch. The device is typically sized for application to the subject at a location such as the pericardium, blood vessels, the brain, breast tissue, and the site of a hernial reconstruction or repair.

Generally, the prosthetic patches are formed from natural polymers or de-cellularized extracellular matrix such as autologous venous tissue, bovine or porcine pericardium or synthetic polymeric materials. The particles bound to the prosthetic device typically are formed of one or more biodegradable polymers, such as polyesters like poly(lactide-co-glycolide) (PLGA), poly(lactic acid) or polylactide (PLA), poly(ε-caprolactone) (PCL), poly(glycolic acid) or polyglycolide (PGA), poly(D-lactic acid) or poly(D-lactide) (PDLA), poly(L-lactic acid) or poly(L-lactide) (PLLA), polyanhydrides, or poly(ortho esters).

The particles have an average size between 1 nm and 1000 µm, preferably between 10 nm and 500 nm. The particles are covalently bound at a surface density between 0.01 and 1,000 µg/mm$^2$, preferably between 1 and 10 µg/mm$^2$. Typically, the particles are covalently immobilized throughout the body of the prosthetic device as well as on their surfaces using standard techniques such as activation with carbodiimide compounds or through a bi-functional crosslinker.

Exemplary agents released from the particles include antiplatelet agents, anticoagulant agents, anti-inflammatory agents, antimicrobial agents, anti-metabolic agents, anti-neointima agents, immune-modulators, anti-proliferative agents, agents that affect migration and extracellular matrix production, agents that affect platelet deposition or formation of thrombus, and agents that promote vascular healing and re-endothelialization. In some embodiments, the particles encapsulate an amount of therapeutic or prophylactic active agent effective to treat or prevent one or more symptoms of a disease or disorder in a subject. The total amount of each therapeutic or prophylactic active agent encapsulated by all of the particles in the device is typically between about 1 ng and 1,000 µg, inclusive. Generally, the particle bound prosthetic patches are formulated to deliver an effective amount of the agent to alleviate, reduce or prevent one or more symptoms of a disease or disorder. In some embodiments, the particles are bound to prosthetic patches at a density between 0.01 µg/mm$^2$ to 1000 µg/mm$^2$, encapsulating between 1 ng and 1 µg of the agent per 1 µg of particles, resulting in the delivery of the agent between 10 ng/mm$^2$ and 10 mg/mm$^2$ from prosthetic patches. The particle bound patches can release agents over time with a controlled rate. For example, the one more agent(s) encapsulated in the particles can be released over a period of time ranging from between one hour and a few weeks.

In certain embodiments, the particles release the one or more agents in vivo at a constant rate following implantation or administration of the device. For example, in some embodiments, the composite prosthetic device delivers an effective amount of one or more active agents in vivo over a period of between one hour and 31 days following implantation or administration of the device to a subject.

Methods of making and using the particle bound prosthetic patches and one or more active agents encapsulated in these particles have also been developed, for use in delivery of agents locally to a target organ, as well as methods of preventing, suppressing or treating a disease or condition including, but not limited to, neointimal hyperplasia, inflammation, congenital diaphragmatic hernia, orthopedic defects, and fascial defects, and methods of imaging target organs. The methods can further include lyophilizing the device.

Methods of preventing, suppressing or treating one or more symptoms of a disorder, disease or condition may include administering to a subject in need thereof a surgical size unit of the prosthetic patches covalently modified with particles encapsulating the one or more agent(s); which delivers an effective amount of one or more agent(s) to target tissues, such as cardiovasculature, diaphragm, femur and skin; wherein the one or more agent(s) are released from the particles at the target tissues. In preferred embodiments, the methods are directed to preventing, suppressing or treating symptoms of restenosis, neointimal hyperplasia, scarring and over-proliferation of cells. The devices are implanted using standard techniques.

BRIEF DESCRIPTION OF THE DRAWINGS

FIG. 1A is a schematic illustration showing the preparation of a collagen patch covalently conjugated with particles. Amine groups on the patch are coupled with carboxyl groups of the particles using the EDC-NHS chemistry. The immobilized particles release rapamycin over time. FIG. 1B is a line graph showing the percent release of rapamycin in phosphate buffered saline (PBS) at 37° C. from nanoparticle bound patches as cumulative release percentage (%) versus time (day).

FIGS. 10A-10G are bar graphs, showing the ratio TGF β1 to GADPH (A.U.) (p=0.1679, t-test) (FIG. 10A), and TGFBR1 to GADPH (A.U.) (FIG. 10B), respectively, for each of nanoparticle (NP) control, and NP-TGF β1, respectively (* p<0.0001, vs. control); TGF β1 density (A.U.) (* p<0.0001, t-test) (FIG. 10C), and the number of TGFBR1 positive cells per high power field (n/hpf; 0-80) (*, p=0.0002, t-test) (FIG. 10D) for each of NP-control, and NP-TGF β1, respectively; the ratio of phospho- vs. total smad2 (A.U.) (* p=0.0001, t-test), for each of NP-control, and NP-TGF β1, respectively. n=3 (FIG. 10E); the ratio of phosphor- vs. total TAK1 (A.U.) (* p=0.0087, t-test), for each of NP-control, and NP-TGF β1, respectively (FIG. 10F); and % vWF-pSmad2 dual positive cells in the wall (*p=0.0002, t-test) (FIG. 10G); % α-actin-pSmad2 dual positive cells in the wall (*p=0.0127, t-test) (FIG. 10H); CD68-pSmad2 dual positive cells in the wall per high power field (n/hpf; 0-5) (*p>0.9, t-test) (FIG. 10I); and % vWF-TAK1 dual positive cells (* p<0.0001, t-test) (FIG. 10J), respectively, for each of NP-control, and NP-TGF β1, respectively.

FIGS. 11A-11H are bar graphs showing the ratio of phosphor- vs. total smad2 (* p=0.0061, t-test) for each of nanoparticles (NP) and NP-SB431542, respectively (FIG. 11A); the rate of pseudoaneurysm (%)" at day 7 when treated with each of NP, NP-SB431542, or NP-TGF β1, respectively (FIG. 11B); the number of PCNA positive cells per high power field (n/hpf; 0-50) (* p<0.0001, vs. control, NP-SB431542 and NP-TGF β1 patch) (FIG. 11C); cleaved caspase-3 positive cells per high power field (n/hpf; 0-40) (* p<0.0001, vs. control, NP-SB431542 and NP-TGF β1 patch) (FIG. 11D); the number of TGF β1 density in control, NP-control, NP-SB431542 and NP-TGF β1 patches, day 7 (A.U.) (* p<0.035, vs. control, NP-control, NP-SB431542 patch) (FIG. 11E); and the number of TGFBR1 positive cells per high power field (n/hpf; 0-60) at day 7 (* p<0.001, vs. control, NP-control patch; ** p<0.0001, VS. control, NP-control, NP-SB431542 patch) (FIG. 11F), for each of control, NP-control, NP-SB431542 and NP-TGF β1 patches, respectively; the number of p-smad2 positive cells in control, NP-control, NP-SB431542 and NP-TGF β1 patches per high power field (n/hpf; 0-60), respectively, at day 7 (* p<0.035, vs. control, NP-control patch; ** p<0.0001, VS. control, NP-control patch) (FIG. 11G); and the % of vWF and TAK1 dual positive cells in control, NP-control, NP-SB431542 and NP-TGF β1 patches (0-100%), respectively, at day 7 (* p<0.0002, vs. NP-SB431542 patch; ** p<0.0004, VS. control, NP-control patch) (FIG. 11H).

FIG. 12 is a schematic flow-chart representation of a model for the mechanism of pseudoaneurysm formation after patch angioplasty. After patch angioplasty, normal healing is characterized by accumulation of inflammatory cells as well as some smad2-positive and TAK1-positive cells; these TGF-β1 downstream signaling pathways serve as compensatory pathways, preventing degeneration and pseudoaneurysm formation; non-canonical pathway activity may be dominant. Activation of canonical signaling serves as a compensatory pathway, restricting wall degeneration and formation of only a small pseudoaneurysm. Loss of both canonical and non-canonical signaling leads to decompensation and formation of a large pseudoaneurysm. Delivery of TGF-β1 increases smad2 and TAK1 phosphorylation, enhancing compensatory pathways and limiting pseudoaneurysm formation; conversely, inhibiting compensatory pathways and smad2 phosphorylation leads to enhanced pseudoaneurysm formation.

DETAILED DESCRIPTION OF THE INVENTION

I. Definitions

Figure 1C:
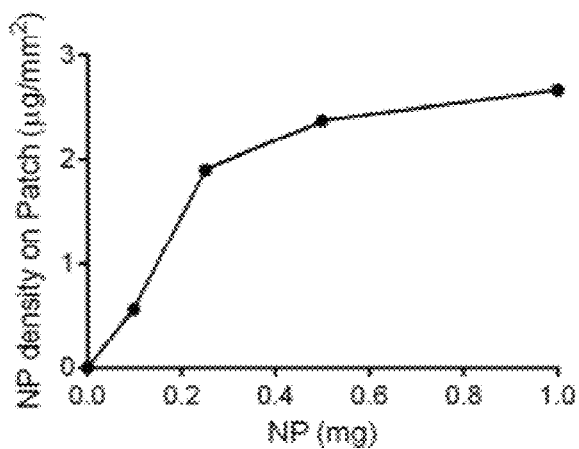
FIG. 1C is a line graph showing the Nanoparticle (NP) density on the patch (µg/mm$^2$) over mass of nanoparticle (mg).

The term "prosthetic" generally refers to a device, either external or implanted, that substitutes for or supplements a missing or defective part of the body. The prosthetic devices can be naturally derived or made from synthetic materials.

The term "patch" generally refers to a small piece of material used as a prosthetic to mend a tear or break, to cover a hole, to strengthen a weak place, typically to cover or protect a wound and an injured part. The patches can have different dimensions as appropriate for the site and purpose of the prosthetic.

The term "active agent" are used to refer to a compound that induces a prophylactic, therapeutic or diagnostic effect. The term also encompasses pharmaceutically acceptable, pharmacologically active derivatives of agents, including, but not limited to, salts, esters, amides, prodrugs, active metabolites, and analogs.

As used herein, the term "effective amount" is an art-recognized term. In certain embodiments, the term refers to an amount of active agents that, when incorporated into the particles attached to and within the prosthetic, produces some desired effect at a reasonable benefit/risk ratio applicable to any medical treatment or diagnostic procedure. In certain embodiments, the term refers to the amount necessary or sufficient to eliminate or reduce one or more symptoms or complications of patch applications in surgical settings for a period of time. The effective amount may vary depending on such factors as the disease or condition being treated, the particular composition being administered, the size of the subject, or the severity of the disease or condition. One of ordinary skill in the art may empirically determine the effective amount of an agent without necessitating undue experimentation.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as but not limited to a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

"Nanoparticle," as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle," as used herein, generally refers to a particle having a diameter, such as an average diameter, from about 1 micron to about 100 microns, preferably from about 1 micron to about 50 microns, more preferably from about 1 to about 30 microns. The microparticles can have any shape. Microparticles having a spherical shape are generally referred to as "microspheres".

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution" are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Pharmaceutically Acceptable," as used herein, refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "encapsulated" and "incorporated" are art-recognized when used in reference to one or more agents, or other materials, into a polymeric composition. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymeric particle, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of more than one active agent or other material and at least one other therapeutic agent or other material in a subject composition.

The term "stenosis" refers to an abnormal narrowing in a blood vessel that occurs following an injury to the vessel wall (endothelium). In some embodiments, stenosis involves a reduction in the circumference of a lumen of 50% or more. The term "restenosis" refers to stenosis at a previously stenotic site or narrowing of the lumen of a blood vessel or synthetic graft following an interventional procedure. Restenosis, as used herein, encompasses occlusion. Exemplary injuries that result in stenosis or restenosis include trauma to an atherosclerotic lesion (as seen with angioplasty or stent), a resection of a lesion (as seen with endarterectomy), an external trauma (e.g., a cross-clamping injury), or a surgical anastomosis.

The term "neointimal stenosis" refers to abnormal narrowing in a blood vessel resulting from neointimal formation.

The term "Pharmaceutically acceptable carrier" encompasses any of the standard pharmaceutical carriers, such as a phosphate buffered saline solution, water and emulsions such as an oil/water or water/oil emulsion, and various types of wetting agents.

The term "Inhibit" or other forms of the word such as "inhibiting" or "inhibition" means to hinder or restrain a particular characteristic. It is understood that this is typically in relation to some standard or expected value, i.e., it is relative, but that it is not always necessary for the standard or relative value to be referred to. For example, "inhibits disease" means hindering, interfering with or restraining the activity of the disease or disorder relative to a standard or a control.

The term "Treatment" or "treating" means to administer a composition to a subject or a system to treat one or more symptoms such as restenosis or a proliferative disorder or a disease. "Prevention" or "preventing" means to administer a composition to a subject or a system at risk for the condition. The condition can be a predisposition to a disease. The effect of the administration of the composition to the subject (either treating and/or preventing) can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur.

II. Devices

Composite prosthetic devices incorporating a system for controlled release of active agents have been developed. The prosthetic devices can be patches or other implants for affixing into or onto the body of a subject. The devices include a support layer bound to a system for the controlled release of one or more active agents. Typically, the system for controlled drug release includes drug-eluting particles, such as microparticles or nanoparticles including the active agent. The composite prosthetic devices include a support layer, particles for delivery of one or more active agent or substance, and a coupling agent for coupling of the particles to the support layer.

A. Patches and Other Implants

Implants are selected based on the use, such as repair of pericardium, dura, cartilage, vasculature, fascia, peritoneum, and other tissues. Exemplary medical implants include patches, such as a vascular patch, a cutaneous patch, a cardiac patch, and a thoracic patch; stents; needles; cannulas; catheters; shunts; balloons; valves; and vascular grafts. Exemplary vascular grafts include autologous, preserved autologous, allogeneic, xenogenic or synthetic grafts. In some embodiments, the implant is a patch, such as a drug eluting patch that elutes one or more active agents. The properties of the material, the mechanical properties, the porosity, and the dimensions are selected or modified as appropriate. Many of these materials are commercially available, and can be readily modified by incorporation of nanoparticles onto and into the material. In some embodiments, the patch is a pericardial patch.

Pericardial patches are useful for the support and repair of pericardial structures, as a patch material for intracardiac defects, great vessel, septal defect and annulus repair, and suture-line buttressing.

1. Naturally-Derived Patches

Bovine pericardium, porcine pericardium and their decellularized derivatives are commonly used as patch prosthetics. Other useful biomaterials include crosslinked collagen membrane, silk, amnion, decellularized bovine inferior vena cava, decellularized extracellular matrix and decellularized human pericardium. These are available commercially, for example, PERI-GUARD® Repair Patch (Baxter), Edwards bovine pericardial patch, CORMATRIX® ECM™ Technology, and LeMaitre Vascular-XenoSure Vascular Patch.

2. Synthetic Patches

Scaffold-type patches are most commonly made of synthetic polymers such as polytetrafluoroethylene (PTFE) and polyesters such as (polyethylene terephthalate) (DACRON®). PTFE is a fluoride resin composed of only carbon and fluoride. Expanded PTFE (ePTFE) has a porous structure with 20 µm to 30 µm fibril distance. An elastomeric coating such as polyurethane can be applied to the outside surface of ePTFE patches to minimize suture hole bleeding. Dacron is a polyester fiber, a condensation polymer of ethylene glycol and terephthalic acid, and shows high tensile strength and resistance to stretching. Dacron is commonly used in a woven or knitted sheet form. Additionally, biomolecules such as collagen can be incorporated into the synthetic scaffold to form collagen-impregnated Dacron or ePTFE patches. Certain functional groups such as amines or carboxylic groups may need to be modified on these materials for covalent conjugation.

Other scaffold-type polymeric materials are used as patches, including polyhydroxyalkanoates such as poly(3-hydroxybutyrate) (P3HB) and poly(4-hydroxybutyrate) (P4HB), poly(e-caprolactone) (PCL), polyhydroxy acids such as poly(lactic acid) (PLA), poly(glycolic acid) (PLGA), and copolymers thereof, polyamides (PA) and their copolymers, and silicone/siloxane elastomers. These scaffolds are commonly generated by electrospinning, and tested for cell compatibility in vitro, and immune response in vitro and in vivo.

Useful materials are reviewed by Ravi, et al., Vascular 17(suppl 1):S45-S54 (2009) and Abruzzo, et al., Int. J. Polymer Sci. Vol. 2014 (2014), Article ID 689390.

Hydrogel-type polymers can also be used. Natural and synthetic hydrophilic polymers can be physically or chemically cross-linked to produce hydrogels. Hydrogel materials include, but are not limited to, hydrophilic polymers such as polyalkylene glycols like poly(ethylene glycol) (PEG) or PLURONIC®s (polypropylene oxide block copolymers), propylene glycol, polyacrylamides, proteins and carbohydates such as hyaluronic acid, dextran, and fibrin, celluloses, and their copolymers.

In some embodiments, patches and other implantable devices include a thin plate or thin sheet of non-biodegradable material. Exemplary materials include, but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the patch or implant may be formed from a cobalt alloy, such as L605 or MP35N®, Nitinol (nickel-titanium shape memory alloy), ABI (palladium-silver alloy), ELGILOY® (cobalt-chromium-nickel alloy), etc. It is also contemplated that the patch or other implantable device may be formed from two or more materials that are laminated together, such as tantalum that is laminated with MP35N®. The patch, or other implant may also be formed from wires having concentric layers of different metals, alloys, or other materials. The aforementioned materials and laminations are intended to be examples and are not intended to be limiting in any way.

3. Combination Patches

Combination patches may be formed of different materials, such as a polymer or ECM scaffold coated with hydrogel, or chemically crosslinked natural materials such as collagen, or having one side of the patch constructed from glutaraldehyde-fixed tissue and the other side constructed from a polymer such as a polyester.

B. Particles

Polymeric nanoparticles can contain one or more polymer, homopolymers or copolymers. The polymer particles are preferably formulated from non-toxic, non-immunological, biocompatible polymers. In preferred embodiments, the polymer is a biodegradable polymer. In cases where the hydrophobic polymer is biodegradable, the polymer degradation profile may be selected to influence the release rate of the active agent in vivo. For example, the polymer can be selected to degrade over a time period from a few days to 2 years, more preferably from a few days to 56 weeks, more preferably to less than 28 weeks.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(hydroxyalkanoates); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof. Preferred biodegradable polymers include poly(lactide-co-glycolide) (PLGA), poly(lactic acid) or polylactide (PLA), poly(ε-caprolactone) (PCL), poly(glycolic acid) or polyglycolide (PGA), poly(D-lactic acid) or poly(D-lactide) (PDLA), poly(L-lactic acid) or poly(L-lactide) (PLLA), polyanhydrides, and poly(ortho esters).

In the preferred embodiment the polymer is a polyhydroxy ester such as poly lactic acid, poly glycolic acid or a copolymer thereof. The ratio of glycolic acid to lactic acid can be optimized to control the rate of degradation.

The polymer can be a polyanhydride. The polyanhydride can be an aliphatic polyanhydride, an unsaturated polyanhydride, or an aromatic polyanhydride. Suitable polyanhydrides are disclosed in U.S. Pat. Nos. 4,757,128, 4,857,311, 4,888,176, and 4,789,724. The polyanhydride can also be a copolymer containing polyanhydride blocks.

In some embodiments, the polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be cross-linked with multivalent ions or polymers.

Micro and nanoparticles designed to deliver cargo such as drugs and antibodies to the vasculature, to vascular smooth muscle cells, or sites or clots or thrombosis are known in the art. See, for example, Wickline, et al., *Arteriosclerosis, Thrombosis, and Vascular Biology*, 26:435-441 (2006), published online (December 2005), and U.S. Published Application Nos. 2002/0168320, 2003/0086867, 2003/0129136, 2004/0058951, 2004/0115192, 2006/0147380, 2006/0239919, 2007/0140965, 2007/0202040, 2007/0258908, 2008/0175792, 2008/0247943, and 2013/0064765.

The molecular weight of the hydrophobic polymer can be varied to prepare polymeric nanoparticles that form particles having properties, such as drug release rate, optimal for specific applications. The polymer can have a molecular weight of about 150 Da to 1 MDa. In certain embodiments, the polymer has a molecular weight of between about 1 kDa and about 100 kDa, more preferably between about 1 kDa and about 50 kDa, most preferably between about 1 kDa and about 25 kDa.

1. Synthesis of Polymeric Nanoparticles

Polymeric nanoparticles can be prepared using synthetic methods known in the art. Representative methodologies for the preparation of polymeric nanoparticles are discussed below. The appropriate route for synthesis of a given polymeric nanoparticle can be determined in view of a number of factors, such as the structure of the polymeric nanoparticle, the identity of the polymers which make up the conjugate, the identity of the active agent, as well as the structure of the compound as a whole as it relates to compatibility of functional groups, protecting group strategies, and the presence of labile bonds.

The particles can be provided as a mixture of two or more different polymeric nanoparticles. For example, particles may be formed from two or more polymeric nanoparticles containing different agents to be release. In other cases, the particles are formed from two or more polymeric nanoparticles containing the same agent, to vary the release rate of the agent.

Typically, the particles have an average particle size of between 1 nm and 1,000 microns, for example, between 1 nm and 100 µm, inclusive, preferably between 10 nm and 500 nm, inclusive. In preferred embodiments, the particles are nanoparticles. The particles can have any shape but are generally spherical in shape.

Particles including active agents encapsulated within, or otherwise associated with the particles preferably have a sufficiently high zeta potential to confer the desired stability to the particle. For example, the describe particles can have a zeta potential that is between incipient and excellent stability, preferably of moderate or good stability. Therefore, in some embodiments, particles have a zeta potential of from approximately from about +/−20 to about +/−60, or more than +/−60.

In some embodiments, the population of particles formed from one or more polymeric nanoparticles is a monodisperse population of particles. In other embodiments, the population of particles formed from one or more polymeric nanoparticles is a polydisperse population of particles. In some instances where the population of particles formed from one or more polymeric nanoparticles is polydisperse population of particles, greater that 50%, 60%, 65%, 70%, 75%, 80%, 85%, 90%, or 95% of the particle size distribution lies within 10% of the median particle size.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. In addition to active agent, pharmaceutically acceptable excipients, including pH modifying agents, disintegrants, preservatives, and antioxidants, can optionally be incorporated into the particles during particle formation.

Particles can include one or more active agents encapsulated within, or otherwise bound to the surface of the particle. The active agents can include, but are not limited to, therapeutic agents, diagnostic agents, markers, dyes and other molecules. In some embodiments, each particle in a plurality of particles includes the same active agent, in the same or different relative amount (weight to weight; wt:wt). In other embodiments, each particle includes two or more active agents in the same or different relative amount (weight to weight; wt:wt).

Typically, nanoparticles encapsulate active agents with a loading efficacy of at least 5%, up to 100%, such as 10%, 20%, 30%, 40%, 50% 60%, 70%, 80%, 90% or more than 90%, such as 99% or approaching 100% efficacy.

Polymeric particles including active agents for delivery to a subject typically have a mean diameter of between 1 nm and 1000 µm, inclusive, preferably between 100 nm and 1000 nm, inclusive. In an exemplary embodiment, nanoparticles having a mean diameter of approximately 370 nm formulated from Poly lactic co-glycolic acid (PLGA) include the therapeutic agent rapamycin. In an exemplary embodiment PLGA/rapamycin particles have a zeta potential of approximately −37.8+/−2.9 mV. As described in the Examples, rapamycin can be loaded into PGLA particles with an efficacy of more than 85%.

C. Active Agents

One or more agents can be released from particles that are covalently bound to a prosthetic patch. The agents may be a therapeutic agent, a prophylactic agent, and/or a diagnostic or imaging agent. Agents may be protein or peptide, carbohydrate or sugar, oligonucleotide, inorganic or small molecule.

In preferred embodiments, the agent is an immunomodulatory or antiproliferative agent. For example, in some embodiments to inhibit restenosis in patch venoplasty or angioplasty, a small molecule immunomodulator such as rapamycin, a peptide or protein such as BMP-7 or a cytokine such as IL-7, a nucleic acid immunoinhibitory molecule, or a combination thereof is encapsulated in particles that are covalently bound to patches. These are released after implantation into the adjacent tissue to prevent neointimal hyperplasia.

Other therapeutic agents that can be encapsulated include antibiotics, antivirals, anti-proliferatives (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, and taxol), antibodies and bioactive fragments thereof (including humanized, single chain, and chimeric antibodies). Small molecule anti-inflammatory agents include steroids such as methyl prednisone and dexamethasone, non-steroidal anti-inflammatory agents such as COX-2 inhibitors, corticosteroid anti-inflammatory agents, gold compound anti-inflammatory agents, immunosuppressive anti-inflammatory and anti-angiogenic agents, salicylate anti-inflammatory agents, ranibizumab, minocycline, and anti-VEGF agents, including aflibercept, and rapamycin.

Exemplary diagnostic materials include paramagnetic molecules, fluorescent compounds, magnetic molecules, and radionuclides.

1. Therapeutic Agents

In some embodiments, the devices include agents that have therapeutic activity, for example, to reduce or prevent one or more undesirable biological processes at or near the site of application. Exemplary therapeutic agents include those which have anti-proliferative activity, anti-neointima activity, and/or anti-inflammatory activity. Exemplary therapeutic agents that can be included within the composite devices include, but are not limited to, antiplatelet agents, anticoagulant agents, anti-inflammatory agents antimicrobial agents, antimetabolic agents, additional anti-neointima agents, additional antiproliferative agents, immunomodulators, antiproliferative agents, agents that affect migration and extracellular matrix production, agents that affect platelet deposition or formation of thrombis, and agents that promote vascular healing and re-endothelialization, such as those and others described in Tanguay et al. *Cardiology Clinics*, 12:699-713 (1994), J. E. Sousa, et al., *Circulation*, 107 (2003) 2274 (Part I), 2283 (Part II), Salu, et al., *Acta Cardiol*, 59 (2004) 51.

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as SIROLIMUS® (Rapamycin), Tacrolimus, Biorest, Mizoribin, Cyclosporin, Interferon-γ 1b, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, and Probucol.

Examples of antiplatelet agents include, but are not limited to, heparin.

Examples of wound healing agents and endothelialization promoters include vascular epithelial growth factor ("VEGF"), 17β-Estradiol, Tkase-Inhibitors, BCP 671, Statins, nitric oxide ("NO")-Donors, and endothelial progenitor cell ("EPC")-antibodies.

In some embodiments, the composite prosthetic patches with covalently bound particles for controlled drug release include antibodies, or antigen binding fragments of antibodies. The antibodies can be those that specifically bind one or more molecules in a location close to the site of the patch, or at a distance from the site of the patch. Antibodies can include an antigen binding site that binds to an epitope on a target molecule, such as a protein. In an exemplary embodiment, antibodies associated with particles that are covalently bound to a prosthetic patch specifically inhibit the function of one or more target molecules by binding directly to the target molecule, its ligands or its accessory molecules. Any specific antibody can be used in the compositions.

Various types of antibodies and antibody fragments can be used in the compositions, including whole immunoglobulin of any class, fragments thereof, and synthetic proteins containing at least the antigen binding variable domain of an antibody. The antibody can be an IgG antibody, such as IgG1, IgG2, IgG3, or IgG4. An antibody can be in the form of an antigen binding fragment including a Fab fragment, F(ab')2 fragment, a single chain variable region, and the like. Antibodies can be polyclonal or monoclonal (mAb). Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind a target antigen and/or exhibit the desired biological activity (U.S. Pat. No. 4,816,567; and Morrison, et al., *Proc. Natl. Acad. Sci. USA*, 81: 6851-6855 (1984)). Antibodies can also be modified by recombinant means, for example by deletions, additions or substitutions of amino acids, to increase efficacy of the antibody in mediating the desired function. Substitutions can be conservative substitutions. For example, at least one amino acid in the constant region of the antibody can be replaced with a different residue (see, e.g., U.S. Pat. No. 5,624,821; U.S. Pat. No. 6,194,551; WO 9958572; and Angal, et al., *Mol. Immunol.* 30:105-08 (1993)). In some cases changes are made to reduce undesired activities, e.g., complement-dependent cytotoxicity. The antibody can be a bi-specific antibody having binding specificities for at least two different antigenic epitopes. In one embodiment, the epitopes are from the same antigen. In another embodiment, the epitopes are from two different antigens. Bi-specific antibodies can include bi-specific antibody fragments (see, e.g., Hollinger, et al., *Proc. Natl. Acad. Sci. U.S.A.*, 90:6444-48 (1993); Gruber, et al., *J. Immunol.*, 152:5368 (1994)).

Antibodies can be generated by any means known in the art. Exemplary descriptions means for antibody generation and production include Delves, Antibody Production: Essential Techniques (Wiley, 1997); Shephard, et al., Monoclonal Antibodies (Oxford University Press, 2000); Goding, Monoclonal Antibodies: Principles And Practice (Academic Press, 1993); and Current Protocols In Immunology (John Wiley & Sons, most recent edition). Fragments of intact Ig molecules can be generated using methods well known in the art, including enzymatic digestion and recombinant means.

In some embodiments, the composite prosthetic patches with covalently bound particles for controlled drug release include one or more functional nucleic acids. Therefore, composite prosthetic patches with covalently bound particles for controlled release of functional nucleic acids that inhibit the transcription, translation or function of a target gene product are described. Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules. Functional nucleic acid molecules can interact with any macromolecule, such as DNA, RNA, polypeptides, or carbohydrate chains. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore the composite prosthetic patches with covalently bound particles for controlled release can include one or more functional nucleic acids designed to reduce expression or function of a target protein. Methods of making and using vectors for in vivo expression of the disclosed functional nucleic acids such as antisense oligonucleotides, siRNA, shRNA, miRNA, EGSs, ribozymes, and aptamers are known in the art.

In certain embodiments, composite prosthetic devices include particles eluting active agents in an amount effective to treat or prevent one or more diseases or disorders that are known to occur as a side-effect of the implantation of the pericardial patch. In some embodiments, the pericardial patch is a bovine or porcine pericardial patch. Therefore, in some embodiments, the composite prosthetic pericardial patch includes particles that deliver one or more therapeutic agents in an amount effective to treat or prevent one or more side-effects associated with implantation of bovine pericardium or porcine pericardium into a human subject. Therefore, in some embodiments, the composite prosthetic pericardial patch includes particles that deliver one or more therapeutic agents to treat or prevent accelerated calcific infiltration, for example, in patients with high calcium metabolic activity (e.g., children). In some embodiments, the composite prosthetic pericardial patch includes particles that deliver one or more therapeutic agents to treat or prevent epicardial inflammatory reactions and/or adhesion of the pericardium to the heart, prevent formation of pericardial adhesions, prevent calcification of the arteries, prevent inflammatory processes at or near the site of implantation, prevent formation of fibrous tissue in the arteries at or near the site of implantation, or combinations thereof.

In other embodiments, the composite prosthetic pericardial patch includes particles that deliver one or more active agents that enhance or prolong the lifespan or usefulness of the patch itself. For example, the particles can deliver one or more active agents that reduce or prevent deterioration of implanted bovine pericardium, prevent focal degradation of implant collagen, prevent active phagocytosis and prevent chronic inflammatory infiltrate and the formation of giant cell infiltrate at the interface between the implant and surrounding host tissues, or combinations thereof.

In certain embodiments, agents that are associated with particles that are covalently bound to a prosthetic patch include immunomodulatory agents. Exemplary immunomodulatory agents include rapamycin, TGF-β1, or TGF-β1 Inhibitors.

i. Rapamycin

In some embodiments, the composite prosthetic patches with covalently bound particles for controlled drug release include rapamycin (also known as SIROLIMUS®). In some embodiments, the composite prosthetic patches can include bound particles having rapamycin encapsulated and/or associated with nanoparticles or microparticles at the surface of the device. Therefore, in certain embodiments composite prosthetic patches with covalently bound particles release rapamycin, or a derivative prodrug or functional analog of rapamycin.

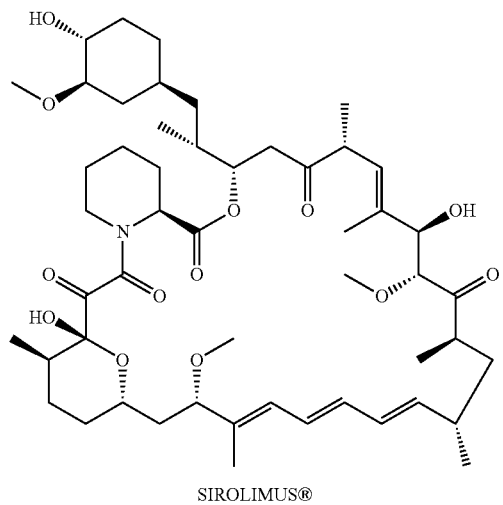

Formula I

SIROLIMUS®

SIROLIMUS® is a macrolide compound produced by the bacterium *Streptomyces hygroscopicus* and was first isolated in 1972, from samples of *Streptomyces hygroscopicus* found on Easter Island. SIROLIMUS® has Empirical Formula $C_{51}H_{79}NO_{13}$, and a molecular weight of 914.17 Da (CAS Number: 53123-88-9). It is thought SIROLIMUS® inhibits activation of T cells and B cells by reducing the production of interleukin-2 (IL-2).

SIROLIMUS® is a member of the class of compounds that inhibit the mechanistic target of rapamycin (mTOR) molecule (i.e., mTOR inhibitors). SIROLIMUS® (rapamycin) has been shown to have immunosuppressant functions through regulation of T cell activities and has been shown to be useful in preventing the rejection of organ transplants, as well as inhibiting neointimal hyperplasia in arterial and vein grafts (Suzuki, et al., *Circulation* 104, 1188-1193 (2001); Araki, et al., *Nature,* 460, 108-112 (2009)).

Variants, derivatives and functional analogues of rapamycin are known, including the structural analog everolimus (also known under the trade names ZORTRESS®, CERTICAN®, AFINITOR®, and VOTUBIA®) temsirolimus (prodrug analog of rapamycin, also known as CCI-779), as well as deforolimus or ridaforolimus. Therefore, in certain embodiments composite prosthetic patches with covalently bound particles release one or more variants, derivatives and functional analogues of rapamycin, or combinations of these with rapamycin.

Rapamycin is commercially available from multiple sources, including as a 1 mg/ml solution from Sigma-Aldrich (Product No. S-015).

ii. Transforming Growth Factor (TGF)

In some embodiments, the composite prosthetic patches with covalently bound particles for controlled drug release include cytokines such as transforming growth factors (also known as TGFs). In some embodiments, the composite prosthetic patches can include bound particles having one or more TGFs encapsulated and/or associated with nanoparticles or microparticles at the surface of the device. Therefore, in certain embodiments composite prosthetic patches with covalently bound particles release TGFs, or combinations of TGFs and other cytokines.

Transforming growth factor beta (TGF-beta) is a member of a large family of pleiotropic cytokines that are involved in many biological processes, including growth control, differentiation, migration, cell survival, adhesion, and specification of developmental fate, in both normal and diseased states. TGF-beta superfamily members signal through a receptor complex comprising a type II and type I receptor, both serine/threonine kinases. The transforming growth factor-β (TGF β) ligand is one of the cytokines that is important in regulating diverse cellular functions, including proliferation, angiogenesis, differentiation, inflammation and wound healing (Akhurst and Hata, *Nat Rev Drug Discov*, 11:790-811 (2012); Meng, et al., *Nat Rev Nephrol.* 12:325-338 (2016)). TGF β members like TGF β1, TGF β2 and TGF β3 are associated with aneurysm and other cardiovascular diseases (Lindsay, et al., *Nature.* 473:308-316 (2011); Loeys, et al., *N Engl J Med.* 355:788-798 (2006)). Loss of function mutations in TGF β2 and TGF β3 cause aortic aneurysms and dissections (Lindsay, et al., *Nat Genet.* 44:922-927 (2012); Bertoli-Avella, et al., *J Am Coll Cardiol*, 65:1324-1336 (2015)) In some embodiments, the composite prosthetic patches with covalently bound particles for controlled drug release include TGF β1, or TGF β2, or TGF β3, or combinations of more than one of these.

a. TGF-β1

Transforming growth factor beta 1 or TGF-β1 is a polypeptide member of the transforming growth factor beta superfamily of cytokines. It is a secreted protein that performs many cellular functions, including the control of cell growth, cell proliferation, cell differentiation and apoptosis.

Studies have shown that TGF-β signaling dysregulation is associated with an increasing number of vascular pathologies (Goumans, et al., *Cell Res*, 19:116-127(2009); ten Dijke and Arthur, *Nat Rev Mol Cell Biol*, 8:857-869 (2007)). TGF-β signaling pathway also plays an important role in aneurysm formation. Gillis, et al., *Circ Res*, 113:327-340 (2013); Loeys, et al., *N Engl J Med*, 355:788-798 (2006). In a mouse model, neutralized TGF-β enhances aneurysm formation and rupture (Chen, et al., *PLoS One.* 11:e0153811 (2016)) on the contrary, in a rat abdominal aortic aneurysm model, increase TGF β1 stabilized aortic dilation (Dai, et al., *Circulation*, 112:1008-1015 (2005); Losy, et al., *J Vasc Surg.* 37:1301-1309 (2003); and Wang, et al., *J Clin Invest*, 120:422-432(2010)). TGF-β type receptors (TGFBR1 and TGFBR2) mutations can promote aortic aneurysm formation, both in mice and human (Yang, et al., *Sci Rep.* 6:35444(2016); Li, et al., *J Clin Invest*, 124:755-767 (2014); Stheneur, et al., *Hum Mutat.* 29:284-295 (2008)). Smad2 mediates TGF-β signals and mutations in smad2 are associated with human artery aneurysm formation and dissecctions. Nakao et al, *EMBO J.* 16:5353-5362 (1997); Micha et al., *Hum Mutat*, 36:1145-1149 (2015); Loinard et al., *Circ Cardiovasc Genet.* 7:799-805 (2014); Gomez et al., *Circ Res*, 113:881-890 (2013)).

Using nanotechnology to deliver TGF β has been used in animal models, and shows promising results (Zhou, et al., *Biomaterials*, 34:8269-8278 (2013); Xu, et al., *ACS Nano*, 8:3636-3645 (2014)). In a rat abdominal aortic aneurysm model, virus-mediated overexpression of TGF β1 increased endogenous TGF β1 levels, stabilized aortic dilation and attenuated vascular degeneration (Dai et al., *Circulation.* 112:1008-1015 (2005)). Seeding of vascular smooth muscle cells can promote healing and stabilization of aneurysms and this effect is mediated by the expression of TGF β1 from the smooth muscle cells. TGF β can also protect against the inflammatory progression of aortic aneurysms in mice. Overexpression of TGF β1 can also prevent aortic dilation in apolipoprotein E-Null mice (Frutkin, et al., *Arterioscler Thromb Vasc Biol.* 29:1251-1257 (2009)).

In some embodiments, the composite prosthetic patches with covalently bound particles release TGF-beta 1 (TGF-β1). Variants, derivatives and functional analogues of TGF-β1 are known. Therefore, in certain embodiments composite prosthetic patches with covalently bound particles release one or more variants, derivatives and functional analogues of TGF-β1, or combinations of these with TGF-β1. Human TGF-β1 is commercially available from multiple sources, including as a 5 µg lyophilized powder from Miltenyi Biotec (Product No. 130-095-067).

b. TGF-β1 Inhibitors

In other embodiments, composite prosthetic patches with covalently bound particles release one or more molecules that inhibits, reduces or prevents the function of TGF-β1, such as a TGF-β1 inhibitor. TGF-β1 inhibitors can act directly upon TGF-β1, or they can act on one or more of the receptors or ligands of TGF-β1, to reduce or prevent one or more of the biological activities of TGF-131. For example, in some embodiments, TGF-β1 inhibitors inhibit the production, expression or function of one or more TGF-β-mediated growth factors. An exemplary inhibitor of TGF-β1 is SB 431542 (CAS No, 301836-41-9).

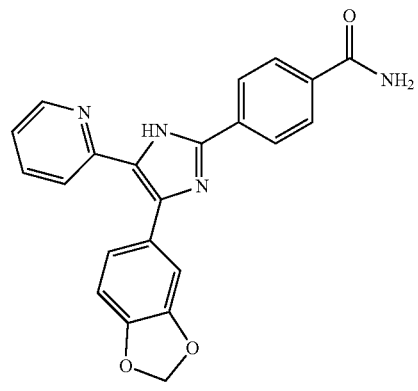

Formula II

SB431542

The small molecule inhibitor SB-431542 has been identified as an inhibitor of the TGF-beta type I receptor, activin receptor-like kinase (ALK)5 (Inman, et al., *Mol Pharmacol.* 62(1):65-74 (2002)). SB-431542 inhibits ALK5 and also the activin type I receptor ALK4 and the nodal type I receptor ALK7, which are very highly related to ALK5 in their kinase domains. SB 431542 inhibits both TGF-β1-induced collagen Iα1 and PAI-1 mRNA with IC50 of 60 nM and 50 nM, respectively, and inhibits production of TGF-β1-induced fibronectin mRNA and fibronectin protein with IC50 of 62 nM and 22 nM, respectively. SB 431542 blocks multiple TGF-β-mediated growth factors, including PDGF-A, FGF-2 and HB-EGF, leading to an increase in proliferation of MG63 cells. SB 431542 also inhibits TGF-β-induced c-Myc and p21 WAF1/CIP1, and significantly suppresses TGF-β-induced G1 arrest, leading to accumulation of cells in the S phase of the cell cycle in FET, RIE, and Mv1Lu cells. SB 431542 also inhibits TGF-β-induced epithelial to mesenchymal transition (EMT) in NMuMG and PANC-1 cells. SB 431542 significantly elevates the expression of CD86 in BM-DCs and that of CD83 within CD11c+ cells suppressed by TGF-β. SB 431542 is able to induce NK activity through functional maturation and IL-12 production of human DCs.

SB 431542 is commercially available from multiple sources, including as a 5 mg powder from Sigma Aldrich (Product No. SB 431542; SB 431542 hydrate).

2. Other Active Agents

Besides coronary applications, drugs and active agents may be incorporated into the composite prosthetic device for controlled release of active agents for use in other indications. Therefore, in some embodiments, the devices include other active agents, such as drugs, diagnostic agents, targeting agents, or agents that can be used to label/image one or more cells or tissues or synthetic structures in vivo. For example, in urological applications, antibiotic agents may be incorporated into the device, for the controlled release of drugs to prevention of infection. In gastroenterological and urological applications, active agents may be incorporated into the devices for the controlled release of agents for local treatment of carcinoma.

It may also be advantageous to incorporate active agents including contrast agents, radiopaque markers, or other additives to allow composite prosthetic devices to be imaged in vivo for tracking, positioning, and other purposes. Such additives could be added to the surface of the composite device, or contained within the delivery system, for example, within or on nanoparticles or microparticles. Exemplary agents for this purpose include silver, iodine and iodine labeled compounds, barium sulfate, gadolinium oxide, bismuth derivatives, zirconium dioxide, cadmium, tungsten, gold tantalum, bismuth, platinum, iridium, and rhodium. These agents may be, but are not limited to, micro- or nano-sized particles or nano particles. Radio-opacity may be determined by fluoroscopy or by X-ray analysis.

D. Crosslinking Agent

In preferred embodiments, particles containing one or more active agents are covalently bound to prosthetic patches via crosslinking agents. Crosslinking agents are categorized by their chemical reactivity, spacer length, and materials.

TABLE 1

Reactive groups of crosslinking agents
TABLE 1
REACTIVE GROUP OF CROSSLINKING AGENTS

| Reactivity Class (Reactive group) | Chemical Group of Crosslinking Agent |
|---|---|
| Carboxyl-to-amine Amine | Carbodiimide (e.g. EDC) NHS ester Imidoester Pentafluorophenyl ester Hydroxymethyl phosphine |
| Sulfhydryl | Maleimide Haloacetyl (Bromo- or Iodo-) Pyridyldisulfide Thiosulfonate Vinylsulfone |
| Aldehyde (i.e. oxidized sugars, carbonyls) | Hydrazide Alkoxyamine |
| Photoreactive groups (i.e. nonselective, random insertion) | Diazine Aryl Azide |
| Hydroxyl (non-aqueous) | Isocyanate |

TABLE 2

Hetero-bi-functional cross-linkers
TABLE 2
HETERO-BIFUNCTIONAL CROSSLINKER

| Linker | Reactive Toward | Advantages | Spacer Arm Length after cross-linking |
|---|---|---|---|
| SMPT | Primary amines Sulfhydryls | Great stability | 11.2 A |
| SPDP | Primary amines Sulfhydryls | Thiolation Cleavable cross-linker | 6.8 A |
| LC-SPDP | Primary amines Sulfhydryls | Extended spacer arm | 15.6 A |
| Sulfo-LC-SPDP | Primary amines Sulfhydryls | Extended spacer arm; water soluble | 15.6 A |
| SMCC | Primary amines Sulfhydryls | Stable maleimide reactive group; | 11.6 A |
| Sulfo-SMCC | Primary amines Sulfhydryls | Stable maleimide reactive group; water soluble | 11.6 A |
| MBS | Primary amines Sulfhydryls | | 9.9 A |
| Sulfo-MBS | Primary amines Sulfhydryls | Water soluble | 9.9 A |
| SIAB | Primary amines Sulfhydryls | | 10.6 A |
| Sulfo-SIAB | Primary amines Sulfhydryls | Water soluble | 10.6 A |
| SMPB | Primary amines Sulfhydryls | Extended spacer arm | 14.5 A |
| Sulfo-SMPB | Primary amines Sulfhydryls | Extended spacer arm; water soluble | 14.5 A |
| EDC/Sulfo-NHS | Primary amines Carboxyl groups | | 0 |
| ABH | Carbohydrates Nonselective | Reactive with sugar groups | 11.9 A |

1. Oligomers or Macromolecules

In some embodiments, the particles are covalently bound via degradable crosslinkers in response to the biological environment, such as enzymes and pH. These degradable crosslinkers can be composed of peptides. In further embodiments, the linkers between particles and prosthetic patches are macromolecules including, but not limited to, PEG and bromomethylated poly(ether ketone).

E. Composite Devices

The composite devices can be sized and formulated according to the needs of the subject, and the disease or condition to be diagnosed, prevented or treated. Factors including the density of particles on the surface, the porosity of the support structure, the size, composition and zeta potential of the particles and the overall physical dimensions of the device impart the biological function of the device.

1. Surface Density of Particles

In some embodiments, composite prosthetic devices include nanoparticles or microparticles coupled to the support or surface layer at a defined surface density. For example, in some embodiments, the particles containing one or more active agents are coupled to the support or surface layer at or approaching the maximum surface density possible for the available surface area of the support in relation to the size of the particles. For example, when an excess of particles is used to in the conjugation reaction, the limiting factor determining the surface density will the availability of substrate and/or stearic hindrance on the support surface. In other embodiments, the particles containing one or more active agents are coupled to the support or surface layer to achieve a surface density that defines the maximum dose or amount of the active agent that is to be released. For example, in certain embodiments, the surface density of the bound particles is a function of the total amount of particles within the conjugation reaction, relative to an excess amount of substrate or surface area available. Therefore, in some embodiments, the surface density of particles coupled to the support or surface layer limits or determines the dosage of the active agent. Typically, the density of particles that are bound to the surface of the device is directly proportional to the total amount of particles, so that the density is linearly proportional to particle number to the point of saturation.

In some embodiments, the particles are present at the surface of the device at a density of between 0.01 and 1,000 $\mu g/mm^2$. In an exemplary embodiment, nanoparticles are conjugated to the device at the surface of the device at a density of approximately 2.67 $\mu g/mm^2$. In some embodiments, the particles are bound to prosthetic patches at a density between 0.01 $\mu g/mm^2$ to 1000 $\mu g/mm^2$, encapsulating between 1 ng and 1 $\mu g$ of the agent per 1 $\mu g$ of particles, resulting in the delivery of the agent between 10 $ng/mm^2$ and 10 $mg/mm^2$ from prosthetic patches. The particle bound patches can release agents over time with a controlled rate. For example, the one more agent(s) encapsulated in the particles can be released over a period of time ranging from between one hour and a few weeks.

The amount of active agent present within or on the composite device, and the penetration of the active agents throughout the device and surrounding tissue can be adjusted, by changing the formulation or the support or patch. In this way the amount of active agents locally release at the site of implantation can be carefully controlled. The amount and localization of attachment of delivery systems, such as particles, to the patch surface can also be varied by varying the type and density of attachment and coupling or cross-linking agents, such as those described above, presented on the surface of the device.

2. Porosity

The composite prosthetic devices can be designed to have a defined porosity, to admit or prevent passage of one or more substances through the device. For example, in some embodiments the devices prevent passage of fluids through the device. In other embodiments, the devices are porous, admitting passage of fluids into and throughout the device. The devices can have pore size between 0.1 nm and 100 $\mu m$, inclusive, for example, between 1 nm and 1 $\mu m$, inclusive.

In some embodiments the devices have a pore size sufficient to allow passage of the associated active agent through the device 3. Physical Dimensions The composite prosthetic devices can be designed to have a size and shape appropriate for the intended use of the device. In some embodiments, the device is shaped to conform to fit within the vascular conduit. In an exemplary embodiment, the device is the size of a surgical site or wound, for example, a vascular wound or injury. In some embodiments, the dimensions (e.g., length and width) determine the total surface area of the device and therefore determine the amount of nanoparticles that can be bound to the device. In some embodiments, the thickness (e.g., height) of the device determines the permeability of the device, and the ability of the device to elute or retain one or more molecules or cells. In preferred embodiments, the device is sized suitable for application/implantation to a subject at the desired location in vivo, for example, at the site of a surgery, such as the pericardium, a blood vessel, the brain, breast tissue, and the site of a hernial reconstruction or repair. The device can have dimensions (i.e., width, height, length) of between 0.01 mm and 300 mm, preferably between 0.1 mm and 10 mm in any dimension. The device can be shaped (i.e., cut, molded, folded or positioned) to the desired shape and form. In exemplary embodiments, the device is a patch shaped to have the dimensions 3 mm long×1.5 mm wide×0.6 mm in height, or 7 mm long×5 mm wide×1 mm in height.

Typically, the total amount of an active agent within the composite prosthetic device bound to particles is determined as a function of the total amount (weight) of active agent per amount (unit weight) of particles bound to the device, wherein the amount of particles bound to the device is determined from the surface density of the particles on the device.

4. Amounts of Active Agents

In some embodiments, the particles bound to the composite prosthetic devices contain a specific amount of one or more active agents, according to the intended use of the device. The amount of the active agent, as well as the timing of release of the active agent, and the continuity and rate of release of the active agent contained within the particles can each be independently varied according to the needs of the intended recipient. Therefore, in some embodiments, the composite prosthetic device contains particles including an amount of active agent for release over a defined period of time. In some embodiments, the composite prosthetic device includes two or more different types of particles, each type containing the same or different amounts of different active agents. In an exemplary embodiment, a composite prosthetic device includes two or more different types of particles containing the same or different active agent in different amounts, for in vivo delivery to a subject at different times following implantation of the device into the subject. For example, the device can include particles designed to degrade completely within a short period of time and deliver a bolus of one active agent shortly after implantation. The same composite device can also include nanoparticles including the same or different active agent, designed to degrade more slowly and deliver the active agent to the subject at a constant rate over a defined period of time, such as 1-31 days following implantation. In an exemplary embodiment, the device delivers an active agent at a constant rate for a period of 21 days following implantation in vivo. Therefore, in some embodiments, composite prosthetic devices have bound thereto two or more different types of nanoparticles, where the relative amounts (i.e., ratio) of the two or more different types of nanoparticles to one another is designed to provide a desired regimen of delivery of one or more active agents to a subject. In preferred embodiments, composite prosthetic devices having bound thereto two or more different types of nanoparticles for delivery of the same or different therapeutic agent to a subject over two or more distinct time frames include a therapeutically effective amount of each therapeutic agent. For example, in preferred embodiments a composite prosthetic device having bound thereto one or more types of nanoparticles include one or more therapeutic agents in an amount sufficient to treat, inhibit, or alleviate one or more symptoms of a disease or disorder in the subject, or to otherwise provide a desired pharmacologic and/or physiologic effect.

In particular embodiments, the composite prosthetic devices having bound thereto one or more types of nanoparticles include an amount of therapeutic agent for delivery effective to reduce or prevent neointima at the site of vascular injury or surgery in the subject. For example, the nanoparticles bound to the device can include an amount of active agent(s) for delivery effective to reduce proliferation, migration, or a combination thereof of smooth muscle cells from the media layer into the intima. The amount can be effective to prevent, reduce, or inhibit the rise or appearance of fused intima and media. The amount can be effective to reduce proliferation, migration, or a combination thereof of intima smooth muscle cells. In some embodiments, the amount is effective to reduce or inhibit proliferation of smooth muscle cells to a greater extent than reducing or inhibiting proliferation of endothelial cells. In some embodiments, the amount is effective to reduce or inhibit proliferation of smooth muscle cells without substantially reducing or inhibiting proliferation of endothelial cells.

The precise amount of active agent for delivery will vary according to a variety of factors such as subject-dependent variables (e.g., age, immune system health, etc.), the disease, and the treatment being effected. The ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. The total amount of active agent encapsulated by all of the particles bound to a device can be between 0.1 ng and 1,000 µg, preferably between 1 ng and 100 ng, inclusive.

III. Methods of Making the Composition

In some embodiments, the patches are commercially available. In other embodiments, the naturally-derived patches are made via harvesting, decellularization, fixing, coating with optionally added bioactive signals and sterilization. These naturally-derived patches have relatively high tensile strength.

In further embodiments, synthetic patches can be made by blending, mixing, or crosslinking of polymeric materials in a mold or coated, sprayed or electrospun into a film or a sheet.

A. Methods of Making Particles.

The particles described herein can be prepared by a variety of methods.

1. Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. The nanoparticles with different sizes and morphologies can be obtained by this method. This method is useful for relatively stable polymers like PBA, polyesters and polystyrene.

2. Interfacial Polycondensation

Interfacial polycondensation is used to encapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid nanoparticles containing core material.

The solvent evaporation process can be used to entrap a liquid core material in a polymer such as PBA, PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a nanoparticles composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of microparticles or nanoparticles that have a more optimized release of the encapsulated material.

4. Hot Melt Microencapsulation.

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting particles are washed by decantation with petroleum ether to give a free-flowing powder. Particles with sizes between 0.5 to 1000 microns are obtained with this method. The external surfaces of spheres prepared with this technique are usually smooth and dense. This procedure is used to prepare particles made of PBA, polyesters and polyanhydrides. This method is limited to polymers with molecular weights between 1,000 and 50,000.

5. Solvent Removal Microencapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid particles containing core material.

6. Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

7. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

8. Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

9. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

10. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

B. Methods of Covalent Binding of Particles to Patches

In preferred embodiments, particles are conjugated to the surface and within the body of one or more regions of the patch.

In some embodiments, the reactive groups are present in both the patches and the particles, resulting in direct activation of conjugation. In one aspect, the conjugation may be activated by use of photons at different wavelengths in the presence or absence of a photo-activator. In another aspect, zero length crosslinking agents such as EDC/NHS are added and the conjugation reaction is carried out at an appropriate agitation speed, temperature and pressure.

In further embodiments, the reactive groups are not present or crosslinkers with certain features are required for the composition. In one aspect, the reactive chemical groups are modified at the surface and/or the body of either the patches or the particles, or both. Subsequently, reactive groups can be activated. In another aspect, peptidyl or macromolecule crosslinkers with appropriate chemical reactivities can be used to conjugate the particles to the patches.

IV. Methods of Using the Composition

Methods of using composite prosthetic patches with covalently bound particles for controlled drug release are provided. The methods can include implanting within, or otherwise administering to a subject one or more composite prosthetic devices with covalently bound particles for the controlled release of an effective amount of one or more active agents to prevent, reduce, or inhibit the expression or function of a target molecule in the subject; or to prevent, reduce, or inhibit one or more symptoms of a disease or disorder in the subject, or a combination thereof. In an exemplary embodiment, methods of using composite prosthetic patches with covalently bound particles for controlled drug release to prevent neointima formation following insertion or implantation of the device or graft into the subject are provided. Typically the subject is a human, such as a human in need of treatment for, or having been diagnosed with a disease or disorder, or as having an increased risk of developing a disease or disorder.

A. Methods of Administration

Typically, the composite prosthetic devices having particles bound thereto for delivery of active agents are implanted within a subject during standard surgical procedures, for example, at or within the site of the surgery. The composite prosthetic device can be inserted into the subject transiently, or implanted permanently within the subject. In an exemplary embodiment, the composite device may be inserted into a restricted vessel, prior to, during or after a procedure to cut, remove, or otherwise damage a section of the vessel. For example, in some embodiments, the composite device is implanted into a restricted vessel during a procedure whereby the restricted vessel is widened. In an exemplary embodiment, if a composite prosthetic device having particles bound thereto for delivery of active agents is inserted into a human artery during a procedure for the elimination of an arteriosclerotic stenosis, the device can prevent intimal hyperplasia and renewed stenosis at the site of implantation.

Composite prosthetic patches including bound particles can be used in place of conventional prosthetic devices, and can be inserted or implanted into a subject in need using techniques known in the art. In some embodiments, the patches with bound particles encapsulating one or more active agents can be sutured at the periphery onto the defective part of a patient. In another embodiment, the patches can be placed over the defective part of a patient and a light vacuum is applied or formed between the plastic and the skin, keeping the prosthesis in place.

In further embodiments, the patches can be adhere on the defective part of a patient. Synthetic or natural glue may be used, including, but not limited to, fibrin glue.

B. Disorders and Diseases to be Treated

In preferred embodiments, composite prosthetic patches are effective to reduce, inhibit, or delay one or more biological processes, symptoms of a disease, disorder or condition in a subject. The composite prosthetic patches with covalently bound particles for controlled drug release have a wide variety of therapeutic and prophylactic uses, for example, they can be used to treat or prevent vascular proliferative disorders following injury or various surgical procedures, inflammatory and/or fibrotic diseases. Methods of using composite prosthetic patches with covalently bound particles for controlled drug release for treating a disease characterized by the presence of excessive inflammation, undesirable proliferation or deposition of extracellular matrix or cells, or fibrosis are described. Methods of using one or more composite prosthetic patches with covalently bound particles for controlled drug release for therapy, for example, for treating diseases resulting from aberrant, excessive or otherwise undesirable vascular proliferation are also provided.

In certain embodiments, the composite prosthetic device is a pericardial patch for use as a prosthesis for surgical repair. Exemplary uses in surgical repair include soft tissue deficiencies such as muscle flap reinforcement, defects of the abdominal wall, defects of the thoracic wall, repair of tears and hernias, and gastric binding. Methods of repairing hernias using the composite prosthetic pericardial patches are provided. Hernias that can be repaired by the described methods include diaphragmatic hernias, femoral hernias, incisional hernias, inguinal hernias, lumbar hernias, paracolostomy hernias, scrotal hernias, and umbilical hernias. Other surgical procedures that can benefit from implantation of composite pericardium patches include cardiovascular surgeries, such as closure of intracavitary defects, enlargement of the right ventricular outflow tract and aortic annulus during valve replacement, treatment of aortic and left ventricular aneurysms, atrial and ventricular repair, Mustard surgery, and peripheral arterioplasties; thoracic surgeries, including closure of bronchial stumps and diaphragmatic hernias, treatment of chest wall defects (both congenital and traumatic); urologic surgeries, such as cytoplasty and ureteroplasty; and neurosurgery. For example, in some embodiments, composite pericardium patches including particles for drug delivery can be used to replace the dura mater of the brain.

Methods of preventing, suppressing or treating one or more symptoms of a disorder, disease or condition may include administering to a subject in need thereof a surgical size unit of the prosthetic patches covalently modified with particles encapsulating the one or more agent(s); delivering an effective amount of one or more agent(s) to target tissues, such as cardiovasculature, diaphragm, femur and skin; wherein the one or more agent(s) are released from the particles at the target tissues.

1. Immune Modulation

In some embodiments, the methods are directed to preventing, suppressing or treating symptoms relating to the undesirable effects of the subject's immune system in response to injury, trauma, disease, or the implantation of the device itself. Therefore, in certain embodiments, composite prosthetic devices include particles eluting active agents are used in a method of treating, preventing or reducing one or more diseases or disorders that are known to occur as a side-effect of the implantation of the prosthetic device into a subject. Exemplary immune-relate diseases and disorders include restenosis, neointimal hyperplasia, scarring and over-proliferation of cells. Composite prosthetic patches with covalently bound particles for controlled drug release can be used to alter the biological functions of immune effector cells, including, but not limited to, macrophage, platelet, and natural killer cell function, creating a pro-regenerative immune environment. Methods of using composite prosthetic patches with covalently bound particles for controlled drug release including, but not limited to, cytokines and immunomodulatory drugs such as rapamycin can be used to modulate the immune response. In some embodiments, the methods facilitate vascular neotissue formation, inhibit the formation of neointima and improve vascular patency, for example, following vascular surgery. Additionally, composite prosthetic patches with covalently bound particles for controlled drug release can have broader implications for promoting tissue regeneration, improving wound healing, and modulating the foreign body response. Thus, methods of using composite prosthetic patches with covalently bound particles for controlled drug release as an adjunct to regenerative medicine applications are also described. Preferably, administering or implanting the composite prosthetic patches with covalently bound particles for controlled drug release promotes normal healing and prevents undesirable proliferative processes, for example, promoting healing and preventing intimal hyperplasia after vascular surgery.

The methods can also prevent or treat diseases resulting from excessive fibrosis, for example fibrotic diseases of the liver, lung or heart. Finally, methods of controlled drug release according to the composite prosthetic patches with covalently bound particles can result in immune modulation that alters the foreign body reaction and promotes integration but blocks encapsulation of bio-prostheses, thus improving function and longevity of devices such as pacemaker or nerve stimulators or integration of replacement heart valves or artificial joints.

i. Vascular Proliferative Disorders

In some embodiments, the composite prosthetic patches with covalently bound particles for controlled drug release can be used to treat or prevent vascular proliferative disorders. Examples of such disorders include, but are not limited to, vascular proliferation involved in atherosclerosis, vascular proliferation following intravascular device implantation, vascular proliferation at the site of vascular anastamosis as generally occurs following revascularization procedure or A-V shunting, vascular proliferation following carotid endarterectomy, and transplant vasculopathy.

Methods of treating or preventing vascular proliferative disorders by administration of one or more composite prosthetic patches with covalently bound particles for controlled drug release are provided. The methods typically reduce or inhibit the infiltration of macrophage cells, or the conversion of macrophage cells from M1 to M2 phenotype, or both, compared to a control. In some embodiments, the methods reduce or inhibit proliferation of macrophage cells without reducing or inhibiting vascular neotis sue development. A subject can have stenosis, restenosis or other vascular proliferation disorders, or be identified as being at risk for restenosis or other vascular proliferation disorders, for example subjects who have undergone, are undergoing, or will undergo a vascular trauma, angioplasty, surgery, or transplantation arteriopathy, etc. Diseases, disorders and conditions that can be treated using the disclosed compositions are discussed in more detail below.

ii. Vascular Injury or Surgery

In some embodiments, one or more composite prosthetic patches with covalently bound particles for controlled drug release is applied before, at the time of, or following a vascular trauma or a surgical procedure.

Vascular injury triggers a cascade of events that includes endothelial denudation or dysfunction, inflammation, as well as activation and proliferation of vascular smooth muscle cells (VSMC). Multiple growth factors and cytokines are released by dysfunctional endothelial cells, inflammatory cells, platelets and VSMCs. These growth factors and cytokines mediate chemo-attraction, cell migration, proliferation, apoptosis and matrix modulation, and are implicated in a number of vascular proliferative disorders.

Vascular proliferative diseases and disorders can be initiated by mechanical, biochemical or immunological injury to blood vessel walls. Typical vascular trauma include those associated with both blunt and penetrating injuries including, but not limited to, lacerations, puncture wounds, crush injuries, gunshot wounds, knife wounds, occupational injuries, falls, and motor vehicle accidents, as well as medical interventions, such as surgery or angioplasty.

In some embodiments, the subject has undergone, is undergoing, or will undergo a surgery. Surgeries can include invasive, minimally invasive, or percutaneous surgery. For example, in some embodiments the subject is having surgery to treat or repair abdominal aortic aneurysm, carotid stenosis, varicose veins, peripheral arterial occlusive disease, acute limb ischemia, or aortic dissection. Common vascular surgeries include, but are not limited to, open abdominal aortic aneurysm repair, endovascular aneurysm repair (EVAR), carotid endarterectomy, carotid stenting, vein stripping, sclerotherapy and foam sclerotherapy, endo-venous laser treatment, radiofrequency vein ablation, ambulatory phlebectomy, angioplasty with/out stenting, bypass surgery endarterectomy atherectomy, balloon embolectomy, thrombectomy, bypass surgery, open repair, thoracic endovascular aneurysm repair (TEVAR). A surgeon can apply one or more composite prosthetic patches with covalently bound particles to the surgical site at the time of surgery, prior to surgery or following surgery, to enhance the process of wound healing, or to prevent the development of vascular proliferative disorders, such as those that give rise to stenosis or restenosis.

In some embodiments composite prosthetic patches with covalently bound particles for controlled drug release are used to treat or prevent aneurysm, or pseudoaneurysm. For example, in some embodiments, composite prosthetic patches with covalently bound particles include one or more cytokines for treatment or prevention of an aneurysm, or a pseudo-aneurysm in a subject in need thereof. An exemplary cytokine for use in treatment or prevention of an aneurysm, or a pseudo-aneurysm is Transforming Growth Factor-beta (TGF-β). The composite prosthetic devices can be used to treat and prevent complications, diseases or disorders following vascular surgery. Exemplary surgeries and procedures that can lead to, or include the use of the composite prosthetic devices having bound thereto particles for delivery of active agents include are discussed in further detail, below.

a. Angioplasty

In some embodiments, the subject has undergone, is undergoing, or will undergo angioplasty. Angioplasty is the technique of mechanically widening narrowed or obstructed arteries, such as those obstructed as a result of atherosclerosis. Generally, angioplasty includes inserting into a subject's vasculature an empty and collapsed balloon on a guide wire, known as a balloon catheter, which is passed into the narrowed locations and then inflated to a fixed size. The balloon forces expansion of the inner white blood cell/clot plaque deposits and the surrounding muscular wall, opening up the blood vessel for improved flow, and the balloon is then deflated and withdrawn. A stent may or may not be inserted at the time of ballooning to ensure the vessel remains open. Angioplasty includes peripheral angioplasty (i.e., blood vessels outside the coronary arteries, such as in the abdomen, or legs), coronary angioplasty, renal artery angioplasty, carotid angioplasty, and cerebral arteries angioplasty.

In some embodiments, the subject has undergone, is undergoing, or will undergo percutaneous transluminal coronary angioplasty (PTCA). The use of PTCA has greatly reduced the number of fatalities in patients who suffer myocardial infarction (Fischman, et al., *N Engl J Med.,* 331:496-501 (1994); Elezi, et al., *Circulation* 98:1875-1880 (1998); Bennett and O'Sullivan, *Pharmacol Ther.,* 91:149-166 (2001)). During PTCA, the artery walls are expanded by several times their original diameter in an attempt to increase lumen diameter and improve flow. Unfortunately, this technique is plagued by a high incidence of vessel re-narrowing or restenosis, occurring in 30-40% of patients within 6 months of the procedure (Anderson et al., *J Interv. Cardiol.,* 6:187-202 (1993); Fischman et al., *N Engl J Med,* 331:496-501 (1994); Elezi et al., *Circulation* 98:1875-1880 (1998); Bennett and O'Sullivan, *Pharmacol Ther,* 91:149-166 (2001); Heckenkamp et al., *J Cardiovasc. Surg.* (Torino), 43:349-357 (2002)).

Prevention of restenosis after successful PTCA remains one of the most challenging tasks in the treatment of obstructive coronary artery disease. Attempts to ameliorate this proliferative response involve the use coronary stents, which have significantly improved both short term and long term outcome following interventional coronary revascularization procedures. Despite a reduction in restenosis rate with stent deployment, restenosis still occurs in 15-30% of patients within 6 months (Fischman et al., *N Engl J Med,* 331:496-501 (1994); Elezi et al., *Circulation,* 98:1875-1880 (1998)). This incidence of in-stent restenosis is expected to increase as coronary stenting is becoming more frequent and is used in less ideal lesions. Composite prosthetic patches with covalently bound particles for controlled drug release can be used to treat or prevent restenosis, abdominal adhesions and scarring following angioplasty.

iv. Transplant Arteriopathy

In some embodiments, the subject has undergone, is undergoing, or will undergo a transplant. Chronic transplant arteriopathy (CTA) is a major cause of late allograft loss after heart or kidney transplantation (Taylor, et al., *J. Heart Lung Transplant.,* 24:945-955 (2005), Burke, et al., *Transplantation,* 60:1413-1417 (1995); Cornell and Colvin, *Curr. Opin. Nephrol Hypertens.,* 14:229-234 (2005)). Therefore, in some embodiments, the composite devices are used to reduce, inhibit, or prevent transplant arteriopathy in a transplant recipient.

v. Pseudoaneurysm

In some embodiments, the subject has developed, or is at risk of developing an aneurysm or pseudoaneursym. Pseudoaneurysm formation after patch angioplasty is not a rare complication.

The traditional risk factors for aneurysm formation are hypertension, artery atherosclerosis, smoking, diabetic mellitus, etc.

The transforming growth factor-β (TGF-β) pathway plays an important role in the aneurysm formation. As described in the examples, composite prosthetic devices having bound nanoparticles eluting TGF-β1 can stimulate smad2 and TAK1 phosphorylation both in vitro and in vivo. Accordingly, in some embodiments, composite prosthetic devices having bound nanoparticles are used to prevent or decrease formation of aneurysm, and/or pseudoaneurysm, for example, resulting from patch angioplasty.

vi. Neointimal Hyperplasia

Neointimal hyperplasia is the proliferation and migration of vascular smooth muscle cells primarily in the tunica intima, resulting in the thickening of arterial walls and decreased arterial lumen space. Neointimal thickening after mechanical injury predominantly consists of a fibroproliferative reaction initially involving proliferating smooth muscle cells and later dominated by accumulation of extracellular matrix. Neointimal hyperplasia is the major cause of stenosis or restenosis after percutaneous coronary interventions such as stenting or angioplasty. The term neointima is used because the cells in the hyperplastic regions of the vascular wall have histological characteristics of both intima and normal artery cells. In some embodiments, composite prosthetic devices having particles bound thereto for drug delivery are used in a method of treating spontaneous venous neointimal hyperplasia in a subject. Intimal hyperplasia is a physiological healing response to injury of the endothelia of blood vessels. Injury to the endothelial layer triggers a series of acute and chronic inflammatory responses that trigger the aggregation of platelets, the deposition of fibrin and attracts leukocytes to the area (Murakami, et al., *Am J Physiol.,* 272:L197-L202 (1997); Cotran, et al., *J Am Soc Nephrol.,* 1:225-235 (1990)). Thus, regenerative processes that give rise to neovessel formation and intimal hyperplasia appear to be immune-mediated phenomena, similar to the proposed role for monocytes-macrophages in other human vascular biological processes, such as vein graft adaptation (Ratliff and Myles, *Arch. Pathol. Lab. Med.* 113:772-776 (1989); Motwani and Topol, *Circulation* 97:916-931 (1998)).

Methods of using composite prosthetic patches with covalently bound particles for controlled drug release for preventing intimal and neointimal hyperplasia in both biological and synthetic vascular conduits are provided. The methods can reduce or prevent stenosis and improve vascular function. The compositions can be used to treat neointimal hyperplasia associated with patch angioplasty or venoplasty when the one or more active agents is a therapeutic agent for neointimal hyperplasia.

a. Stenosis

Intimal hyperplasia can lead to thickening of the tunica intima of a blood vessel, leading to a complication of stenosis of the blood vessel. Activation of inflammatory and pro-coagulant mechanisms is thought to contribute significantly to the initiation and development of stenosis. Over a period of time ranging from a few weeks to months, smooth muscle cells from the medial region of an injured blood vessel relocate to the intimal region. These cells proliferate and deposit extracellular matrix to form a neo-intima at the site of the injury in a process analogous to scar formation (Fingerle, et al., *Proc Natl Acad Sci.,* 86:8412 (1989); Clowes, et al., *Circ. Res.,* 56:139-145 (1985)). Thus, a robust healing response leads to an internal thickening of the vessel wall (intimal hyperplasia) and eventually reduces the vessel lumen, causing stenosis. The formation of intimal hyperplasia can be accelerated by the presence of foreign material such as prosthesis within the vessel, and can result from endovascular intervention including angioplasty, bypass, and transplantation arteriopathy, etc. (Glagov, *Circulation,* 89:2888-2891 (1994)).

Therefore, methods of using composite prosthetic patches with covalently bound particles for controlled drug release to prevent intimal hyperplasia and stenosis are provided.

b. Restenosis

Methods to prevent or reduce restenosis of the coronary vasculature or the peripheral circulatory system are provided. Restenosis of blood vessels is typically due to intimal hyperplasia. A surgical device, such as a stent, may be inserted to open the stenosed vessel, however this is also problematic because the stent itself can stimulate further intimal hyperplasia. In addition, hyperplastic intimal tissue can grow through the interstices of a bare stent and re-stenose the vessel. Whilst covered stents may prevent this from happening, intimal hyperplasia can still occur at the ends of the stent where there is most irritation of the vessel wall. Patients with in-stent restenosis are at risk of serious complications, as stenosis from intimal hyperplasia is often difficult to treat. Unlike soft atheromatous plaques, these stenoses are firm and require prolonged high inflation pressures to dilate with a balloon. The stenoses often recur and repeated dilatation of the vessel leads to repeated intimal injury and perpetuates the intimal healing response.

Accordingly, the composite prosthetic patches with covalently bound particles for controlled drug release can be administered to a subject to reduce or inhibit smooth muscle cell proliferation, migration, and a combination thereof in an amount effective to reduce or inhibit neointima formation and thereby treat or prevent restenosis and other vascular proliferation disorders in the subject. In some embodiments, the patency of biological or synthetic vessels and devices can be increased using a composite prosthetic patches with covalently bound particles for controlled drug release. Therefore, methods for administering composite prosthetic patches with covalently bound particles for controlled drug release to the subject prior to, during or after injury or surgery to the cardiovascular system are provided.

vii. Inflammation

Inflammatory response is triggered when tissues are exposed to a variety of insults. This response consists of a cascade of events that includes release of various chemical mediators and recruitment of circulating blood cells (platelets and leukocytes) to the site of injury and their subsequent activation. The inflammatory response attempts to contain the damaging effects of the insult, leading to recovery from its injurious effects.

The compositions can be used to mitigate various inflammation responses associated with patch surgeries.

viii. Atherosclerosis

Atherosclerosis involves multiple processes, including inflammation, vascular proliferation and matrix alteration (reviewed in Dzau, et al., *Nat Med.*, 8(11) (2002)). In atherosclerosis, VSMC give rise to inflammation, the retention of lipoproteins from the blood, as well as the development of a fibrous deposit that constitute a plaque Inflammation has been shown to mediate all stages of atherosclerosis: in the development of an atheroma plaque, VSMCs produce pro-inflammatory mediators such as monocyte chemo-attractant proteins, and synthesize matrix molecules that give rise to the retention of lipoproteins from the blood; and following the development of a plaque, local inflammatory milieu can induce collagenase expression and inhibit expression of proteolytic inhibitors, rendering the fibrous cap weak and susceptible to rupture. Therefore, in some embodiments, composite prosthetic patches with covalently bound particles for controlled drug release are used to treat, reduce, inhibit, or prevent vascular proliferation disorders in a subject.

2. Congenital Diaphragmatic Hernia

Congenital diaphragmatic hernia (CDH) is characterized by a variable degree of pulmonary hypoplasia associated with a decrease in cross-sectional area of the pulmonary vasculature and alterations of the surfactant system. There are three basic types of congenital diaphragmatic hernia: the posterolateral Bochdalek hernia (occurring at approximately 6 weeks' gestation), the anterior Morgagni hernia, and the hiatus hernia. CDH is estimated to occur with an incidence of 1 in 3600 live births, with the majority presenting in infancy. Infants with congenital diaphragmatic hernias most commonly present with respiratory distress and cyanosis in the first minutes or hours of life, although a later presentation is possible. The respiratory distress can be severe and may be associated with circulatory insufficiency, requiring aggressive resuscitative measures. The incidence of re-herniation following CDH repair ranges from 7% to 46% depending on the closure modality.

The compositions can be used to alleviate various CDH when prosthetic patches are applied in treating CDH with one or more active agents.

3. Orthopedic Defect

Defects in soft orthopedic tissues (i.e., cartilage) and hard orthopedic tissues (i.e., bones). Cartilage defects lead to osteoarthritis, when the smooth, gliding surface on the end of the bone loses its cushioning, deformity develops, and bone rubs on bone. Damage may occur as the result of a sudden injury or wear and tear over time. Bone defects often result from tumor resection, congenital malformation, trauma, fractures, surgery, or periodontitis in dentistry.

The compositions can be used to treat various orthopedic defect when the prosthetic patch is used to stimulate the regeneration of bones or soft tissues with one or more active agents.

4. Fascial Defect

A defect in the connective tissue fibers, primarily collagen, that forms beneath the skin to attach, stabilize, enclose, and separate muscles and other internal organs.

The compositions can be used to treat various fascial defects when the prosthetic patch is used to cover fascial defects with one or more active agents.

C. Combination Therapies

Composite prosthetic devices for drug delivery can be used in combination with one or more additional therapeutic agents. The term "combination" or "combined" is used to refer to either concomitant, simultaneous, or sequential administration of two or more agents. Therefore, the combinations can be administered either concomitantly, separately but simultaneously, or sequentially (e.g., one of the compounds or agents is given first followed by the second). The additional therapeutic agents can be administered locally or systemically to the subject, or coated or incorporated onto, or into a device or graft.

In some embodiments, the additional therapeutic agents are other anti-neointima agents, chemotherapeutic agents, antibodies, antibiotics, antivirals, steroidal and non-steroidal anti-inflammatories, conventional immunotherapeutic agents, immunosuppressants, cytokines, chemokines and/or growth factors. For example, in some embodiments, methods of using composite prosthetic devices for delivery of one or more active agents include delivery of one or more other agents via a distinct route, for example, via enteral or parenteral delivery at the same or different time as delivery of the same or different active agent via the composite prosthetic device.

Exemplary additional therapeutic agents include, but are not limited to, Paclitaxel, Taxotere, other taxoid compounds, other anti-proliferative agents such as methotrexate, anthracyclines such as doxorubicin, immunosuppressive agents such as Everolimus and Serolimus, and other rapamycin and rapamycin derivatives.

In some embodiments, one or more additional therapeutic agents include other anti-proliferatives or anti-migrations agents designed for treating or preventing neointima formation or restenosis.

D. Dosages and Effective Amounts

In some embodiments, the composite prosthetic devices with covalently bound particles for controlled drug release are implanted within, or otherwise applied to a subject to deliver one or more active agents in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiological effect. The precise dosage will vary according to a variety of factors such as subject-dependent variables (e.g., age, immune system health, etc.), the disease or disorder, and the treatment being effected.

For all of the described active agents, the ordinary skilled worker, considering the therapeutic context, age, and general health of the recipient, will be able to ascertain appropriate dosage levels for treatment of various conditions in various patients. The selected dosage depends upon the desired therapeutic effect, on the route of administration, and on the duration of the treatment desired. Generally dosage levels of between 0.001 and 100 mg/kg of body weight daily are administered to mammals, most preferably, humans. Generally, for drugs loaded into particles bound to the composite prosthetic devices, dosages will depend upon the efficacy of release of the active agent, as well as the time course over which the total amount of the active agent is to be released. In some embodiments, the dosage of active agent that is effective will be equivalent to that typically administered when given by intravenous injection or infusion. Preferably, the compositions are formulated to achieve a serum level of between about 1 nM and about 1000 µM at the site where treatment is desired.

In some embodiments, the active agents are effective to prevent the normal biological activities of immune cells, such as macrophages, platelets and NK cells. For example, one or more active agent can be in an amount effective to reduce or prevent the migratory or chemotactic activity of macrophages.

In one embodiment the one or more active agents are present in the composite devices in an amount effective to prevent or reduce neointima formation in a subject. In a preferred embodiment the amount of one or more active agents is not released in an amount effective to be toxic to the subject, or to prevent one or more desirable biological processes in the subject. For example, the active agent preferably does not prevent wound healing or the formation of neotissue in a subject compared to an untreated control. In some embodiments, the amount of one or more active agents is effective to prevent or reduce formation of an aneurysm or pseudoaneurysm in a subject.

In preferred embodiments, the active agents delivered by composite prosthetic devices result in local concentrations that are twice, 10 times, 100 times, 500 times, 1000 times or more than 1000 times greater than that achieved by systemic administration of the same compound. In preferred embodiments the locally administered active agents' inhibitors are steadily released at the site of delivery at a constant rate over a period of time. Preferably, the steady release maintains a desired concentration of the active agents at the site of delivery.

In some embodiments, the composite prosthetic devices having bound particles for drug delivery administer active agents during a period before, during, or after onset of disease symptoms, or any combination of periods before, during or after onset of one or more disease symptoms. For example, the devices can deliver to the subject one or more doses of an active agent every 1, 2, 3, 4, 5, 6 7, 14, 21, 28, 35, or 48 days prior to onset of disease symptoms; the devices can deliver to the subject one or more doses of an active agent every 1, 2, 3, 4, 5, 6, 7, 14, 21, 28, 35, or 48 days after the onset of disease symptoms. In some embodiments, the devices deliver to the subject multiple doses of a therapeutic agent before an improvement in disease condition is evident. For example, in some embodiments, the subject receives 1, 2, 3, 4, 5, 6 7, 14, 21, 28, 35, or 48, doses over a period of 1, 2, 3, 4, 5, 6 7, 14, 21, 28, 35, or 48 days or weeks before an improvement in the disease or condition is evident.

The timing of commencement of the release of the active agent from the composite prosthetic devices should be configured as determined by the needs of the subject, and can vary from at the time of surgery or injury, to one or more days, weeks or months after surgery or injury. Therefore, methods for using the composite prosthetic devices for delayed release of one or more active agents are provided. In some embodiments, composite prosthetic devices are configured to discontinue release of active agents once vascular neo-tissue growth has occurred.

In some embodiments composite prosthetic devices are configured to deliver a single dose of one or more active agents to a subject as one or more bolus doses to raise the blood concentration of the one or more inhibitors to a desired level. In certain embodiments, the placement of the composite prosthetic device can be varied depending upon the desired effect and the target organ or tissue to be treated. In a particular embodiment, the device is configured to release one or more different dosages of the same or different active agents consecutively or simultaneously. For example, in a particular embodiments, the device delivers a bolus dose, prior to the constant administration of the same or a different active agent.

Thus, the desired blood concentration of one or more active agents can be maintained for a desired period of time using a single device having bound thereto a combination of different nanoparticles, loaded with the same or different agents, formulated for immediate, delayed or continuous release.

1. Controls

The effect of an active agent can be compared to a control. Suitable controls are known in the art and include, for example, untreated cells or an untreated subject. In some embodiments, the control is untreated tissue from the subject that is treated, or from an untreated subject. Preferably the cells or tissue of the control are derived from the same tissue as the treated cells or tissue. In some embodiments, an untreated control subject suffers from the same disease or condition as the treated subject. For example, in some embodiments, one or more of the pharmacological or physiological markers or pathways affected by treatment with an active agent is compared to the same pharmacological or physiological marker or pathway in untreated control cells or untreated control subjects. For example, treated subjects can be compared to subjects treated with other inhibitors of neointima formation. The subjects treated with other inhibitors of neointima formation can have a greater incidence of in postoperative stenosis, or a reduced formation of neo-vascular tissue than do subjects treated with the composite prosthetic devices bound to particles for drug delivery.

The devices with covalently bound particles loaded with one or more active agent(s) are more effective at treating, preventing or diagnosing complications, than are the patches alone or patches with control (i.e., un-loaded) particles, and do not induce inflammation. The examples demonstrate that pericardial patches with covalently bound PLGA nanoparticles containing rapamycin inhibit the proliferation of smooth muscle cells in vitro and in vivo, and reduce at least two-thirds of neointimal thickness several days post operation and at least one third of neointimal thickness 30 days post operation, as compared with control (i.e., unmodified) patches or patches with covalently bound un-loaded nanoparticles. The modified patches at pericardium have some shedding of particles into liver, kidney and spleen after 24 hours compared with a negative control, but almost none in the lung, heart, skeletal muscle, brain and aorta.

The present invention will be further understood by reference to the following non-limiting examples.

EXAMPLES

Example 1. Preparation and Characterization of Nanoparticle-Patch Composites

Materials and Methods
Synthesis of Nanoparticles (NPs)

NPs were prepared using an emulsion method. Carboxylated PLGA (inherent viscosity 0.55-0.75 dL/g) (100 mg)

and rapamycin (5 mg) were dissolved in chloroform, and then added drop-wise to 5% polyvinyl alcohol (PVA). The mixture was sonicated three times and then added to 0.2% PVA solution. The solvent was evaporated for 2 hours while stirring and the PLGA particles were centrifuged before lyophilization (Bal, et al., Sci Rep.; 7: 40142 (2017)).

The size and polydispersity Index (PDI) of the nanoparticles were measured using a Zetasizer (Malvern, Westborough, Mass.). Light scattering was measured by back-scattering at a detection angle of 173 and a wavelength of 532 nm; the hydrodynamic radius ($R_H$) was calculated using the Stokes-Einstein equation:

$$R_H = \frac{k_B T}{6\pi \eta D_0}$$

where $k_B$=Boltzmann constant, T=absolute temperature, $\eta$=solvent viscosity, $D_0$=diffusion coefficient at infinite dilution.

Covalent Modification of Patches with Nanoparticles

Bovine collagen pericardial patches were trimmed to 7 mm×5 mm pieces and ethyl(dimethylaminopropyl) carbodiimide IN-hydroxysuccinimide (EDC/NHS) chemistry was then used to conjugate the NP to the patch. EDC (20 μmol/mL) and NHS (10 μmol/mL) were dissolved in 2-(N-morpholino)ethanesulfonic acid (MES) (0.1M; pH 5) for the conjugation. Carboxyl groups on the NP were activated using EDC (1 mL) for 30 min and substituted with NHS by adding NHS (1 mL) for 30 min. The solution pH was raised from 5 to 8 using NaOH (1M; 200 μL). Patches were then placed into solution and incubated at 37° C. overnight.

Assessment of Patch-NP Topology Using Scanning Electron Microscopy (SEM)

Scanning electron microscopy (SEM) was performed using a Hitachi S-4800 High Resolution SEM (Hitachi High Technologies Inc., Tokyo, Japan). Collagen patches before and after conjugation of NPs were lyophilized and mounted on the aluminum sample holder to be sputter-coated with chromium. The patches were observed with an accelerating voltage of 15 kV at a working distance of 4 mm.

Results

Scanning electron microscopy confirmed the presence of NP-rapamycin on the surface as well as inside of the patches, within the interstices of the collagen fibers. FIG. 1A schematically shows rapamycin encapsulated within nanoparticles (NP-rapamycin; 30 ng rapamycin/μg nanoparticle; mean NP diameter 369.9 nm; mean zeta-potential −37.8±2.9 mV; rapamycin encapsulation efficiency 85.7%) and conjugation of the nanoparticles to pericardial patches.

Nanoparticles are conjugated to patches at a density of approximately 2.67 μg/mm², and the implanted patch is approximately 3×1.5×0.6 mm (length×width×height). There are at least approximately 360 ng of rapamycin in 12 μg of nanoparticles.

Example 2. Nanoparticle-Mediated Release of Active Agents from Pericardial Patches is Sustained for 15 Days and Inhibits the Proliferation of Smooth Muscle Cells In Vitro Materials and Methods Assessment of Active Agent Release from Patches Patches conjugated with NP containing rapamycin (NP-rapamycin) were incubated in phosphate buffered saline (PBS) at 37° C. The supernatant of each sample was collected and analyzed for absorption at 400 nm at each time point using a SpectraMax plate reader (Molecular Devices, Sunnyvale, Calif.). Patches conjugated with NP containing rhodamine (NP-rhodamine) were incubated in PBS at 37° C.; control patches were incubated in PBS containing free rhodamine. At various time points patches were washed in PBS and their fluorescence intensity was measured.

Culture of Human Smooth Muscle Cells

Human smooth muscle cells (SMCs), passages 6-8, were cultured in endothelial basal medium 2, supplemented with endothelial cell growth media-2 MV SingleQuot Kit Supplement & Growth Factors (Lonza), 20% fetal bovine serum, penicillin/streptomycin, and L-glutamine (Corning Life Sciences). At approximately 60% confluence, NP and NP-rapamycin were added to the cells. Cells were generously provided by Dr. Mingzhu Yin, Pathology Department, Yale School of Medicine, New Haven, Conn.

Western Blotting and Analysis

Pericardial patches were carefully harvested and removed from surrounding tissue and the neointima was carefully dissected free from the patch and snap frozen in liquid nitrogen. Samples were crushed and mixed with buffer including protease inhibitors (Roche, Complete Mini 12108700) prior to sonication (5 sec) and centrifugation (135,000 rpm, 15 min). Equal amounts of protein from each experimental group were loaded for SDS-PAGE, followed by Western blot analysis with signals detected using the ECL detection reagent. Patches were analyzed individually, without combination of samples.

Results

Figure 1D:
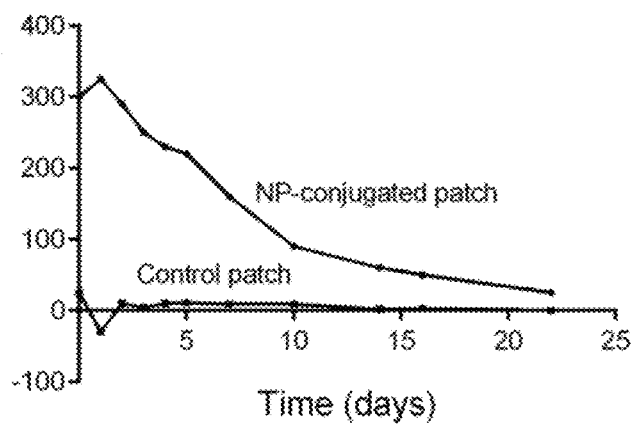
FIG. 1D is a line graph showing the fluorescence intensity versus time (days) for each of the NP-conjugated patch and the Control patch, respectively.

The cumulative release of rapamycin from the NP-rapamycin-conjugated patches plateaued by day 15 in vitro (FIG. 1B), suggesting the ability to deliver the drug for at least 2 weeks. Since these patches are primarily collagen fibers, the NP are conjugated throughout the patch in addition to the patch surface, facilitating a localized and increased concentration profile of the released drug. The density of nanoparticles conjugated to the patch was linear at low numbers but was saturated at higher numbers of nanoparticles (FIG. 1C). NP were released from patches over approximately 3 weeks in vitro (FIG. 1D).

Figure 2A:
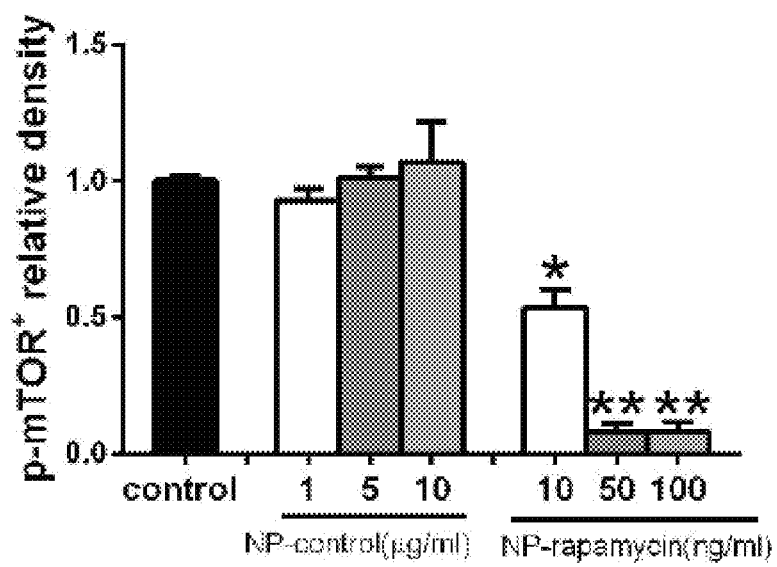
FIG. 2A is a bar graph showing the normalized phosphorylation of mTOR expression of smooth muscle cells (SMCs) in vitro as relative intensity (non-treated SMC as 1) versus concentrations of control nanoparticles, NP-control, (µg of particles/ml) or rapamycin loaded nanoparticles, NP-rapamycin, (ng of rapamycin/ml). Treatment time is between one and four hours, typically two hours. The unit of NP-rapamycin versus control is (µg particles/ml/per patch). Particles are loaded with a range of between one and ten µg of rapamycin that is released slowly on the patch. As a result, the unit is ng of rapamycin. *, p=0.0004, 10 ng/ml vs. control; **, p<0.0004, 50 ng/ml, 100 ng/ml vs. 10 ng/ml; n=3.
Figure 2B:
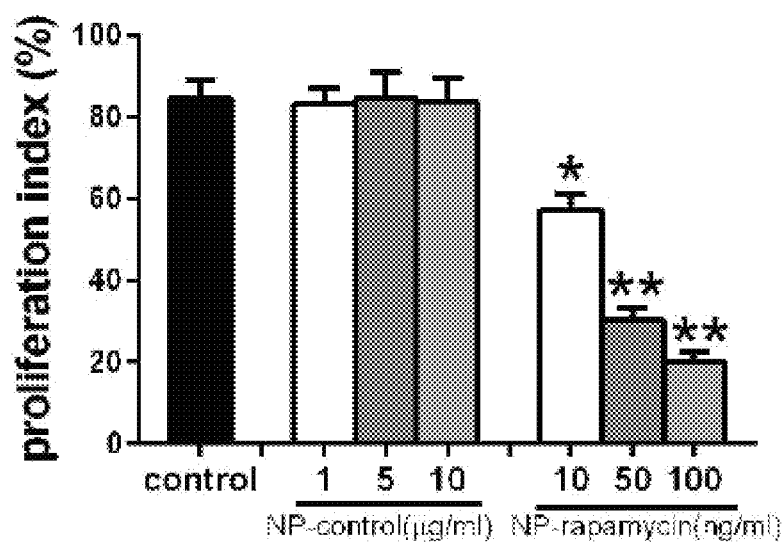
FIG. 2B is a bar graph showing the percent of proliferation in human aorta SMC in vitro after 24 hours of incubation with NP-control (µg of particles/ml) or NP-rapamycin (ng of rapamycin/ml), with SMC at 0 hour being 100%. *, p<0.0001; **, p<0.0001, n=3. Particles containing RAPA are attached to the patches. The patches are cultured with cells. The cells are NOT cultured in patches.

FIG. 2A-2B demonstrate that the SMCs treated with control NP show no change in Ki67 expression or phosphorylation of mTOR, whereas SMCs treated with NP-rapamycin show diminished Ki67 expression and phosphorylation of mTOR. These results show that the rapamycin delivered from NP-conjugated patches remain biologically active over a period of at least two weeks.

Example 3. Nanoparticle-Patch Composite Delivery System does not Introduce Toxicity to Lungs In Vivo Materials and Methods Rats were anesthetized with isoflurane inhalation, and tissues were fixed by transcardial perfusion of phosphate buffered saline (PBS) followed by 10% formalin. Tissue was removed and fixed overnight in 10% formalin followed by a 24-hour immersion in 70 percent alcohol. Tissue was then embedded in paraffin and sectioned (5 μm thickness). Tissue sections were de-paraffinized and stained with hematoxylin and eosin.

Results

Figure 3A:
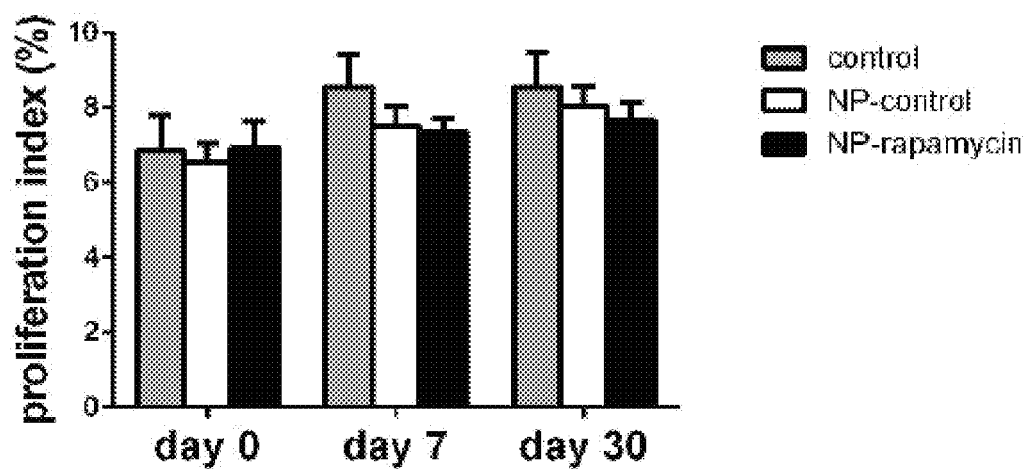
FIG. 3A is a bar graph showing the percent of proliferating (Ki67+) cells in the lung in rats after day 0, 7 and 30 of receiving control (plain patch), NP-control patch, or NP-rapamycin patch. n=3; group, p=0.0742; time, p=0.4306.
Figure 3B:
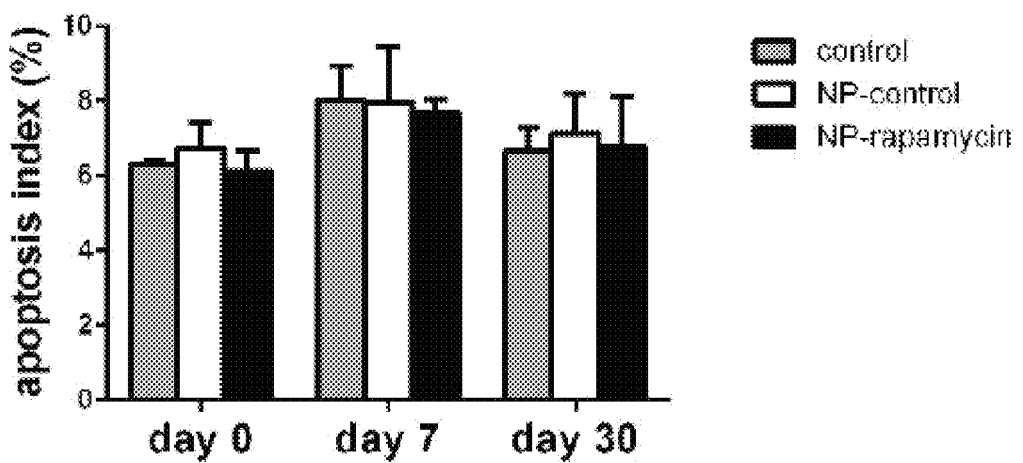
FIG. 3B is a bar graph showing the percent of apoptosis (cleaved caspase-3+) cells in the lung in rats after day 0, 7 and 30 of receiving control (plain patch), NP-control patch, or NP-rapamycin patch; n=3; group, p=0.1433; time, p=0.8415.

FIG. 3A demonstrates that there is no decrease in proliferation in the lungs of rats that had NP-rapamycin patches implanted compared to control or NP-control patches. FIG. 3B demonstrates that there is also no increase in apoptosis in the lungs of rats that had NP-rapamycin patches compared to control or NP-control patches. Further, rapamycin was not present in detectable quantities in serum on days 1, 3 and 7 after implantation of NP-rapamycin patches, as determined by ELISA with detection threshold 5 ng/ml.

Example 4. Minimal Shedding of Nanoparticles from the Nanoparticle-Patch Composites after Implantation are Tested In Vivo Materials and Methods To determine the distribution of nanoparticles after implantation, patches were conjugated with nanoparticles containing rhodamine and then implanted into the infrarenal vena cava (IVC) of rats.

Synthesis of Nanoparticles Encapsulating Rhodamine

NPs were prepared using an emulsion method. Carboxylated PLGA (100 mg) and rhodamine (1 or 10 mg) were dissolved in chloroform, and then added drop-wise to 5% polyvinyl alcohol (PVA). The mixture was sonicated three times and then added to 0.2% PVA solution. The solvent was evaporated for 2 h while stirring and the PLGA particles were centrifuged before lyophilization as previously described. To measure the loading of rhodamine, nanoparticles were dissolved in DMSO and analyzed in a plate reader ($\lambda$ex 575 nm; $\lambda$em 605 nm). For rapamycin, NaOH (1 M) was added in DMSO samples and absorption at 400 nm was measured.

IVC Model

Male Wistar rats (6-8 week old) were used for patch implantation (n=111). Microsurgical procedures were performed aseptically in a dedicated facility using a dissecting microscope (Leica MZ 95, Germany). Anesthesia was given via isoflurane inhalation. A midline incision was made in the abdomen, and the infrarenal vena cava (IVC) was exposed. The site of patch implantation was approximately 2 mm below the level of the origin of the renal veins; the IVC was dissected free at this site, and all lumbar veins at this level were ligated and divided using 6-0 nylon sutures. The infrarenal IVC was clamped and a longitudinal 3 mm venotomy was made on the anterior wall of the IVC. The venotomy was closed with a pericardial patch (3 mm×1.5 mm×0.6 mm; Xenosure; LeMaitre Vascular, Burlington, Mass.) using interrupted 10-0 nylon sutures. After completion of the venoplasty closure, the clamps were removed to vent the patch and then restore blood flow in the IVC. The abdomen was closed using 5-0 Dacron sutures.

Detection Method

Rats were sacrificed on postoperative days 1, 3, 7, or 30 and the patches and organs were analyzed by fluorescence microscope.

Results

Figure 4A:
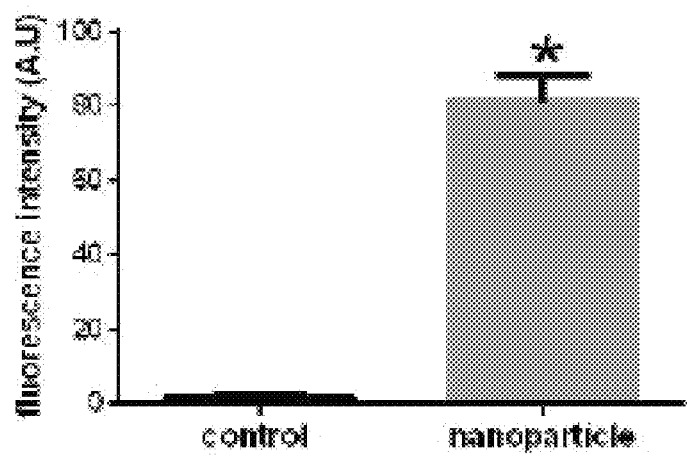
FIG. 4A is a bar graph showing the immunofluorescence intensity (A.U.) of rhodamine-loaded nanoparticles covalently bound to patches in comparison to plain patches after implantation in infrarenal vena cava (IVC) of rats. *, p=0.0003; n=3.
Figure 4B:
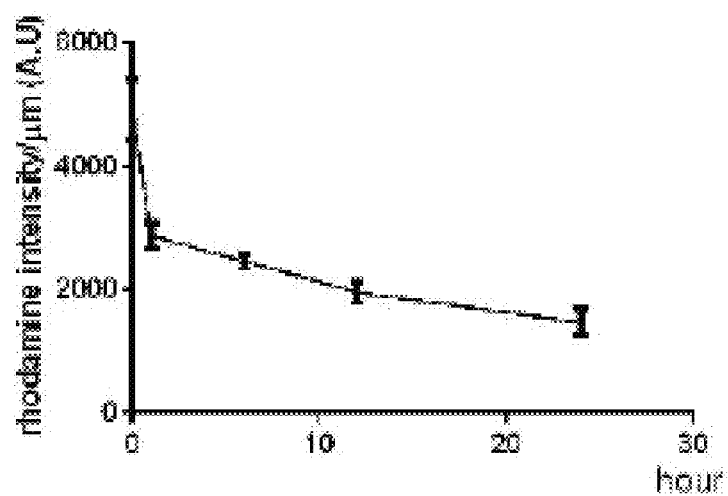
FIG. 4B is a line graph showing a change of immunofluorescence intensity (A.U.) of rhodamine-loaded nanoparticles on the patch luminal surface after implantation in rat's IVC from time 0 hour to 24 hours. n=3.
Figure 4C:
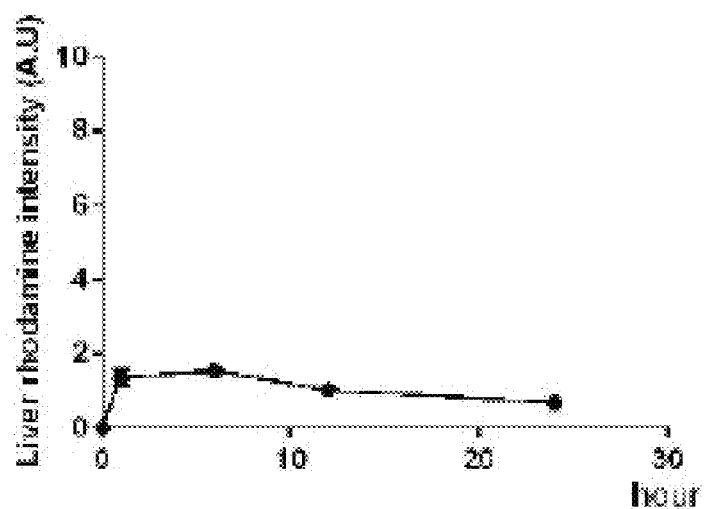
FIG. 4C is a line graph showing a change of immunofluorescence intensity (A.U.) of rhodamine-loaded nanoparticles in the liver after implantation in rat's IVC from time 0 hour to 24 hours; n=3.
Figure 4D:
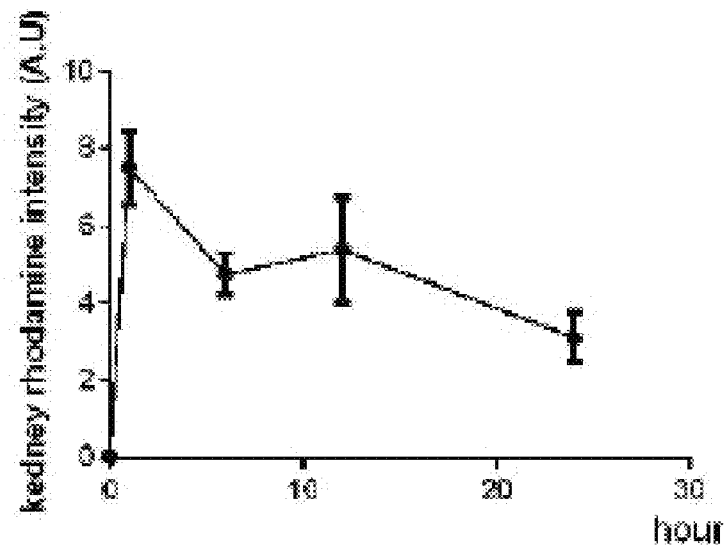
FIG. 4D is a line graph showing a change of immunofluorescence intensity (A.U.) of rhodamine-loaded nanoparticles in the kidney after implantation in rat's IVC from time 0 hour to 24 hours; n=3.

FIG. 4A demonstrates the strong immunofluorescence of patches after NP-rhodamine conjugation compared to control patches. FIG. 4B demonstrates that NP-rhodamine patches retain their immunofluorescence for at least 24 hr after implantation. FIG. 4C-4D demonstrate that NPs-rhodamine are detectable in the rat liver, kidney and spleen, with very little NP-rhodamine in the lung, heart, skeletal muscle, brain or aorta.

Example 5. Nanoparticle-Mediated Rapamycin Release from Pericardial Patches Inhibits Localized Neointimal Hyperplasia In Vivo Materials and Methods NP-rapamycin-conjugated pericardial patches were implanted in veins and the amount of neointimal hyperplasia was compared to patches without any nanoparticles (Control) as well as to patches conjugated with NPs but not containing any rapamycin (NP-control).

Animal Model

Male Wistar rats (6-8 week old) were used for patch implantation. Microsurgical procedures were performed aseptically in a dedicated facility using a dissecting microscope (Leica MZ 95, Germany). Anesthesia was given via isoflurane inhalation. A midline incision was made in the abdomen, and the infrarenal vena cava (IVC) was exposed. The site of patch implantation was approximately 2 mm below the level of the origin of the renal veins; the IVC was dissected free at this site, and all lumbar veins at this level were ligated and divided using 6-0 nylon sutures. The infrarenal IVC was clamped and a longitudinal 3 mm venotomy was made on the anterior wall of the IVC. The venotomy was closed with a pericardial patch (3 mm×1.5 mm×0.6 mm; Xenosure; LeMaitre Vascular, Burlington, Mass.) using interrupted 10-0 nylon sutures. After completion of the venoplasty closure, the clamps were removed to vent the patch and then restore blood flow in the IVC. The abdomen was closed using 5-0 Dacron sutures. Rats were sacrificed on postoperative days 1, 3, 7, or 30 and the patches and organs explanted for analysis. No immunosuppressive agents, antibiotics or heparin were given at any time.

Serum Rapamycin Assay

Following explantation of NP-rapamycin conjugated patches on days 1, 3, or 7 (n=9), whole blood was collected from the IVC (4 ml) and transferred to a BD Microtainer® MAP Microtube with K2EDTA (1.0 mg). Samples were analyzed using liquid chromatography-tandem mass spectrometry (LC-MS/MSusing methanol/water as the solvent system (Waters Acquity; Department of Laboratory Medicine, Yale-New Haven Hospital, New Haven, Conn.). Ascomycin and Cyclosporin D were used as internal standards.

Histology

Figure 5A:
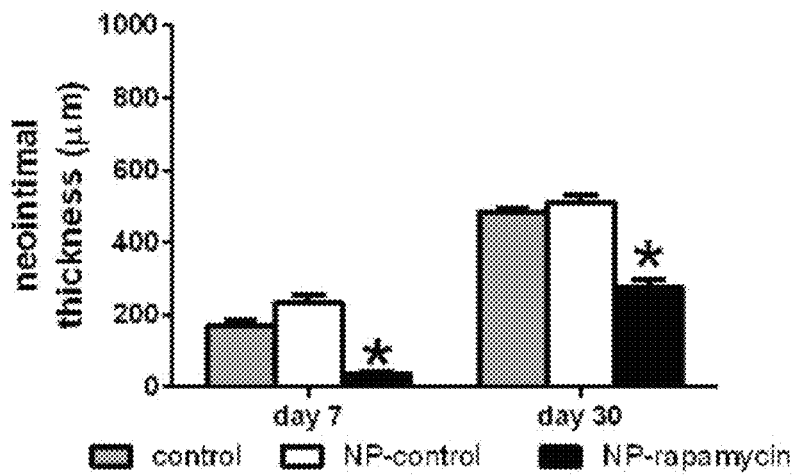
FIG. 5A is a bar graph showing the neointimal thickness at day 7 and day 30 after patch venoplasty comparing control (plain patch), NP-control patch, and NP-rapamycin patch; *, p<0.003, vs. NP-control and control, n=4-8.
Figure 5B:
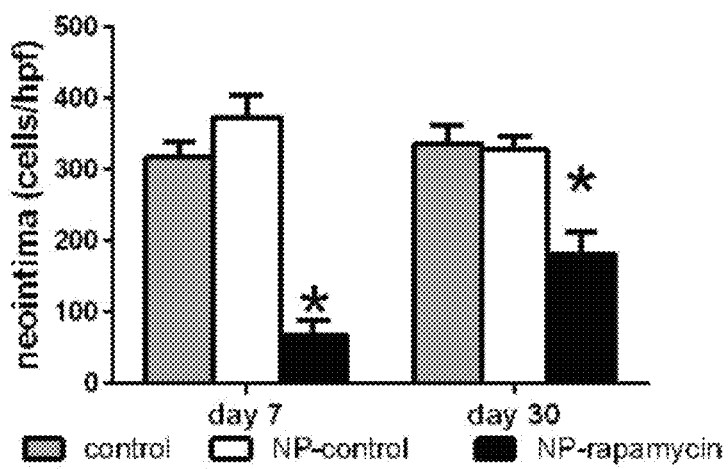
FIG. 5B is a bar graph showing neointimal cell numbers on the luminal surface of patches at day 7 and day 30 after patch venoplasty; *, P<0.0001, vs. NP-control and control; n=4-8.
Figure 5C:
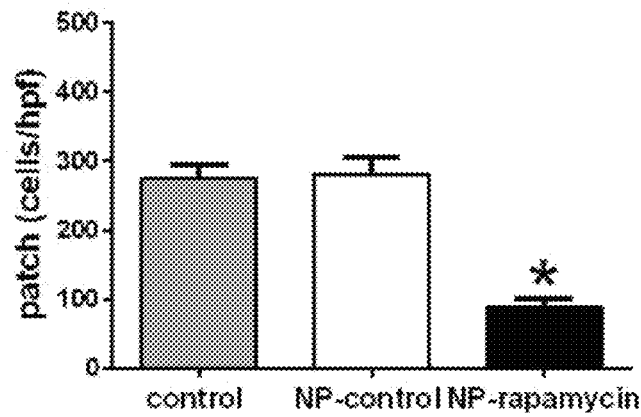
FIG. 5C is a bar graph showing cell number in the body of patches at day 7 after patch venoplasty (p=0.0004, ANOVA); *, P=0.0007, vs. NP-control (posthoc test).
Figure 5D:
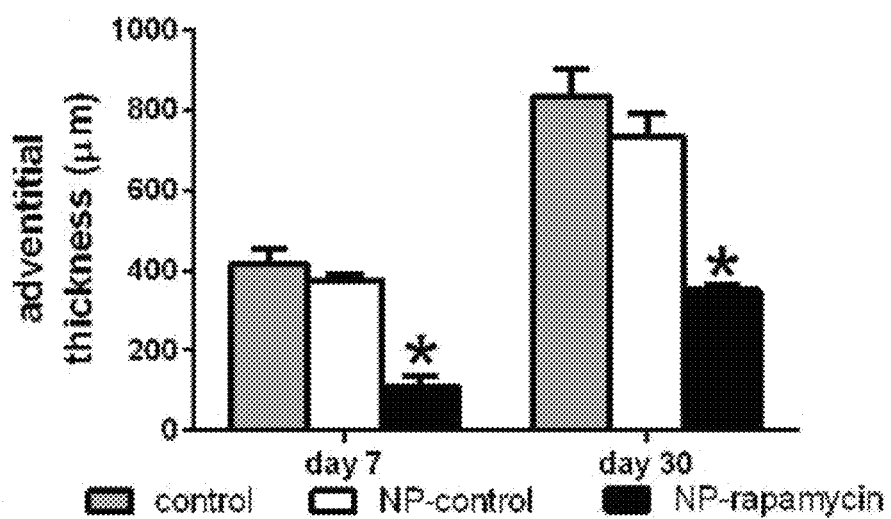
FIG. 5D is a bar graph showing the adventitia thickness at day 7 and day 30 after patch venoplasty; *, p<0.01, NP-rapamycin vs. NP-control and control.
Figure 5E:
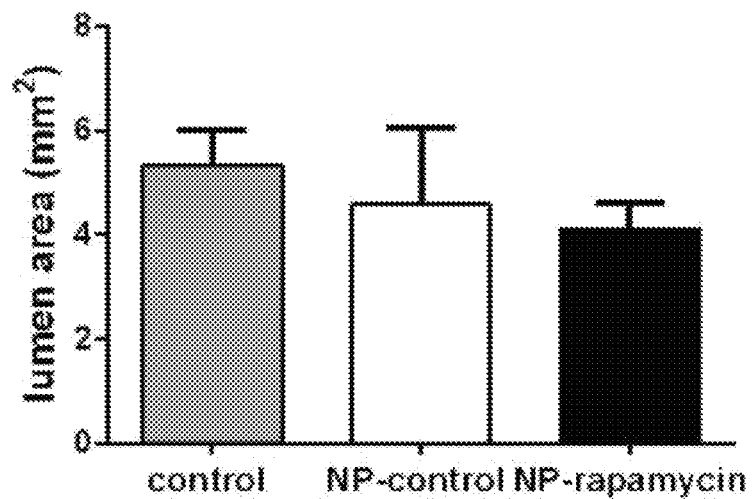
FIG. 5E is a bar graph showing vessel luminal area at day 7 after patch venoplasty (p=0.1181, ANOVA). n=3-8.
Figure 5F:
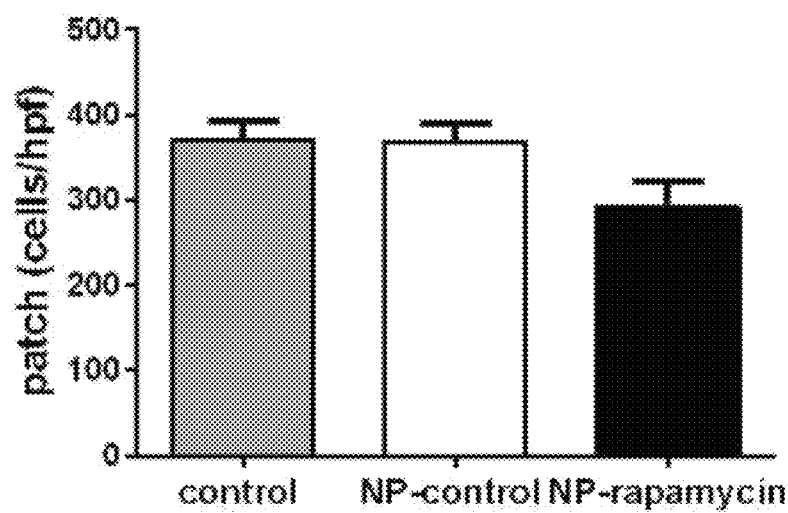
FIG. 5F is a bar graph showing cell number per high power field (number/hpf) within the body of the patches at day 30 after patch venoplasty (p=0.0948; ANOVA).
Figure 5G:
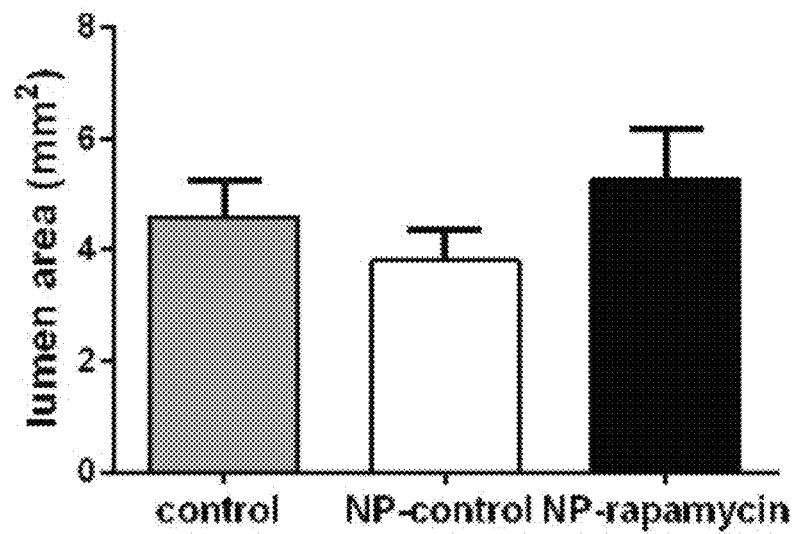
FIG. 5G is a bar graph showing vessel luminal area at day 30 after patch venoplasty (p=0.4062, ANOVA). n=4-6.

Tissue sections were de-paraffinized and then incubated using primary antibodies overnight at 4° C. After overnight incubation, the sections were incubated with EnVision reagents for CD31, CD34, VEGFR2, or Eph-B4 for 1 h at room temperature and treated with Dako Liquid DAB Substrate Chromogen System (Dako). Finally, the sections were counterstained with Dako Mayer's Hematoxylin, Results At day 7, a thick adventitia covered the patch in the control and NP-control group, whereas a very thin adventitia covered the patch in the NP-rapamycin group; the adventitia was thick in all groups by day 30. FIG. 5A demonstrates that after 7 days there is significantly less neointima formed on NP-rapamycin patches compared to both control and NP-control patches; and that after 30 days, the neointima in the NP-rapamycin patches is also thinner than the control and NP-control patches. FIGS. 5B-5C demonstrate that patches conjugated with NP-rapamycin show significantly fewer neointimal cells at both day 7 and day 30 than NP-control patches or plain patches, and that there are fewer cells in the body of the NP-rapamycin patches at day 7. FIGS. 5D-5E demonstrate that the thickness of the adventitia is reduced on the NP-rapamycin patches at both day 7 and day 30, but without any difference in vein lumen area at day 7. FIGS. 5F-5G demonstrate no significant difference in the number of cells within the body of the patches and in vein lumen area at day 30.

Figure 5H:
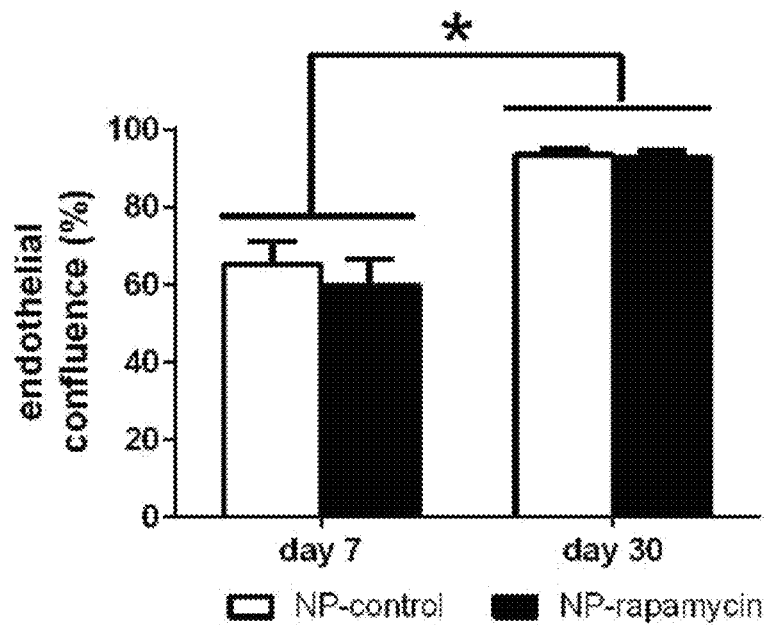
FIG. 5H is a bar graph showing neointimal endothelial confluency as a percentage of coverage at day 7 and day 30 after patch venoplasty comparing the NP-control patches with NP-rapamycin patches; *, p<0.05.
Figure 5I:
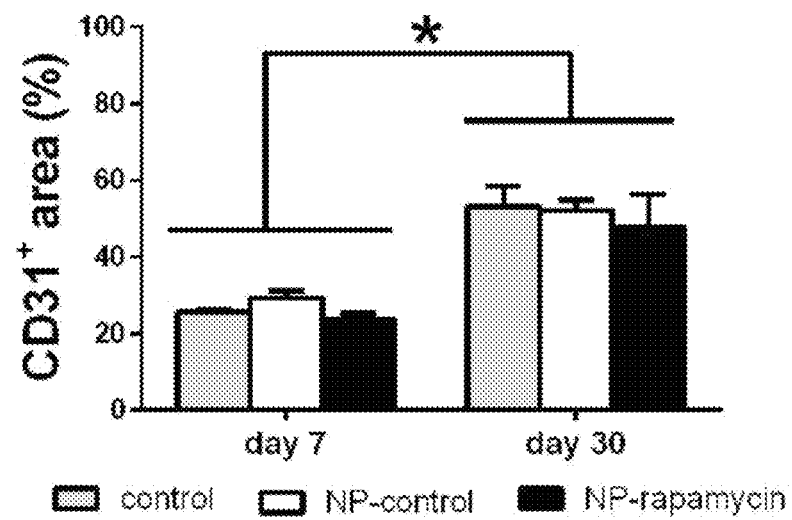
FIG. 5I is a bar graph showing the presence of CD31-positive cells on the neointimal surface at day 7 and day 30 after patch venoplasty as an area percentage; *, p<0.05; n=3.

FIG. 5H demonstrates that CD31-positive cells are present at the neointimal surface in both NP-control and NP-rapamycin patches, with increasing endothelial coverage from day 7 to day 30 in both groups. FIG. 5I demonstrates no difference in the number of CD31 positive cells on the neointimal surface of all patches from en-face staining. The numbers of cells that are positive for both CD34 and VEGFR2, both CD34 and Eph-B4, as well as CD31 and Eph-B4, are similar between NP-rapamycin and NP-control patches, which is consistent with the data that the numbers of EPC, venous EPC, as well as mature venous endothelial cells are also similar, respectively.

Figure 6A:
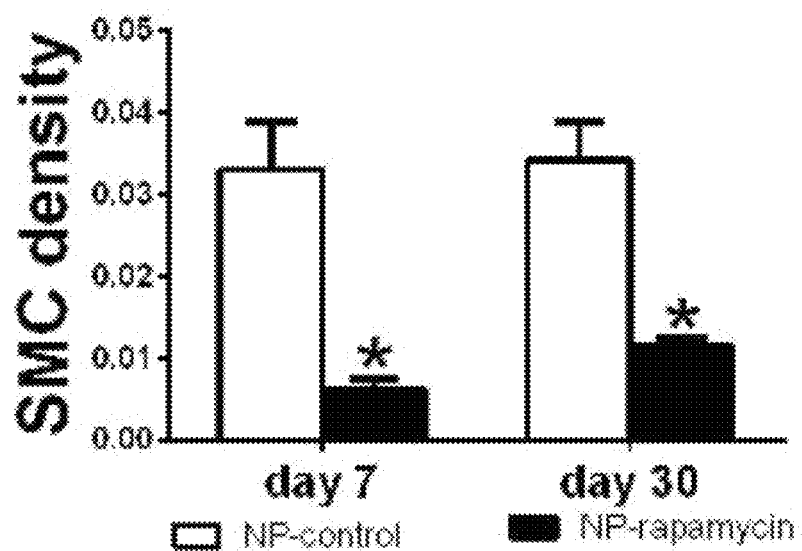
FIG. 6A is a bar graph showing SMC density at day 7 and day 30 after patch venoplasty comparing NP-control patch with NP-rapamycin patch. *, P<0.006, NP-rapamycin vs. NP-control; n=4. SMC density is SMC number fraction in the total.
Figure 6B:
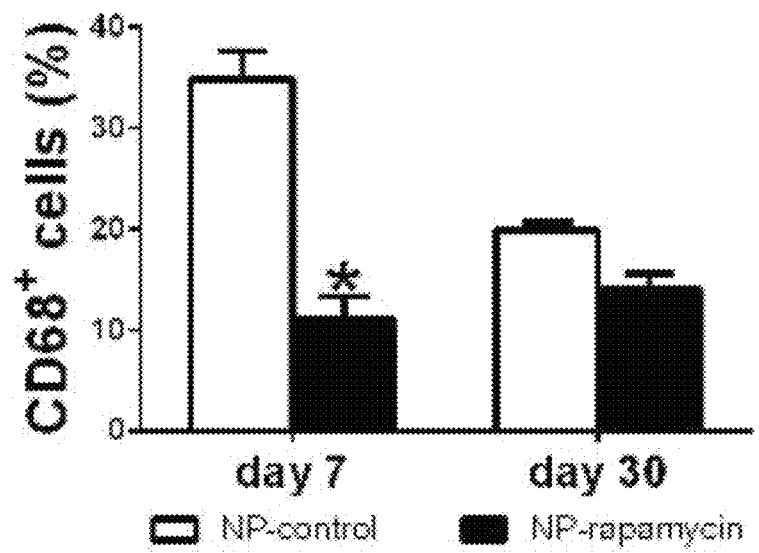
FIG. 6B is a bar graph showing the percent of CD68-positive cells at day 7 and day 30 after patch venoplasty from en-face staining of patches. *, P<0.0001, NP-rapamycin vs. NP-control; n=4.
Figure 6C:
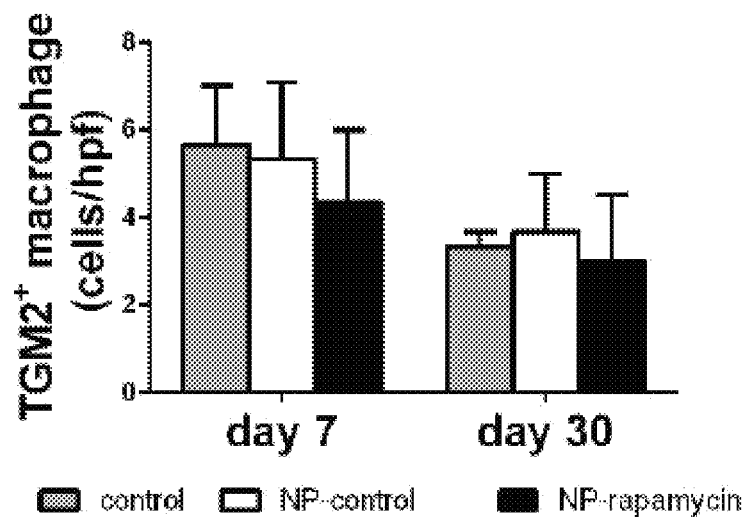
FIG. 6C is a bar graph showing the number of M2 macrophage marker transglutaminase 2, TGM2, positive macrophages per high power field at day 7 and day 30 after patch venoplasty; n=4-6; group, p=0.0235; time, p=0.7564.
Figure 6D:
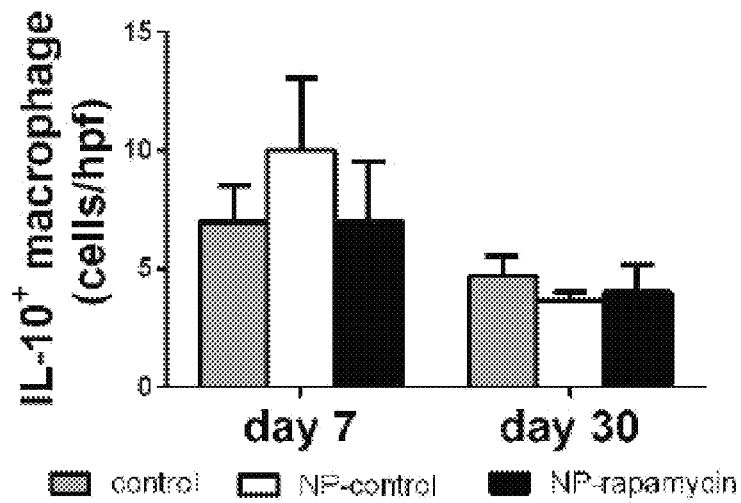
FIG. 6D is a bar graph showing the number of IL-10 positive macrophages per high power field at day 7 and day 30 after patch venoplasty; n=4-6; group, p=0.1479; time, p=0.7952.
Figure 6E:
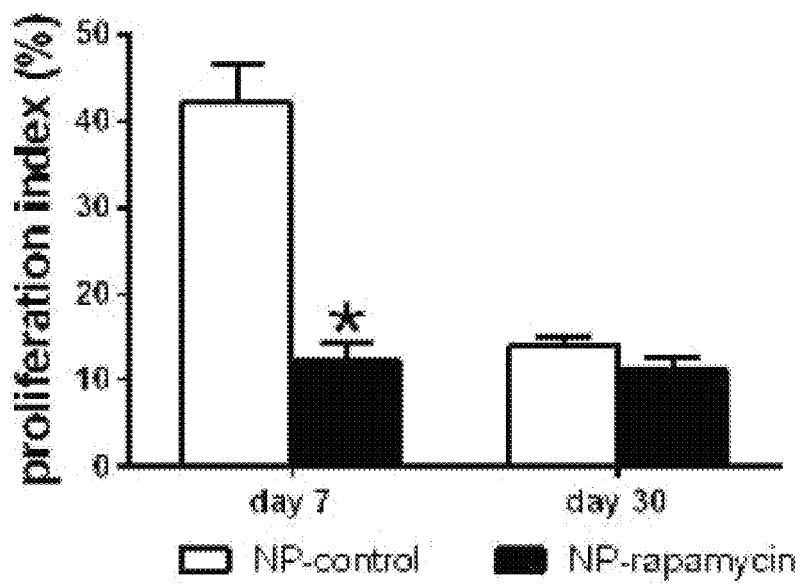
FIG. 6E is a bar graph showing the proliferation index at day 7 and day 30 after patch venoplasty. *, P<0.0001, NP-rapamycin vs. NP-control; n=4. From western blot band intensity normalization.
Figure 6F:
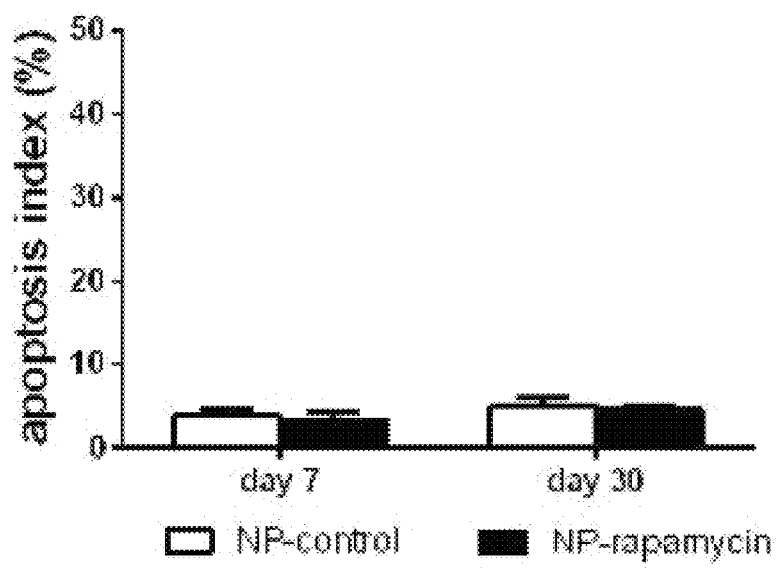
FIG. 6F is a bar graph showing apoptosis index at day 7 or day 30 after patch venoplasty. n=4. From western blot band intensity normalization.
Figure 6G:
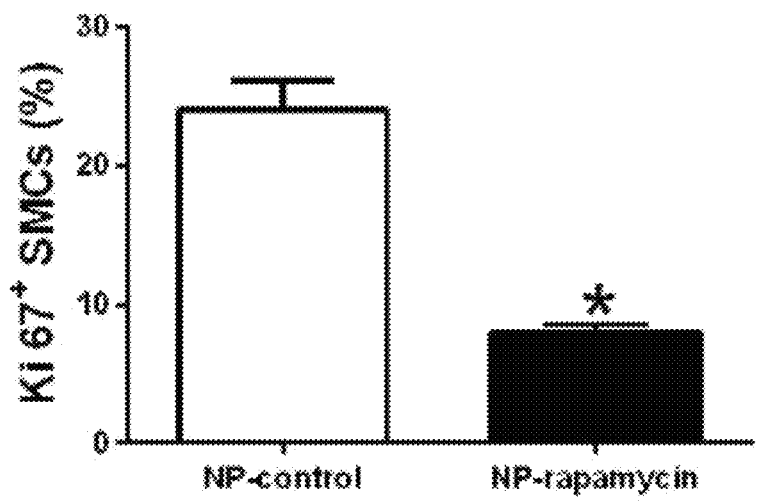
FIG. 6G is a bar graph showing the percentage of Ki67 and α-actin dually-positive cells in the neointima at day 7 after patch venoplasty; mean of 4 high power fields per patch; *, p=0.0018; n=4.
Figure 6H:
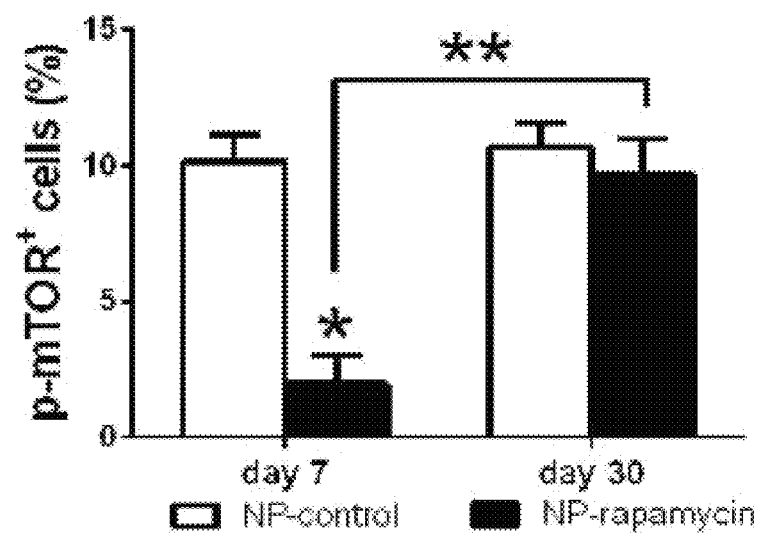
FIG. 6H is a bar graph showing percentage of p-mTOR positive cells at day 7 and day 30 after patch venoplasty. *, P=0.0025, NP-rapamycin vs. NP-control; **, P=0.0018; day 7 vs. day 30; n=4.

FIG. 6A demonstrates that the expression of α-actin is reduced in NP-rapamycin patches at both day 7 and day 30 compared to NP-control patches, with significantly lower SMC density in NP-rapamycin patches. FIG. 6B demonstrates that the expression of CD68 is decreased and that significantly fewer CD68-positive cells are present in NP-rapamycin patches at day 7. FIGS. 6C-6D demonstrate similar numbers of M2 type macrophages and IL-10 positive macrophages in NP-rapamycin patches as in NP-control patches and plain patches at both day 7 and day 30. FIG. 6E demonstrates that NP-rapamycin patches have less Ki67 expression and fewer proliferating cells at day 7 compared to NP-control patches. FIG. 6F demonstrates that the expression of cleaved caspase-3 and the number of apoptotic cells were similar in NP-rapamycin and NP-control patches at both days 7 and 30. FIG. 6G demonstrates that NP-rapamycin patches have fewer proliferating SMCs compared to NP-control patches at day 7. FIG. 6H demonstrates that the number of p-mTOR positive cells is smaller in NP-rapamycin patches compared with NP-control patches at day 7.

These studies demonstrate the use of tissue engineered drug delivery platforms, including covalently linked rapamycin-containing NP at the surface of a bovine pericardial patch commonly used in cardiovascular surgery. Using a venous patch angioplasty model that forms aggressive neointimal hyperplasia, patches with rapamycin-containing NP show reduced thickening. This modified patch is a novel composite delivery system that allows sustained site-specific delivery of therapeutics, and other active agents.

Pericardial patches, either bovine or porcine, are commonly used by surgeons to close blood vessels during open cardiovascular surgery (Muto, et al. *J Vasc Surg* 50, 206-213 (2009); Li, et al., *Annals of vascular surgery* 25, 561-568 (2011)).

Studies showed that the pericardial patch may be a unique niche microenvironment that attracts endothelial progenitor cells after implantation, promoting incorporation into the host vessel that may be responsible for long term durability and clinical success (Li, et al., *PLoS One* 7, e38844, doi:10.1371/journal.pone.0038844 (2012); Bal, et al., *J Vasc Surg* 63, 1063-1073 (2016)).

In the current study, NP were covalently linked to a pericardial patch; since these patches are primarily collagen fibers, the NP are conjugated throughout the patch in addition to the patch surface (see FIG. 1A), facilitating a localized and increased concentration profile of the released drug. In silico models have demonstrated that the nature and profile of this concentration gradient near a cell surface develops over time and space, although the upper limit of drug delivery is not known (Labowsky & Fahmy, *Nanomedicine*, 11, 1019-1028 (2015)). Covalent linkage of the NP allows delivery of therapeutic agents directly into the circulatory system with minimal shedding of the NP into the systemic circulation and most organs, although some NP can be found in the liver, kidney and spleen. In this study, a patch based on clinically-proven materials is used as a next-generation delivery system for the delivery of active agents in a sustained fashion at a specific site. The amount of drug deliverable on the patch depends on both the numbers of NP used in the coupling reaction (FIG. 1B), the porosity of the patch, as well as the size of the implanted patch. Other applications with other NP-drugs can be tailored, for example, to provide different NP-surface densities that can be customized as a function of the reagent delivered and/or the conjugation reaction conditions.

Placement of the patches in the venous system allows detection of off-target delivery of therapeutics, especially to the liver and lungs. Modification of the NP or the linkage systems can allow different kinetic profiles of drug delivery, potentially allowing targeted delivery to more distal locations. In addition, the more aggressive development of neointimal hyperplasia in venous systems provides a robust test of the delivery system (Kohler & Clowes, *Circ Res*, 69, 1557-1565 (1991); Shi, Q, et al., *Annals of vascular surgery* 12, 341-348, (1998)). Lastly, the composite prosthetic devices including bound nanoparticles for controlled drug delivery can limit or prevent restenosis even after drug delivery is reduced below therapeutic levels, e.g. after the drug is exhausted, since a patched site has less tendency for form restenosis, thereby increasing the translational potential of patch angioplasty (Ho, Nguyen & Menard, *J Vasc Surg* 55, 708-714 (2012); Mannheim, Weller, Vahadim, & Karmeli, *J Vasc Surg*, 41, 403-407 (2005); and Bond, et al., *J Vasc Surg*, 40, 1126-1135 (2004)). The construction and therapeutic application of the described drug delivery system provides prosthetic devices, such as pericardial patches, as a tissue engineering platform, and conjugation of NP containing therapeutics to collagen scaffolds represents a step forward in delivering therapeutics, both into the vascular system, and potentially downstream into target organs.

Example 6. Nanoparticle-Mediated TGF in Release from Pericardial Patches Decrease Angioplasty Pseudo-Aneurysm Formation In Vivo Materials and Methods Despite the numerous animal aneurysm models, there is still no animal model available that can recapitulate human patch angioplasty or anastomic pseudoaneurysm formation. A rat pericardial patch angioplasty model was developed to more precisely recapitulate the human patch angioplasty pseudoaneurysm. Methods to demonstrate that the TGF β pathway also plays a role in patch angioplasty pseudo-aneurysm formation were performed using a model for rat aorta pseudo-aneurysm after pericardial patch angioplasty.

Preparation of Composite Prosthetic Devices Including TGF-β1

Pericardial patches were covalently modified using NP loaded with TGF-β1. TGF-β1 (4 µg) was dissolved in PBS (200 µL) and added to chloroform (2 mL) containing carboxylated poly(lactic-coglycolic acid) (PLGA) (100 mg). The mixture was then added drop-wise to 5% polyvinyl alcohol (PVA) (4 mL) and sonicated three times to form NP. The NP were dispersed in 0.2% PVA solution (200 mL) to evaporate the solvent for 2 h while stirring (40 ng TGF-β1/mg NP, encapsulation efficiency 10%). Patches (7 mm×5 mm) were conjugated with the NP using ethyl (dimethyl-aminopropyl) carbodiimide/N-hydroxysuccinimide (EDC/NHS) chemistry, as discussed above. EDC (20 µmol/mL) and NHS (10 µmol/mL) were dissolved in MES solution (0.1 M; pH 5) for the conjugation. Carboxyl groups on the NP were activated using EDC (1 mL) for 30 min and substituted with NHS by adding NHS (1 mL) for 30 min. The solution pH was raised from 5 to 8 using NaOH (1 M). Patches were then placed into the activated NP suspension and incubated at 37° C. overnight. To assess TGF-β1 release from NP patches in vitro, the patches were incubated in PBS at 37° C. The supernatant was collected at the desired time points and used to quantify TGF-β1 using a Micro BCA Protein Assay Kit (Thermo Fisher Scientific).

Mouse Lung Endothelial Cell Culture

Mouse lung endothelial Cells (MLECs, passage 3-6) were cultured in endothelial basal medium 2 (EBM-2) with endothelial cell growth media-2 MV SingleQuot Kit Supplement & Growth Factors (Lonza), consisting of 20% FBS (Gibco) and 1% penicillin/streptomycin (Gibco), 2 mM L-glutamine (Corning Life Sciences). When MLECs reached approximately 80% confluence, changed the medium to FBS free blank EBM-2 medium for 12 h, then NP and NP-TGF-β1 (5 μmol/ml) were added to the cells in the 6-well plate for 1 h at room temperature. After treatment, washed the MLECs by cold PBS twice, then extracted cell lysate for further Western blot.

Animal Model

Male Wistar rats (6-8 week old) were used for patch implantation (n=92). Microsurgical procedures were performed as previously described (Bai, et al., *J Vis Exp* (2017)) Rats were sacrificed on postoperative 0 h, 1 h, 6 h, 24 h, days 7, or 30 and the patches and organs explanted for analysis. No immunosuppressive agents, antibiotics or heparin were given at any time.

Histology

Rats were anesthetized with isoflurane inhalation, and tissues were fixed by transcardial perfusion of phosphate buffered saline (PBS) followed by 10% formalin. Tissue was removed and fixed overnight in 10% formalin followed by a 24-hour immersion in 70 percent alcohol. Tissue was then embedded in paraffin and sectioned (5 μm thickness). Tissue sections were de-paraffinized and stained with hematoxylin and eosin.

Assessment of pseudo-aneurysm formation was carried by microscopy observation of tissue sections of rat native aorta, patch angioplasty with normal healing and without pseudoaneurysm formation, small pseudoaneurysm formation and large pseudoaneurysm formation, showing macroscopic features of pseudoaneurysms 30 days after rat aorta patch angioplasty and using Verhoeff-Van Gieson (VVG) staining.

Immunohistochemistry

Tissue sections were de-paraffinized and then incubated using primary antibodies overnight at 4° C. After overnight incubation, the sections were incubated with EnVision reagents for 1 h at room temperature and treated with Dako Liquid DAB Substrate Chromogen System (Dako). Finally, the sections were counterstained with Dako Mayer's Hematoxylin, Immunofluorescence Tissue sections with rhodamine were de-paraffinized and examined under the immunofluorescence microscope directly. Otherwise, tissue sections were de-paraffinized and then incubated with primary antibodies overnight at 4° C. To visualize and quantify cells, sections were stained with the fluorescent dye 4', 6-diamidino-2-phenylindole (DAPI; Invitrogen) to mark cellular nuclei.

Western Blot

Cells were crushed and mixed with buffer including protease inhibitors (Roche, Complete Mini 12108700) prior to sonication (5 sec) and centrifugation (135,000 rpm, 15 min). Equal amounts of protein from each experimental group were loaded for SDS-PAGE, followed by Western blot analysis with signals detected using the ECL detection reagent. Pseudo-aneurysm tissues were harvested from the animals, each sample was analyzed individually, without combination of samples.

Primary antibodies included: anti-α-actin (Abcam, ab5694; IHC and IF, 1:100); anti-cleaved Caspase-3 (Cell Signaling #9661; IHC, 1:50; WB, 1:1,000); anti-CD68 (ED1; Abcam, ab31630; IHC, 1:200); anti-GAPDH (Cell Signaling, 14C10; WB, 1:2,000); anti-IL-10 (Abcam, ab9969; IF, 1:100); anti-transglutaminase 2 (TGM2; #37557; IF, 1:100); Secondary antibodies used for IF were: donkey anti-goat Alexa-Fluor-488, donkey anti-rabbit Alexa-Fluor-488, donkey anti-rabbit Alexa-Fluor-568, donkey anti-mouse Alexa-Fluor-568 and chicken anti-mouse Alexa-Fluor-488 conjugated antibodies from Invitrogen (1:1,000). For IHC, sections were incubated with EnVision reagents for 1 h at room temperature and treated with Dako Liquid DAB+ Substrate Chromogen System (Dako). Finally, the sections were counterstained with Mayer's hematoxylin.

Results

Pseudoaneurysm Formed after Rat Aorta Pericardial Patch Angioplasty

A rat aorta pericardial patch angioplasty pseudoaneurysm formation model that can mimic the development of a human patch angioplasty pseudoaneurysm was developed. Sustained release of TGF-β1 from the composite prosthetic patches was observed for 2-3 weeks in vitro. After pericardial patch angioplasty, a small number of the patches healed normally without dilation or pseudoaneurysm formation, however a large number of patches healed with aortic dilation and pseudoaneurysm formation.

Figures 7A, 7B:
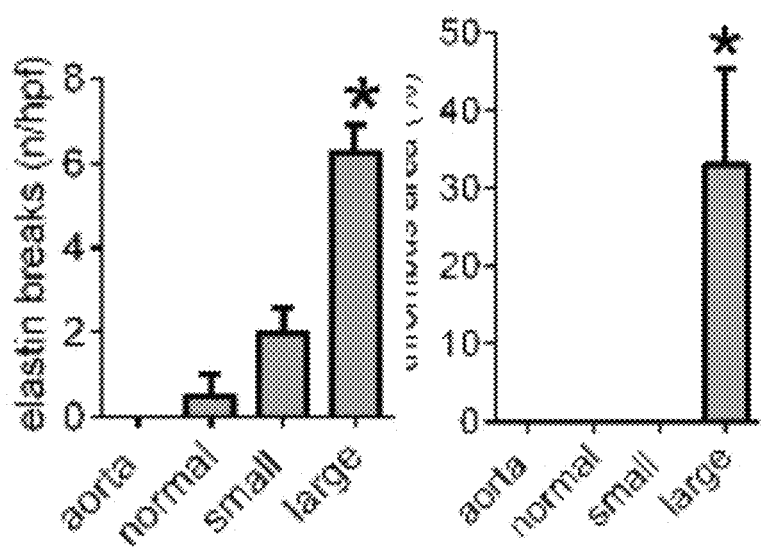
FIGS. 7A-7F are bar graphs, showing elastin breaks per high power field (n/hpf; 0-8) for each of aorta, normal, small and large, respectively (*, p=0.005, vs. small) (FIG. 7A); % thrombus area (0-50%), for each of aorta, normal, small and large, respectively (* p=0.0394, vs. small) (FIG. 7B); the number of CD68 positive cells per high power field (n/hpf; 0-80) for each of aorta, normal, small and large, respectively (* p=0.0006, vs. small) (FIG. 7C); the number of CD45 positive cells per high power field (n/hpf; 0-80) for each of aorta, normal, small and large, respectively (* p=0.004, vs. small) (FIG. 7D); the proliferation index in the pseudoaneurysm wall (%) for each of aorta, normal, small and large, respectively (* p<0.0001, vs. none and small) (FIG. 7E); and the % apoptosis index in the pseudoaneurysm wall (0-40%) for each of aorta, normal, small and large, respectively (* p=0.0006, vs. none and small) (FIG. 7F).
Figures 7C, 7D:
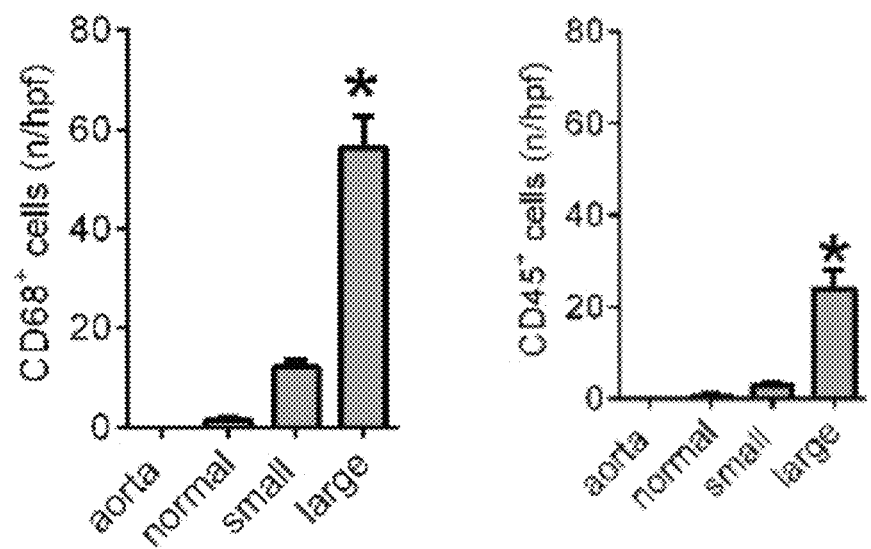
Figure 7E:
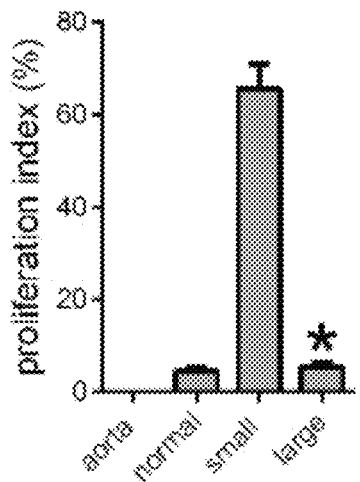
Figure 7F:
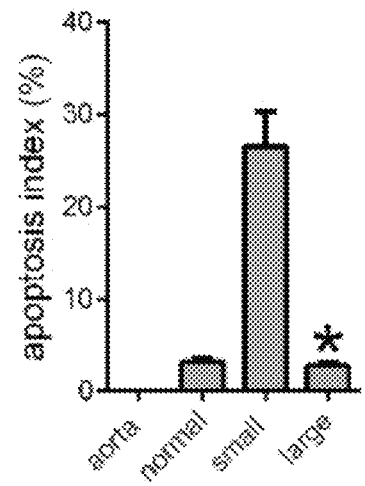

A neointima formed on the luminal side of the patch in the normal healing and small pseudoaneurysm groups; mural thrombus formed in the large pseudoaneurysm group (as observed by microscopy and VVG staining of tissue sections). The lumen area varied widely in the pseudoaneurysm. In the normal aorta and normal healing groups, the elastin fibers were continuous without breaks, but in the small and large pseudoaneurysms, the elastin fibers were discontinuous and broken, especially in the large pseudoaneurysms; the large pseudoaneurysm also lost the normal smooth muscle cells in the wall. There were more elastin fibers breaks in the large pseudoaneurysm compared to the small pseudoaneurysm (FIG. 7A); and there was also a larger thrombus area in the large pseudoaneurysm lumen (FIG. 7B). There were more macrophages in the large pseudoaneurysm compared to the small pseudoaneurysm (FIG. 7C, 7D). There were both increased proliferation and apoptosis index in the small pseudoaneurysm but a decreased proliferation and apoptosis index in the large pseudoaneurysm (FIGS. 7E, 7F). The increased macrophage phenotype via immunofluorescence was further examined, which showed more CD68 and iNOS dual positive cells, both in the neointima and wall, in the large pseudoaneurysm; there were few CD68 and TGM2, CD68 and IL10 dual positive cells. In the normal healing and small pseudoaneurysms, there were some vWF as well as collagen-1 dual positive endothelial cells, but there were fewer collagen-1 positive endothelial cells in the large pseudoaneurysm.

Canonical and Noncanonical Pathway was in a Dynamic Change Process in the Pseudoaneurysms after Patch Angioplasty Changes in the TGF-β1 canonical and non-canonical pathways in the formation of pseudoaneurysm were examined. It was established that TGF β1 canonical and noncanonical pathways both play an important role in the formation of pseudoaneurysms.

Figure 8A:
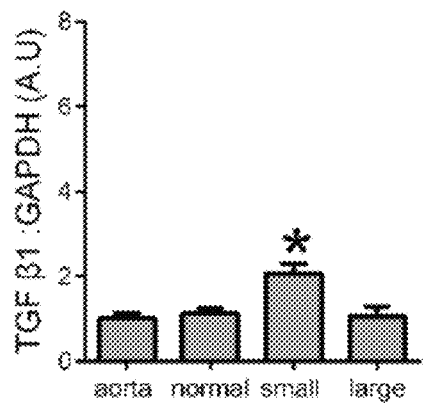
FIGS. 8A-8J are bar graphs, showing the ratio of TGF β1:GADPH (A.U) for each of aorta, normal, small and large pseudoaneurysms, respectively (*, p<0.02) (FIG. 8A); the ratio of TGFBR1:GADPH (A.U) for each of aorta, normal, small and large pseudoaneurysms, respectively (* p<0.02, for aorta vs. normal; ** p=0.0132, for small) (FIG. 8B); the density of TGF β1 (A.U.) for each of aorta, normal, small and large pseudoaneurysms, respectively (* p<0.0001, vs. normal and small) (FIG. 8C); the TGFBR1 positive cells in the pseudoaneurysm wall per high power field (n/hpf; 0-150) for each of aorta, normal, small and large pseudoaneurysms, respectively (* p<0.0001, for none vs. small) (FIG. 8D); the ratio of phospho vs. total smad2 (A.U.) for each of aorta, normal, small and large pseudoaneurysms, respectively (* p<0.0001) (FIG. 8E); the ratio of phosphor vs. total TAK1 (A.U.) for each of aorta, normal, small and large pseudoaneurysms, respectively (* p<0.002) (FIG. 8F); % vWF and p-Smad2 dual positive cells in the aorta wall (0-100%) for each of aorta, normal, small and large pseudoaneurysms, respectively (* p=0.0488, vs. large; **, p=0.0154, vs. normal) (FIG. 8G); % α-actin and p-smad2 dual positive cells in the wall (0-80%) for each of aorta, normal, small and large pseudoaneurysms, respectively (* p<0.003, vs. normal and large) (FIG. 8H); number of CD68 and p-smad2 dual positive cells in the wall per high power field (n/hpf; 0-15) for each of aorta, normal, small and large pseudoaneurysms, respectively (* p=0.003, vs. normal and large) (FIG. 8I); and % vWF and TAK1 dual positive cells in the aorta wall (0-100%) for each of aorta, normal, small and large pseudoaneurysms, respectively (* p<0.0001, vs. normal) (FIG. 8J).
Figure 8B:
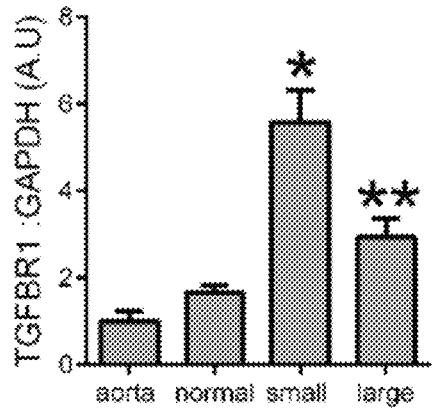
Figure 8C:
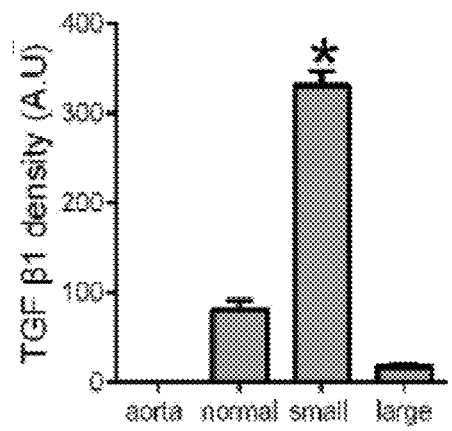
Figure 8D:
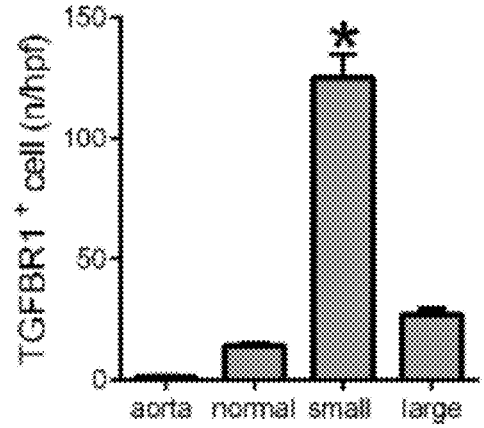
Figure 8E:
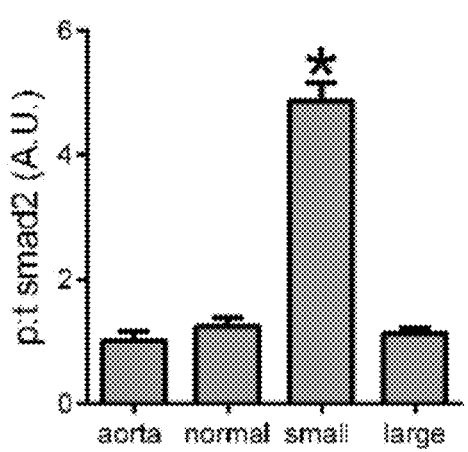
Figure 8F:
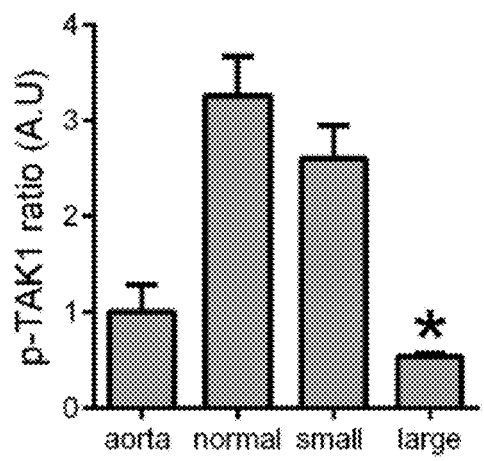
Figure 8G:
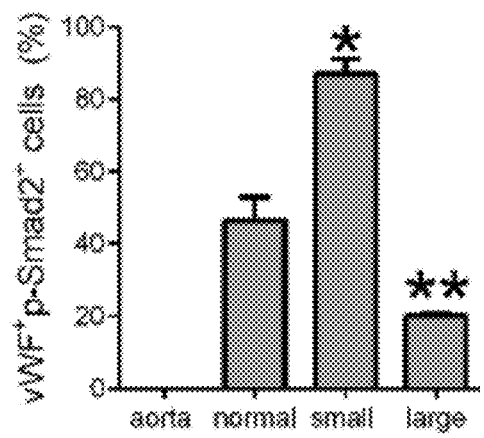
Figure 8H:
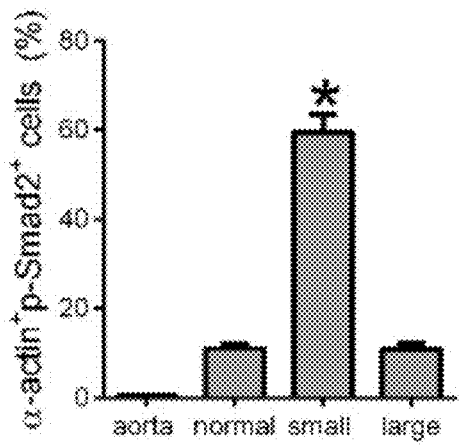
Figure 8I:
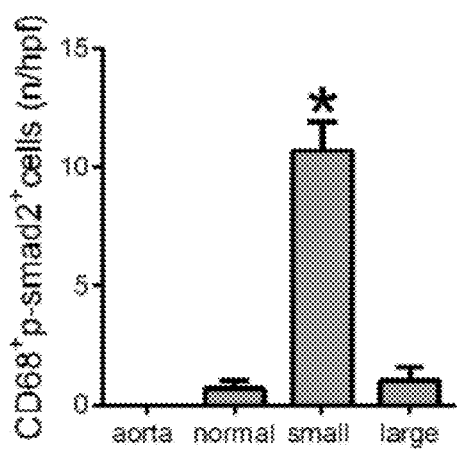
Figure 8J:
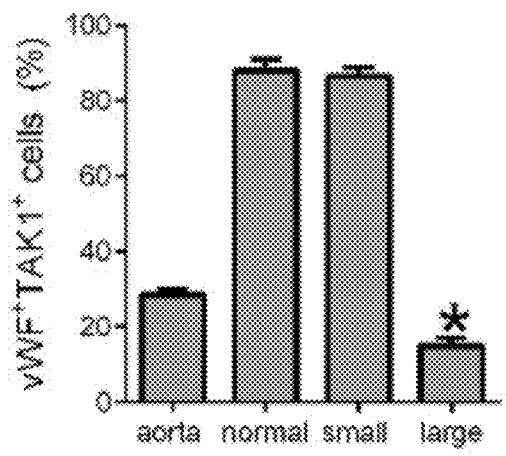

Western blot showed a higher TGF-β1 expression in the small pseudoaneurysms (FIG. 8A); TGFBR1 (TGF-β receptor 1) also increased in the small pseudoaneurysms but decreased in the large pseudoaneurysms (FIG. 8B). Near the anastomosis area of the patch, immunofluorescence showed more TGF β1 positive cells in the small pseudoaneurysm than in the large pseudoaneurysm (FIG. 8C); in the pseudoaneurysm wall, immunofluorescence also detected a higher TGFBR1 expression in the small pseudoaneurysm (FIG. 8D). In the canonical pathway, phospho-smad2 and total smad2 was low in the normal aorta, slightly increased in the normal healing, and largely increased in the small pseudoaneurysm; however, there was an obvious decrease of phospho-smad2 and total smad2 in the large pseudoaneurysm, with a similar total smad2 expression (FIG. 8E). In the noncanonical pathway, phospho-TAK1 and total TAK1 was low in the normal aorta, dramatically increased in the normal healing and small pseudoaneurysm, there was an obvious decrease of phospho-TAK1 in the large pseudoaneurysm (FIG. 8F). Immunofluorescence showed a continuous presence of vWF positive endothelial cells in the neointima and pseudoaneurysm wall in the normal healing and small pseudoaneurysm groups; conversely, there was a discontinuous and weak expression of vWF positive endothelial cells in the large pseudoaneurysm neointima and pseudoaneurysm wall). Phospho-smad2 can be detected in most of the neointimal and wall endothelial cells of the normal healing and small pseudoaneurysm, but there were fewer phospho-smad2 positive endothelial cell in the large pseudoaneurysms (FIG. 8G); there were also increased p-smad2 positive smooth muscle cells in the small pseudoaneurysm but a decreased number in the large pseudoaneurysm (FIG. 8H); there were also increased p-smad2 positive macrophages in the small pseudoaneurysm (FIG. 8I); TAK1 can also be detected in most of the neointimal and wall endothelial cells in the normal and small pseudoaneurysms, but there were fewer TAK1 positive endothelial cell in the large pseudoaneurysms (FIG. 8J). As for the neointima, the TGFBR1 positive cells, dual vWF and p-smad2 positive cells, dual α-actin and p-smad2 positive cells, dual CD68 and p-smad2 positive cells and dual vWF and TAK1 positive cells showed a similar change pattern.

The Canonical Pathway Plays a Complicated Role in Aortopathies

Phosphorylated-smad2 was found to be lowly expressed in the normal aorta and aorta dissection, but highly expressed in the aorta aneurysm (Gomez, et al., *Arterioscler Thromb Vasc Biol*, 33:2222-2232(2013); Gomez, et al., *J Pathol* 218:131-142(2009)). These studies demonstrate dynamic change of phosphorylated-smad2 in the patch angioplasty pseudoaneurysms formation process: there was a dramatic increase of phosphorylated-smad2 in the small pseudoaneurysm, but a decrease in the large pseudoaneurysm. These different changes may represent the complex role of phosphorylated-smad2 in the pseudoaneurysm formation. Compensation or decompensation of phosphorylated-smad2 play different roles in different stages of pseudoaneurysm formation. In noncanonical pathway, transforming growth factor-β-activated kinase 1 (TAK1) is a mitogen-activated protein 3-kinase and an AMP activated protein kinase (AMPK) kinase (Zippel, et al., *Arterioscler Thromb Vasc Biol*, 33:2792-2799 (2013)). TAK1 is critical in vascular formation, as embryos deficient in TAK1 develop dilated capillary networks. Additionally, TAK1 plays a role in cell migration and tube formation (Morioka, et al., *Blood.*; 120:3846-3857(2012)). Although the canonical pathway has long been investigated in regard to aneurysm formation (Schoenhoff, *E Bio Medicine.* 12:26-27 (2016)) the role of TAK1 in pseudoaneurysm formation has not been examined; perhaps because TAK1-null mice die at embryonic day 11.5 with significant vascular defects. The patch angioplasty model was used to establish that TAK1 phosphorylation, like smad2 phosphorylation, is also involved in a dynamic change process.

Nanoparticle-TGF β1 Patch Decrease Angioplasty Pseudoaneurysm Formation

It has been established that using nanoparticle-TGF β1 covalent pericardial patch can decrease the occurrence and progression of the psudoaneurysm formation.

Figure 9A:
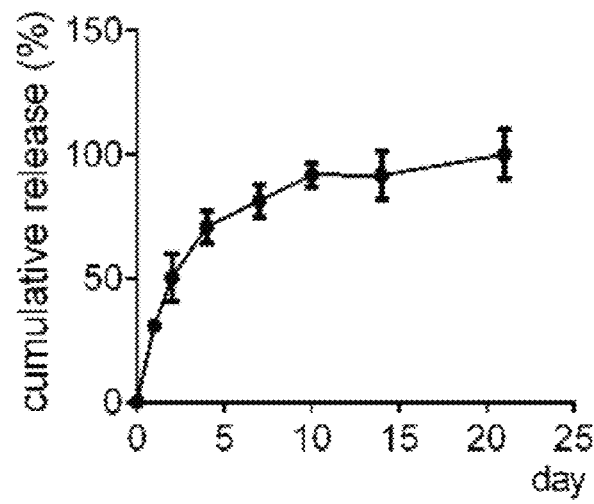
FIG. 9A is a line graph showing cumulative release (%) of TGF β1 from nanopartilces (NP) over time (0-21 days).
Figure 9B:
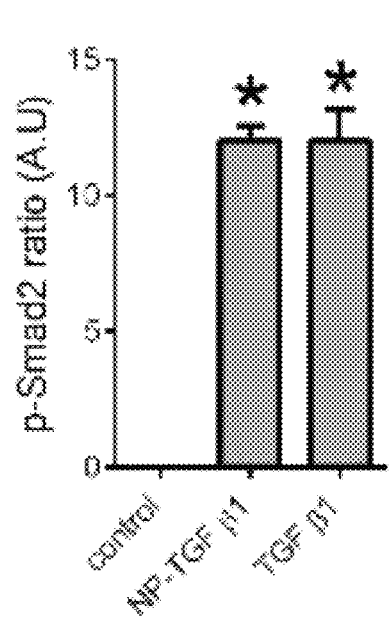
FIGS. 9B-9G are bar graphs, showing the ratio of phospho vs. total smad2 (A.U.) for each of for each of nanoparticle (NP) control, and NP-TGF β1, respectively (* p<0.0001, vs. control) (FIG. 9B); the pseudoaneurysm formation in control, NP-control and NP-TGF β1 patches, day 30 (FIG. 9C); the number of elastin breaks per high power field in control, for each of NP-control and NP-TGF β1 patches, at day 30 (* p<0.001) (FIG. 9D); the number of CD68 positive cells (* p<0.001) (FIG. 9E); the proliferation index in the pseudoaneurysm wall (FIG. 9F); and the proliferation index in the pseudoaneurysm wall. n=4-6 (FIG. 9G).
Figure 9C:
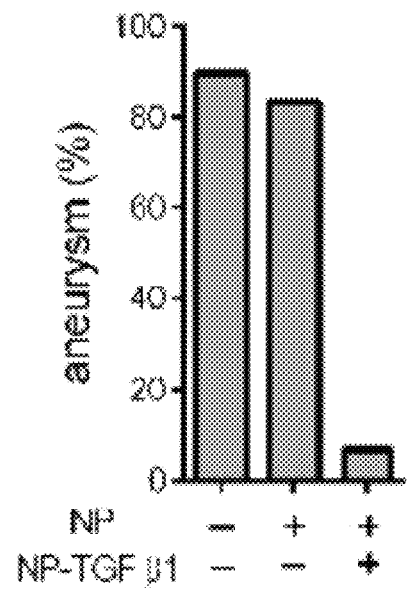
Figure 9D:
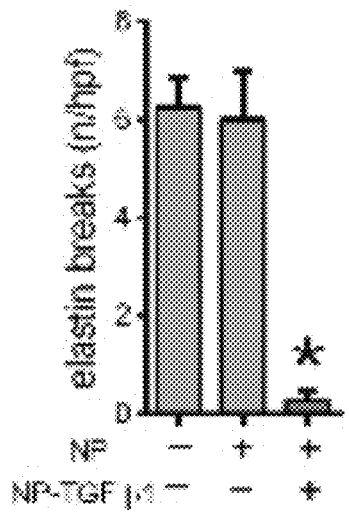
Figure 9E:
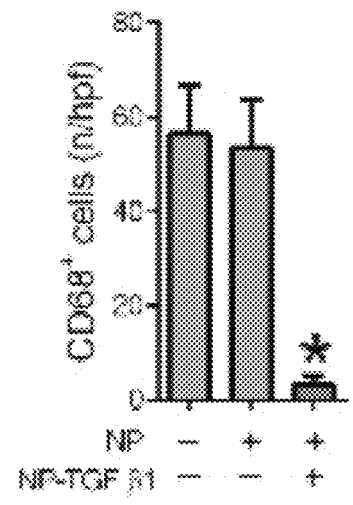
Figure 9F:
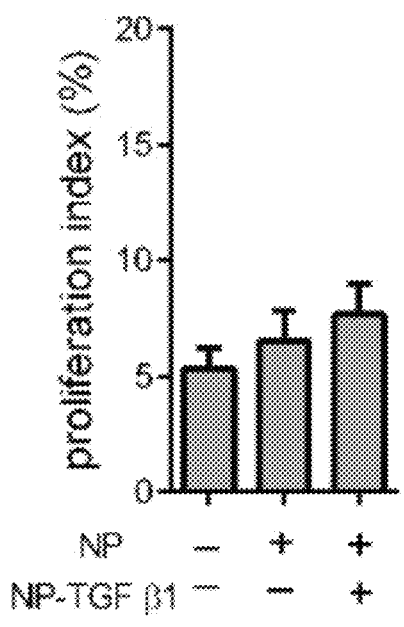
Figure 9G:
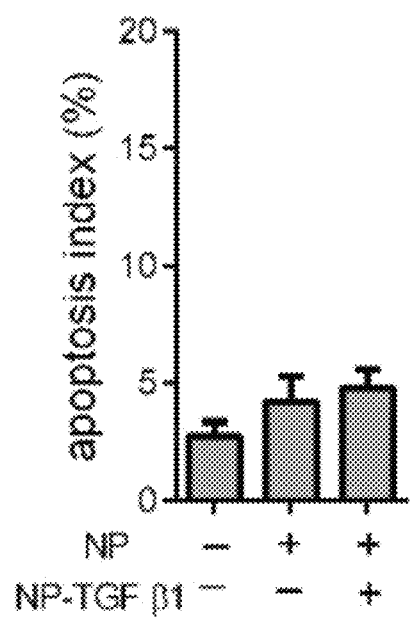

First, the release of nanoparticles from a nanoparticle-rhodamine patch was tested in an arterial environment. The patch became red upon nanoparticle-rhodamine conjugation and the nanoparticle-rhodamine conjugated patch showed a much higher level of fluorescence compared to the control patch. After nanoparticle-rhodamine patches were harvested at 1 h, 6 h and 24 h, there was no difference in the structure, as showed by HE staining. Direct fluorescence examination showed rhodamine particles released from the patch to the luminal side, outer surface and contralateral aorta wall. There was also an increase in rhodamine particles with time. Cumulative release of TGF β1 showed the release was highest in the first 5 days and slowly decreased until 21 days (FIG. 9A). In MLEC cells, nanoparticles containing TGF β1 (NP-TGF (31) and TGF β1 showed similar levels of phospho-smad2 as well as total smad2 (FIG. 9B). After implantation of patches into the rat aorta, there was a similar pseudoaneurysm formation, similar pseudoaneurysm lumen area and a similar pseudoaneurysm rate in the control and NP-control group, but only one in fifteen pseudoaneurysms formed after NP-TGF β1 conjugated patch implantation (FIG. 9C). In the nanoparticle-TGF β1 group, there was also neoimtimal formation. There were almost no elastin breaks in the NP-TGF β1 group (FIG. 9D). There were significantly fewer macrophages in the nanoparticle-TGF β1 group compared to the control and NP-control group (FIG. 9E). α-actin staining showed more smooth muscle cells in the nanoparticle-TGF β1 group compared to the pseudoaneurysm in the NP-control group. There were a similar proliferation index and similar apoptosis index in the NP-TGF β1 group compared to the NP-control group (FIGS. 9F, 9G), and similar proliferation and apoptosis index in the neointima. There were also more CD68 and iNOS dual positive cells in the pseudoaneurysm in the NP-control group, with few CD68 and TGM2, CD68 and IL 10 dual positive cells compared to the NP-control group. There were also more vWF and collagen-1 dual positive endothelial cells in the NP-TGF β1 group compared to the control and NP-control group. Western blot showed a tendency of TGF β1 increase in the NP-TGF β1 group; and a significantly increase of TGFBR1 in the NP-TGF β1 group (FIGS. 10A and 10B). In the pseudoaneurysm wall, there was more TGF (31 expression and more TGFBR1 positive cells in the NP-TGF-β1 group compared to the NP-control group (FIGS. 10C and 10D). Western blot showed an increased p-smad2 and p-TAK1 in the NP-TGF β1 group compared to the NP-control group (FIGS. 10E and 10F). Immunofluorescence showed more dual vWF and p-smad2 positive cells (FIG. 10G), dual α-actin and p-smad2 positive cells (FIG. 10H), dual vWF and TAK1 positive cells in the NP-TGF β1 group compared to the NP-control group (FIG. 10I); but a similar dual CD68 and p-smad2 positive cells (FIG. 10J). The neointima showed a similar change pattern.

Macrophages play a role in the aneurysm formation, progression and healing. M1 macrophages are initially recruited to the site of injury and produce proteases and proinflammatory cytokines, while M2 macrophages produce anti-inflammatory cytokines and extracellular matrix (ECM) components. Injection of M2-polarized macrophages reduced aortic dilation after aneurysm induction (Dale, et al., *J Immunol*, 196:4536-4543 (2016)), M1 macrophages are also required in a murine cerebral aneurysm formation model. In humans, M1 is also found to be markedly increased in ruptured aneurysms (Hasan, et al., *J Neuroinflammation*, 9:222 (2012).

In this study, M1 macrophages significantly increase in the large pseudoaneurysm, but M2 macrophages were similarly expressed when compared to the control (none) and small pseudoaneurysm samples. Prior research showed that lack of TGFβ signaling, at physiological levels, affects M2 polarization (Gong, et al., *BMC Immunol* 13:31 (2012)). TGFβ can induce M2 like macrophage polarization (Zhang, et al., *Oncotarget*, 7:52294-52306 (2016)). Mice In the NP-TGF (3 group had fewer M1 macrophages compared to the NP-control group. There maybe two reasons for the decreased M1 macrophages in the NP-TGF β group: one could be that the normal healing without pseudoaneurysm formation, and the other could be that TGF β released from the patch inhibits M1 macrophage activation.

The data described in this study show that nanoparticle-TGF-β1 can efficiently stimulate smad2 phosphorylation in vitro and also stimulate smad2 phosphorylation in vivo. These results indicate nanoparticle-TGF β1 pericardial patches can decrease the patch angioplasty pseudoaneurysm formation when used in vascular surgery.

In summary, this work demonstrates that the pericardial patch angioplasty pseudoaneurysm formation model effectively mimics human patch angioplasty pseudoaneurysm. In addition, delivery of TGF β1 using nanotechnology can effectively decrease the pseudoaneurysm formation, which shows a promising application in vascular surgery (FIG. 12).

Example 7. Nanoparticle-Mediated SB431542 Release from Pericardial Patches Induces Pseudoaneurysm Formation In Vivo Preparation of Composite Prosthetic Devices Incorporating SB431542

Pericardial patches were covalently modified using NP loaded with SB431542. SB431542 (5 mg) was dissolved in PBS (200 μL) and added to chloroform (2 mL) containing carboxylated poly(lactic-coglycolic acid) (PLGA) (100 mg). The mixture was then added drop-wise to 5% polyvinyl alcohol (PVA) (4 mL) and sonicated three times to form NP. The NP were dispersed in 0.2% PVA solution (200 mL) to evaporate the solvent for 2 h while stirring (40 ng TGF-β1/mg NP, encapsulation efficiency 10%). Patches (7 mm×5 mm) were conjugated with the NP using ethyl (dimethylaminopropyl) carbodiimide/N-hydroxysuccinimide (EDC/NHS) chemistry, as discussed above.

Mouse Lung Endothelial Cell Culture Mouse lung endothelial Cells (MLECs, passage 3-6) were cultured in endothelial basal medium 2 (EBM-2) with endothelial cell growth media-2 MV SingleQuot Kit Supplement & Growth Factors (Lonza), consisting of 20% FBS (Gibco) and 1% penicillin/streptomycin (Gibco), 2 mM L-glutamine (Corning Life Sciences). When MLECs reached approximately 80% confluence, changed the medium to FBS free blank EBM-2 medium for 12 h, then NP and SB431542 (5 μmol/ml) were added to the cells in the 6-well plate for 1 h at room temperature. After treatment, washed the MLECs by cold PBS twice, then extracted cell lysate for further Western blot.

Nanoparticle-SB431542 Conjugated Patch Induce Early Pseudoaneurysm Formation

Figure 11C:
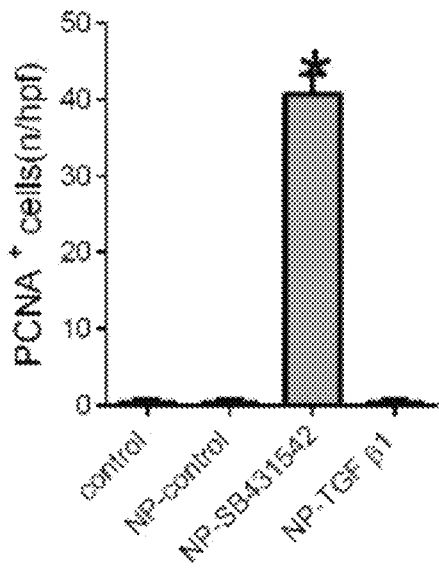
Figure 11D:
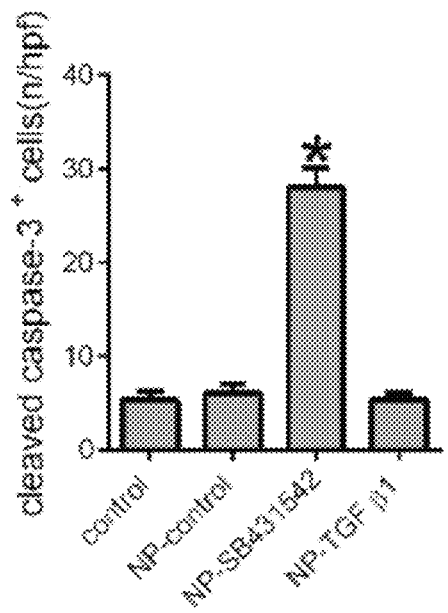

In the MLECs, nanoparticle-SB431542 decreased smad2 phosphorylation without a change in smad2 expression (FIG. 11A). There was no pseudoaneurysm formation in the control, nanoparticle control and nanoparticle-TGF β1 groups at day 7, but more than half of the samples developed a pseudoaneurysm in the nanoparticle-SB431542 group (FIG. 11B). The size of a pseudoaneurysm in the nanoparticle-SB431542 group varied widely, as demonstrated using a heat map. The elastin fibers were broken and discontinuous in the nanoparticle-SB431542 group compared to the other groups; immunohistochemistry showed that the expression of α-actin is similar in the control, NP-control and NP-TGF β1 groups, but is disordered in the NP-SB31542 group; Immunofluorescence and immunohistochemistry showed a high level of cell turnover in the NP-SB431542 group compared to control, NP-control and NP-TGF β1 group (FIGS. 11C, 11D). Immunofluorescence showed an increased number of CD68 and iNOS dual positive cells in the NP-SB431542 group, and there were few CD68 and TGM2, CD68 and IL-10 dual positive cells in control, NP-control and NP-TGF β1 groups.

Figure 11E:
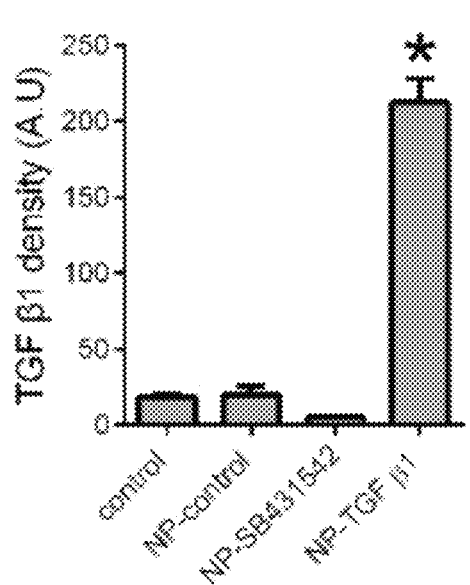
Figure 11F:
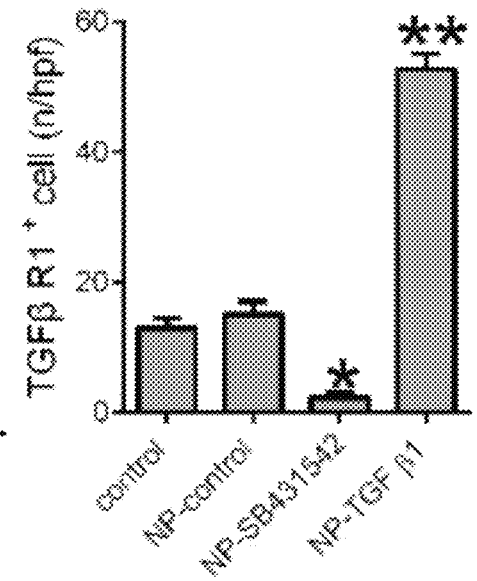

Immunohistochemistry showed collagen-1 strongly stained positive in the adventitia in the control, NP-control and NP-TGF β1 groups, but weakly in the NP-SB431542 group. Immunofluorescence showed TGF β1 deceased in the NP-SB431542 group, and increased in the NP-TGF β1 group (FIG. 11E). The number of TGFR1 positive cells also deceased in the NP-SB431542 group, but increased in the NP-TGF β1 group (FIG. 11F). Immunohistochemistry showed that for phospho-smad2 positive cells, there was a similar number in the control and nanoparticle control groups, a larger number in the nanoparticle-TGF β1 group, and a decreased number in the nanoparticle-SB431542 group (FIG. 11G). TAK1 showed a higher expression in the NP-TGF β1 group and a lower expression in the NP-SB31542 group (FIG. 11H).

These data demonstrate that the nanoparticle-SB431542 patch can induce pseudoaneurysm formation as early as day 7. These studies showed that nanoparticle-SB431542 decreased smad2 phosphorylation, both in vitro and in vivo, and can induce an early pseudoaneurysm formation (FIG. 12).

Unless defined otherwise, all technical and scientific terms used herein have the same meanings as commonly understood by one of skill in the art to which the disclosed embodiments belong. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A prosthetic device comprising covalently-bound particles encapsulating one or more therapeutic, prophylactic or diagnostic agents, covalently bound within and/or to the surface of the device,
   wherein the particles are covalently bound at a surface density between 0.01 and 1,000 μg/mm$^2$ or
   wherein the particles encapsulate between 1 ng and 1 μg of the agent per 1 μg of particles, wherein the particles release the one or more agents at a defined rate in vivo following implantation or administration of the device into a subject.

2. The prosthetic device of claim 1, wherein the device is a prosthetic patch selected from the group consisting of a vascular patch, a cutaneous patch, a cardiac patch, and a thoracic patch.

3. The prosthetic device of claim 2, wherein the prosthetic patch comprises natural polymers or decellularized extracellular matrix.

4. The prosthetic device of claim 1, wherein the device is a patch selected from the group consisting of a bovine pericardium patch, a porcine pericardial patch, an autologous venous tissue patch, and a thoracic patch.

5. The prosthetic device of claim 1 wherein the particles comprise one or more biodegradable polymers.

6. The prosthetic device of claim 1 wherein the particles comprise one or more polymers selected from the group consisting of poly(lactide-co-glycolide) (PLGA), poly(lactic acid) or polylactide (PLA), poly(c-caprolactone) (PCL), poly(glycolic acid) or polyglycolide (PGA), poly(D-lactic acid) or poly(D-lactide) (PDLA), poly(L-lactic acid) or poly(L-lactide) (PLLA), polyanhydrides, and poly(ortho esters).

7. The device of claim 1, wherein the particles are nanoparticles or microparticles with a mean diameter of between 1 nm and 1,000 μm, inclusive.

8. The device of claim 6, wherein the particles are covalently bound at a surface density between 0.01 and 1,000 μg/mm².

9. The device of claim 8, wherein the particles encapsulate between 1 ng and 1 μg of the agent per 1 μg of particles.

10. The prosthetic device of claim 1, wherein the particles encapsulate a therapeutic or prophylactic active agent selected from the group consisting of antiplatelet agents, anticoagulant agents, anti-inflammatory agents, antimicrobial agents, anti-metabolic agents, anti-neointima agents, immune-modulators, anti-proliferative agents, agents that affect migration and extracellular matrix production, agents that affect platelet deposition or formation of thrombus, and agents that promote vascular healing and re-endothelialization.

11. The device of claim 10, wherein the particles encapsulate an amount of therapeutic or prophylactic active agent effective to treat or prevent one or more symptoms of a disease or disorder in the subject.

12. The device of claim 10, wherein the total amount of the therapeutic or prophylactic active agent is between about 1 ng and 1,000 μg, inclusive.

13. The device of claim 10, wherein the particles release the one or more agents in vivo at a constant rate following implantation or administration of the device.

14. The device of claim 10, wherein the particles release the one or more agents in vivo over a period of between one and 31 days following implantation or administration of the device.

15. The device of claim 10, wherein the particles release the one or more agents in vivo over a period of between one and 24 hours following implantation or administration of the device.

16. The device of claim 8, wherein the device comprises
  (a) particles that release one or more agents at a constant rate in vivo over a period of one and 24 hours; and
  (b) particles that release one or more agents at a constant rate in vivo between one and 31 days following implantation or administration of the device.

17. The device of claim 1, wherein the device has dimensions suitable for application to the subject at a location selected from the group consisting of the pericardium, a blood vessel, the brain, breast tissue, and the site of a hernial reconstruction or repair, and wherein the width, length, and height are between 0.1 mm and 300 mm, independently.

18. A method of making the device of claim 1, the method comprising encapsulating therapeutic, prophylactic or diagnostic agent in nano or microparticles, and covalently binding an effective amount of the particles in the prosthetic wherein the agent is released from the particles in an effective amount over an effective period of time to diagnose, reduce, prevent or alleviate at least one symptom of a disease or disorder in a subject following implantation.

19. The method of claim 18, further comprising lyophilizing the device.

20. A method of treating, preventing or diagnosing a disease or disorder in a subject, comprising implanting into a subject the device of claim 1 at a site in need thereof.

21. The device of claim 8, wherein the particles are covalently bound at a surface density between 1 and 10 μg/mm².

22. The method of claim 18, wherein the device comprises
  (a) particles that release one or more agents at a constant rate in vivo over a period of one and 24 hours; and
  (b) particles that release one or more agents at a constant rate in vivo between one and 31 days following implantation or administration of the device.

23. The method of claim 18, wherein the device is a patch selected from the group consisting of a bovine pericardium patch, a porcine pericardial patch, an autologous venous tissue patch, and a thoracic patch.

24. The method of claim 20 wherein the device has dimensions suitable for application to the subject at a location selected from the group consisting of the pericardium, a blood vessel, the brain, breast tissue, and the site of a hernial reconstruction or repair, and
  wherein the width, length, and height are between 0.1 mm and 300 mm, independently.

* * * * *